United States Patent
Ben-Tal et al.

(10) Patent No.: US 11,365,174 B2
(45) Date of Patent: Jun. 21, 2022

(54) ANTIVIRAL AGENTS FOR DRUG-RESISTANT INFLUENZA A

(71) Applicants: Thomas Jefferson University, Philadelphia, PA (US); Ramot At Tel-Aviv University LTD., Tel Aviv (IL)

(72) Inventors: Nir Ben-Tal, Tel Aviv-Jaffa (IL); Roger S. Armen, Philadelphia, PA (US); Laurence C. Eisenlohr, Merion Station, PA (US); Jitendra Belani, Paoli, PA (US); Michael Miller, Philadelphia, PA (US); Inbar Fish, Sunnyvale, CA (US); Ori Kalid, Pardes Hanna (IL)

(73) Assignees: Thomas Jefferson University, Philadelphia, PA (US); Ramot At Tel-Aviv University LTD., Tel Aviv (IL)

( * ) Notice: Subject to any disclaimer, the term of this patent is extended or adjusted under 35 U.S.C. 154(b) by 0 days.

(21) Appl. No.: 16/859,121

(22) Filed: Apr. 27, 2020

(65) Prior Publication Data

US 2020/0392076 A1 Dec. 17, 2020

Related U.S. Application Data

(63) Continuation of application No. 16/062,253, filed as application No. PCT/US2016/067470 on Dec. 19, 2016, now Pat. No. 10,676,428.

(51) Int. Cl.
| | |
|---|---|
| *C07C 311/16* | (2006.01) |
| *C07C 311/29* | (2006.01) |
| *A61K 31/63* | (2006.01) |
| *A61K 31/18* | (2006.01) |
| *A61K 31/352* | (2006.01) |
| *A61K 31/167* | (2006.01) |
| *A61K 31/04* | (2006.01) |
| *A61P 31/16* | (2006.01) |

(52) U.S. Cl.
CPC ............ *C07C 311/16* (2013.01); *A61K 31/04* (2013.01); *A61K 31/167* (2013.01); *A61K 31/18* (2013.01); *A61K 31/352* (2013.01); *A61K 31/63* (2013.01); *A61P 31/16* (2018.01); *C07C 311/29* (2013.01)

(58) Field of Classification Search
CPC ...... C07C 311/16; C07C 311/29; A61P 31/16; A61K 31/04; A61K 31/167; A61K 31/18; A61K 31/352; A61K 31/63
USPC ........................................................ 514/601
See application file for complete search history.

(56) References Cited

U.S. PATENT DOCUMENTS

| | | | |
|---|---|---|---|
| 7,049,468 | B2 | 5/2006 | Sun et al. |
| 7,875,721 | B2 | 1/2011 | Prossnitz et al. |
| 8,440,720 | B2 | 5/2013 | Wang et al. |
| 8,557,836 | B2 | 10/2013 | DeGrado et al. |
| 8,569,284 | B2 | 10/2013 | DeGrado et al. |
| 2003/0171341 | A1 | 9/2003 | Sun et al. |
| 2005/0176758 | A1 | 8/2005 | Bischofberger et al. |
| 2011/0028510 | A1 | 2/2011 | Altmeyer et al. |
| 2011/0065766 | A1 | 3/2011 | Wang et al. |
| 2014/0194476 | A1 | 7/2014 | Wolkerstorfer et al. |

FOREIGN PATENT DOCUMENTS

| | | |
|---|---|---|
| WO | 2006067584 A1 | 6/2006 |
| WO | 2006081658 A1 | 8/2006 |
| WO | 2014121170 A2 | 8/2014 |
| WO | 2015187827 A1 | 12/2015 |

OTHER PUBLICATIONS

Hsieh et al., Identification of Ligands with Bicyclic Scaffolds Provides Insights into Mechanisms of Estrogen Receptor Subtype Selectivity, 2006, Journal of Biological Chemistry, 281(26), 17909-17919 (Year: 2006).*
Al Abdullah, ES, Synthesis and Biological Testing of New 1-Adamantyl Derivatives, Ph.D. dissertation, King Saud University, pp. 1-168, 2007, p. 4, paragraph 2, see compound 11.
Pubchem N-benzyl-2,4,6-trimethylbenzenesulfonamide, CID 749837, pp. 1-14, Jul. 8, 2005, p. 4, see 2D structure.
Pubchem SCHEMBL7794431, CID 21993392, pp. 1-11, Dec. 5, 2007; p. 4, see 2D structure.
Pubchem ZINC00469292, CID 892998, pp. 1-14, Jul. 9, 2005; p. 3, see 2D structure.
International Search Report and Written Opinion of PCT/US16/67470 dated Feb. 21, 2017.
Agamennone, M., et al., "Identification of small molecules acting against H1N1 influenza A virus", Virology, Elsevier, Asterdam, NL, vol. 488, pp. 249-258, 2015.
Database Registry (Online), Chemical Abstracts Service, Columbus, Ohio, Jun. 9, 2013, Retrieved from STN Accession No. 1436178-76-5, 2013.
Supplementary European Search Report and Written Opinion dated Jan. 27, 2020 in corresponding European Patent Application No. 16876895.0.

(Continued)

*Primary Examiner* — Kristin A Vajda
(74) *Attorney, Agent, or Firm* — Cozen O'Connor

(57) ABSTRACT

An effective therapeutic agent for the M2 channel comprising sulfonylamide or oxabicyclo structures effective for treating amantadine-resistant influenza A infections, and methods of treating amantadine-resistant influenza A infections through administration of the same.

7 Claims, 63 Drawing Sheets

Specification includes a Sequence Listing.

(56) References Cited

OTHER PUBLICATIONS

Hamann, L.G., et al., "Structure-activity relationships and sub-type selectivity in an oxabicyclic estrogen receptor α/β agonist scaffold", Bioorganic & Medicinal Chemistry Letters, vol. 15, No. 5, pp. 1463-1466, 2005.

Hsieh, R.W., et al., "Identification of Ligands with Bicyclic Scaffolds Provides Insights into Mechanisms of Estrogen Receptor Subtype Selectivity", Journal of Biological Chemistry, vol. 281, No. 26, pp. 17909-17919, 2016.

Wang, J., et al., "Discovery of Novel Dual Inhibitors of the Wild-Type and the Most Prevalent Drug-Resistant Mutant, 331N, of the M2 Proton Channel from Influenza A Virus", Journal of Medicinal Chemistry, vol. 56, No. 7, pp. 2804-2812, 2013.

Yu, Y., et al., "Synthesis and structure-activity relationship study of arylsulfonamides as novel potent H5N1 inhibitors", European Journal of Medicinal Chemistry, Elsevier, Amsterdam, NL, vol. 159, pp. 206-216, 2018.

\* cited by examiner

FIG. 1

| Compound/Analog | Hit2Lead # | | IC50 (uM) | |
|---|---|---|---|---|
| Compound #1 | 5118196 | Very active! | 1 | |
| 1 | 5118144 | INACTIVE | ----- | |
| 2 | 5602340 | Very active! | < 1uM | |
| 3 | 5118177 | INACTIVE | ----- | related to #1 |
| 4 | 5358567 | Very active! | < 1uM | |
| 5 | 5613320 | Very active! | 2.5 | |
| Compound #3 | 5236210 | Active | > 10 uM | |
| 6 | 6112468 | INACTIVE | ----- | |
| 7 | 9156412 | Active | ~ 10 uM | |
| 8 | 5355243 | INACTIVE | ----- | |
| 9 | 7678527 | INACTIVE | ----- | |
| 10 | 6826511 | INACTIVE | ----- | |
| 11 | 7554132 | Active | 10 uM | |
| 12 | 5345306 | INACTIVE | ----- | |
| 13 | 5348568 | INACTIVE | ----- | |
| 14 | 5350713 | INACTIVE | ----- | |
| 15 | 5350444 | INACTIVE | ----- | related to #3 |
| 16 | 5116391 | INACTIVE | ----- | |
| 17 | 5522818 | INACTIVE | ----- | |
| 24 | 5277665 | INACTIVE | ----- | |
| 25 | 5273595 | INACTIVE | ----- | |
| 26 | MCULE-24724 | INACTIVE | ----- | |
| 27 | MCULE-31262 | Active | > 10 uM | |
| 28 | MCULE-20747 | INACTIVE | ----- | |
| 29 | C927-0021che | INACTIVE | ----- | |
| 30 | D445-0314che | INACTIVE | ----- | |
| 31 | Y030-0764che | Very active! | 1 | |
| Compound #16 | 5235068 | Active | 10 | |
| 18 | 6117368 | Very active! | 1.5 | |
| 19 | 5144435 | INACTIVE | ----- | |
| 20 | 6066012 | INACTIVE | ----- | related to #16 |
| 21 | 7862498 | Active | 8 | |
| 22 | 7845552 | INACTIVE | ----- | |
| Compound #19 | 5142920 | Active | 8.5 | |
| 23 | 5144344 | Active | 3 | related to #19 |

FIG. 2A
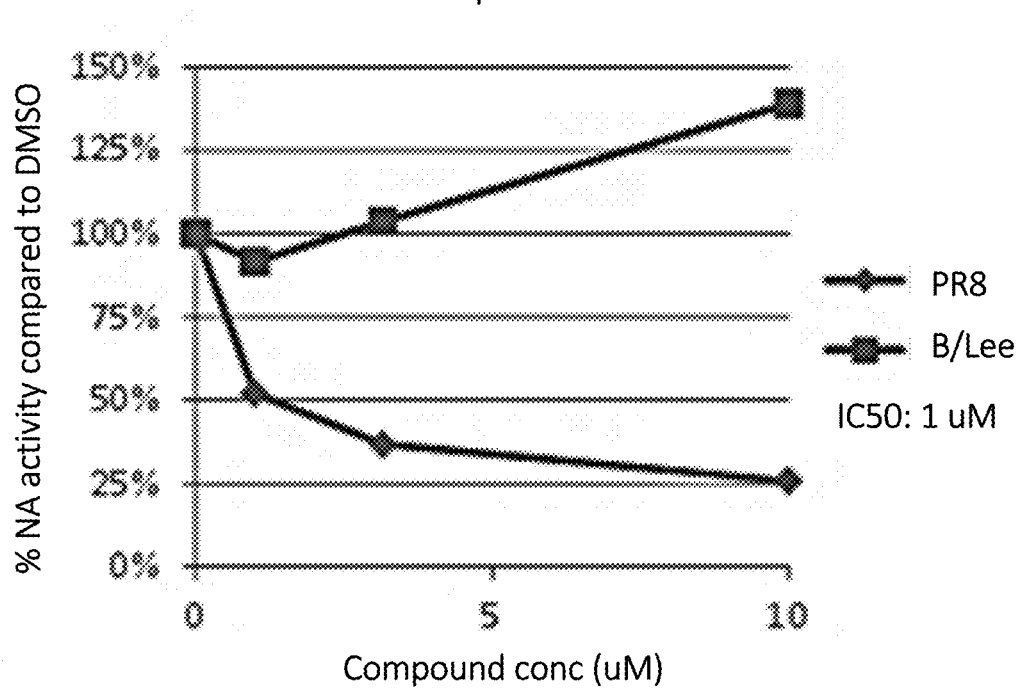
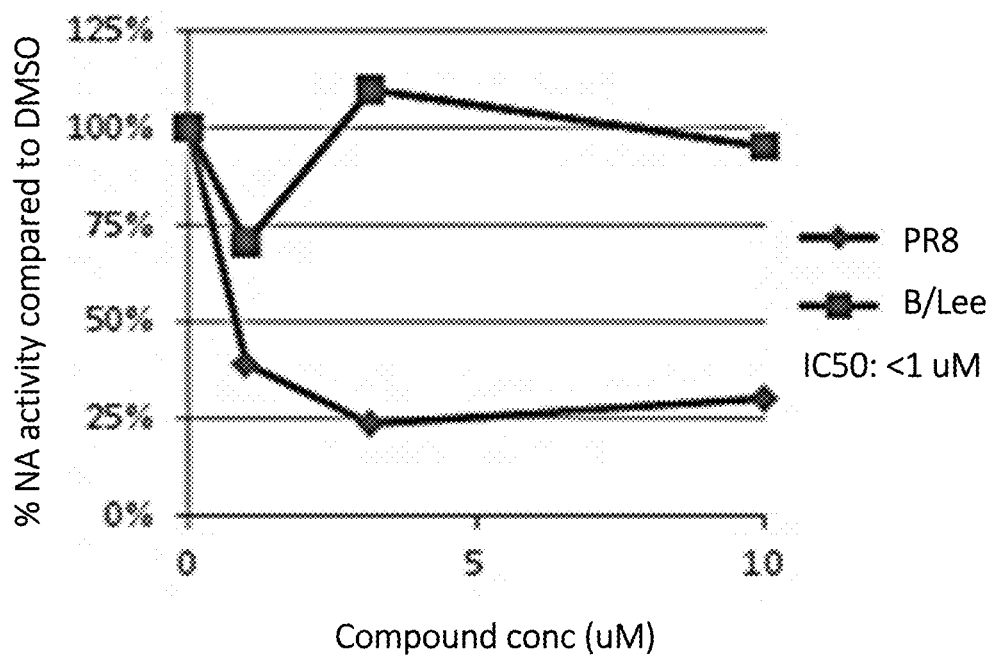

FIG. 2B
Analog # 4
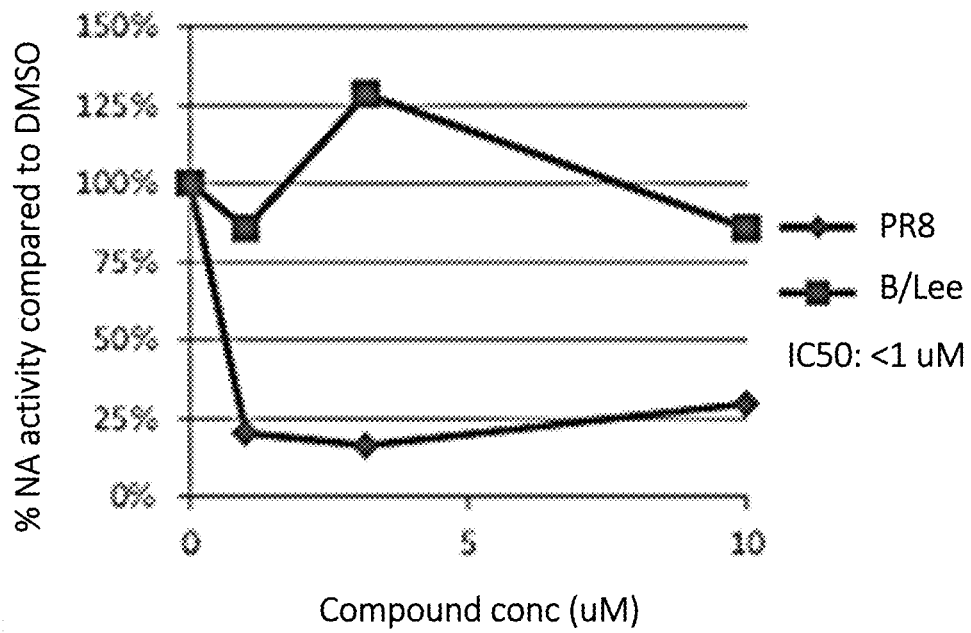
Analog # 5
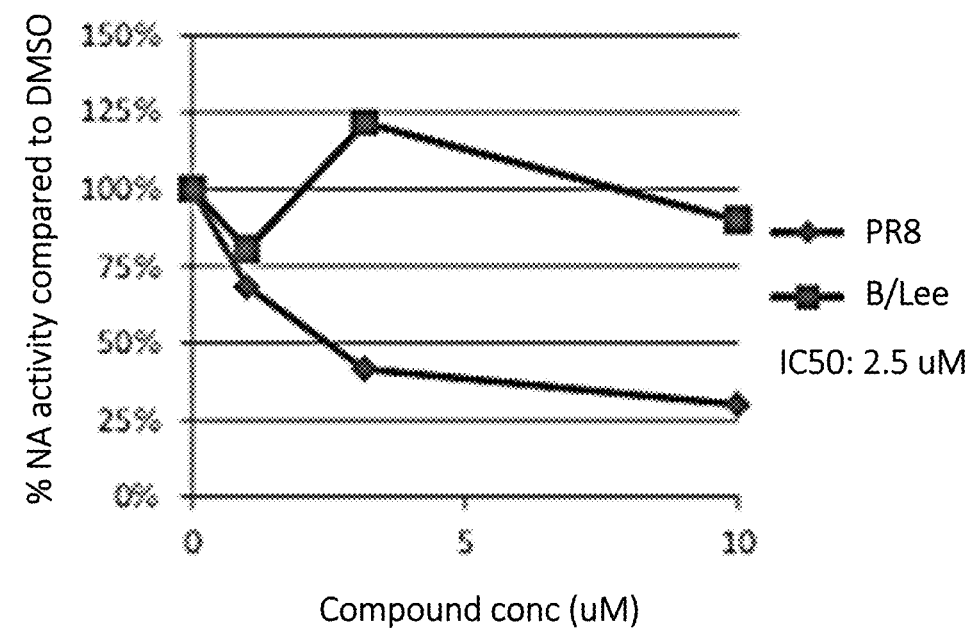

FIG. 3A
Compound # 3
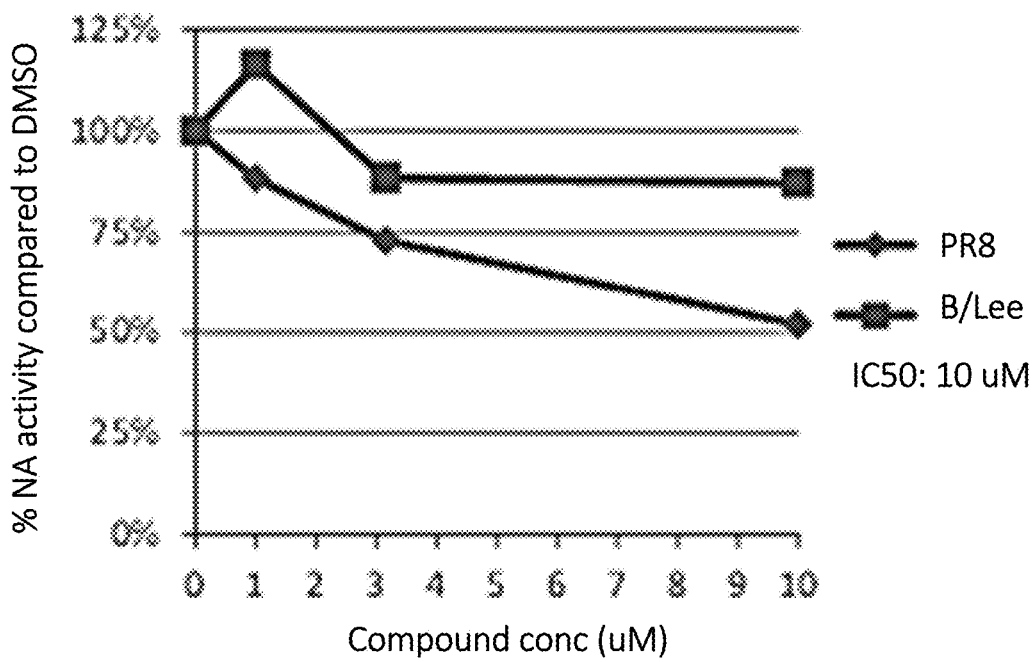
Analog # 7
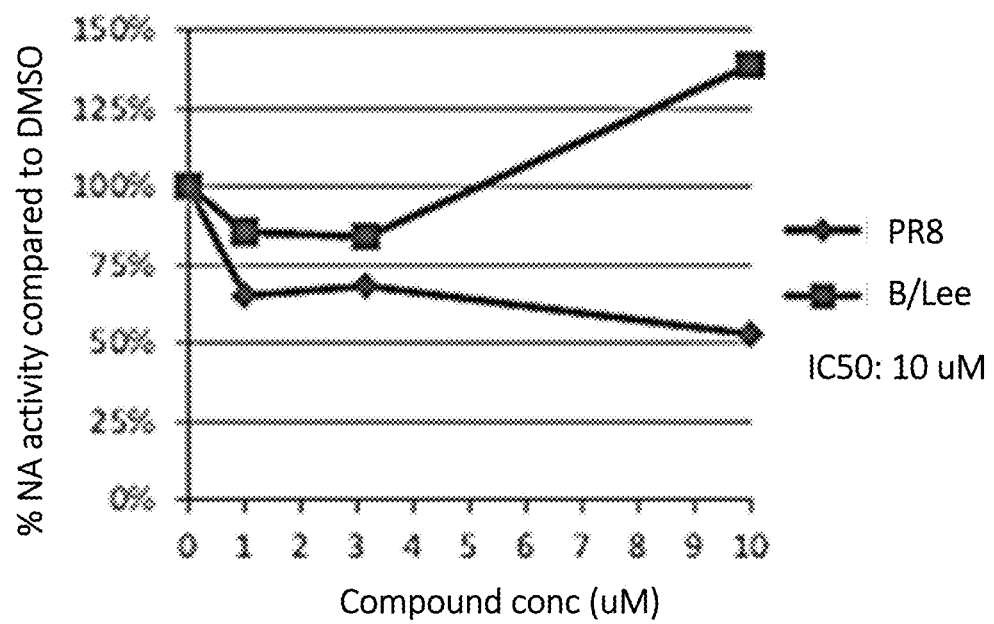

FIG. 3B
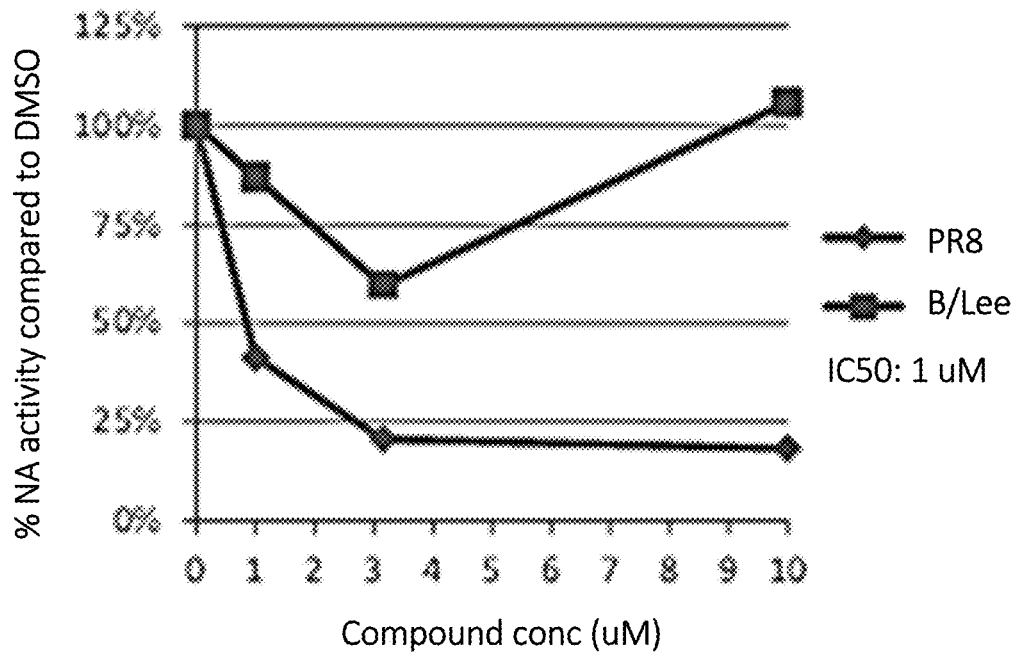
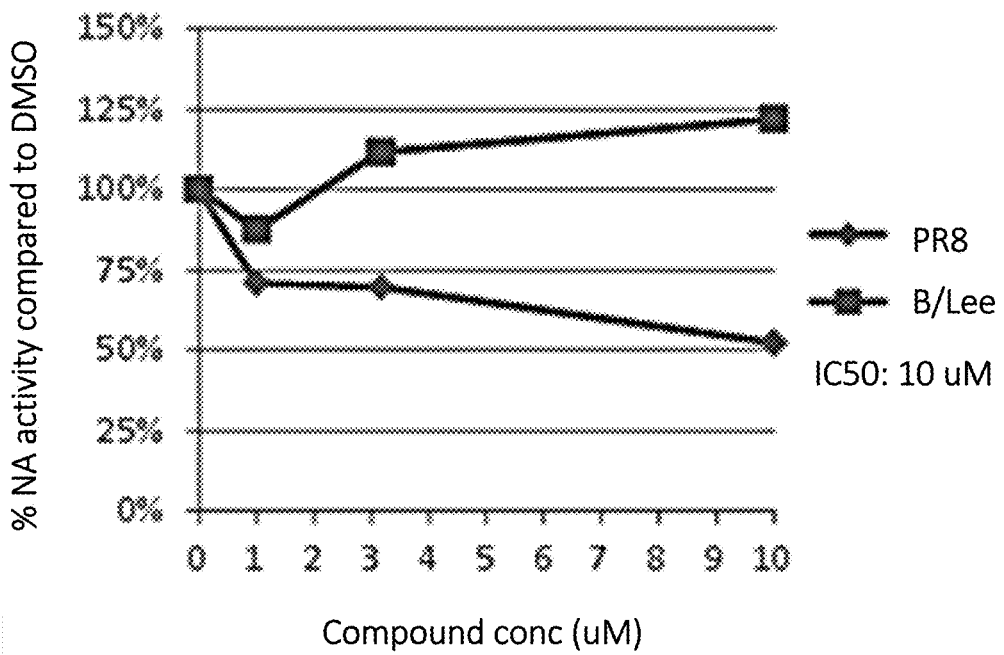

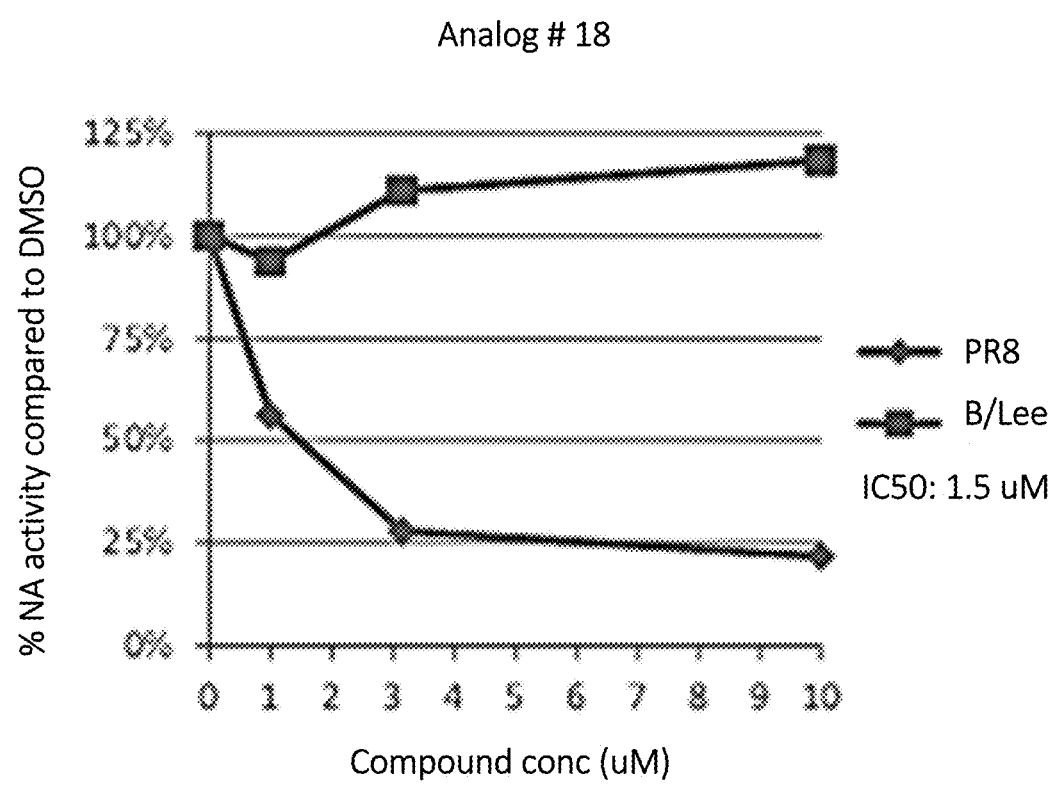

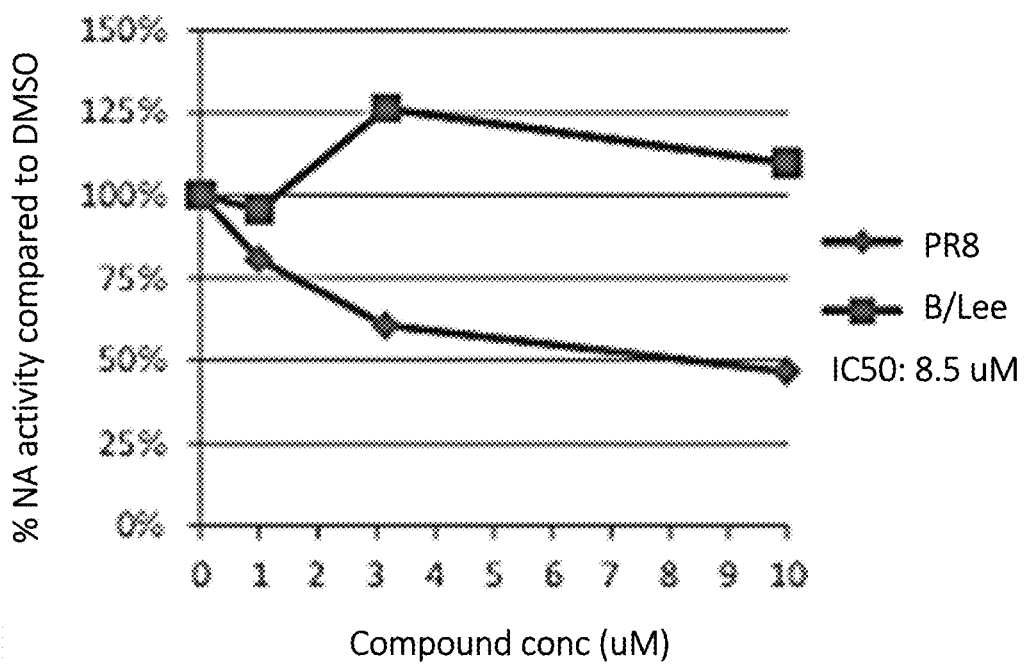

Analog # 23

FIG.6B – continued
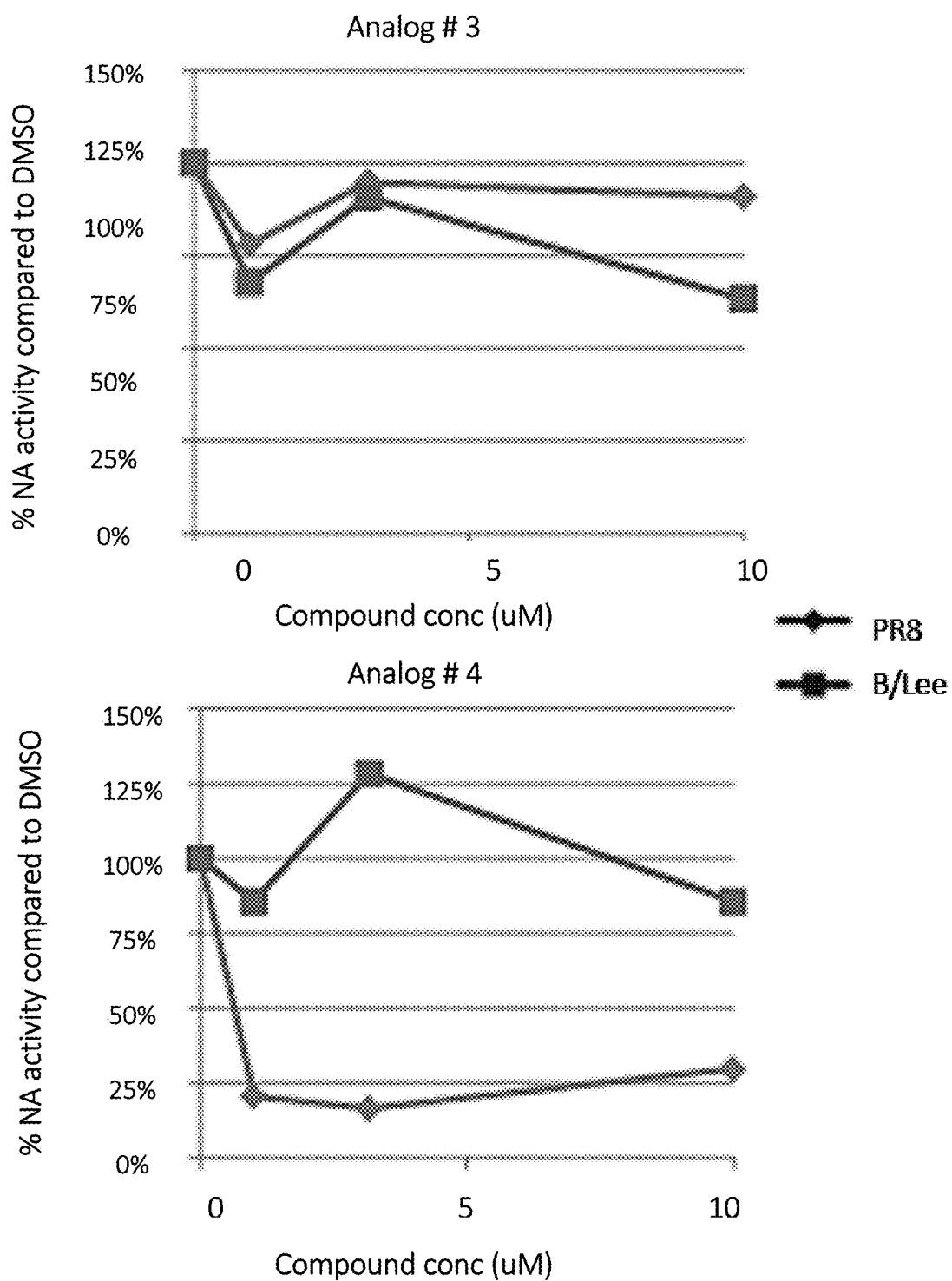

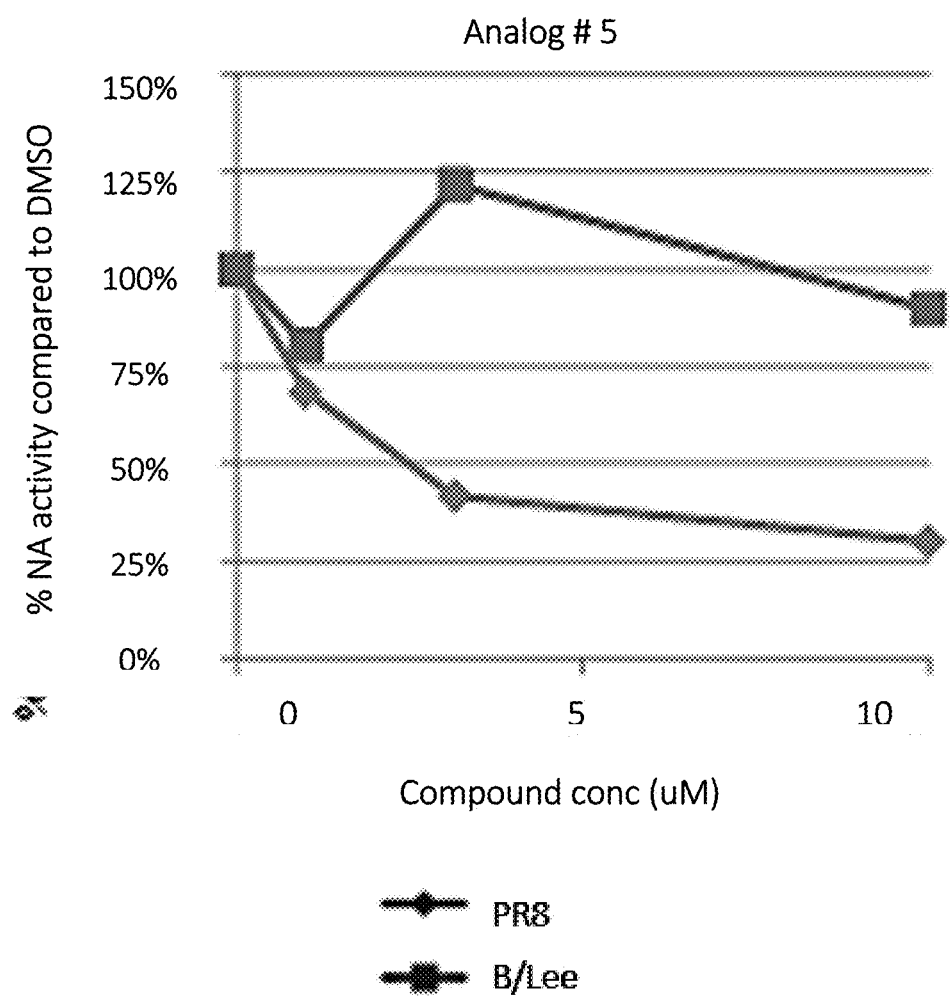
FIG.6B - continued

FIG.7B
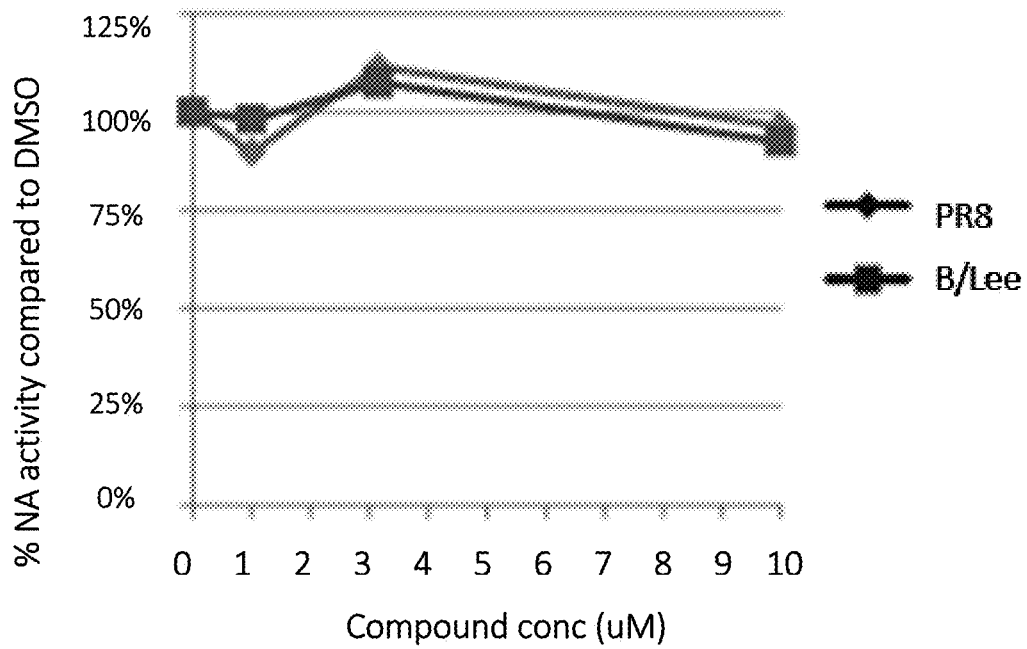
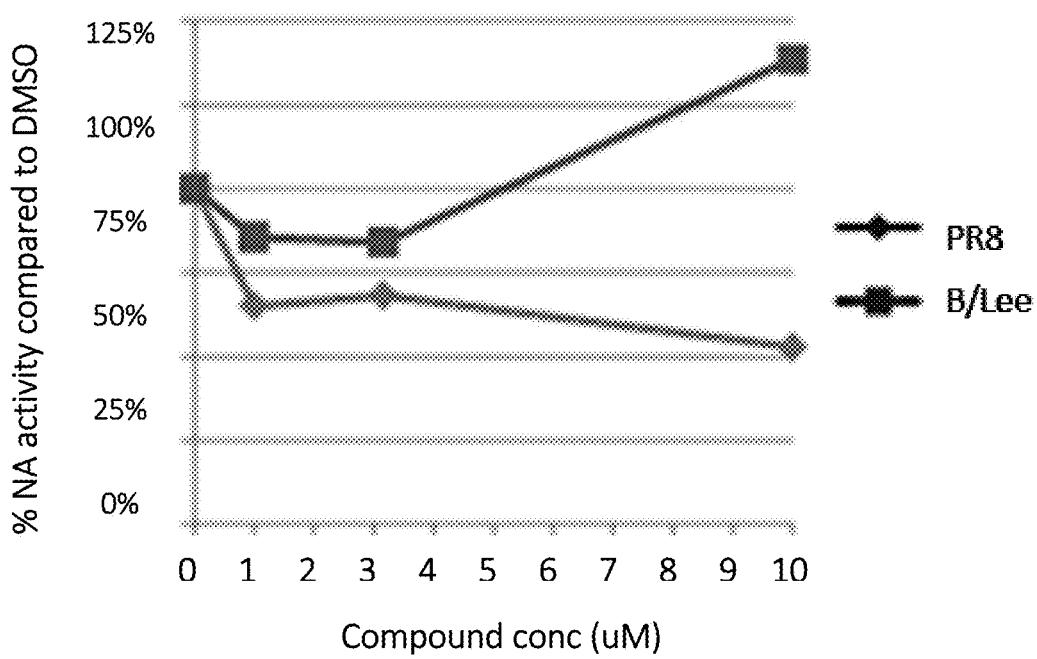

FIG.7B – continued
Analog # 8
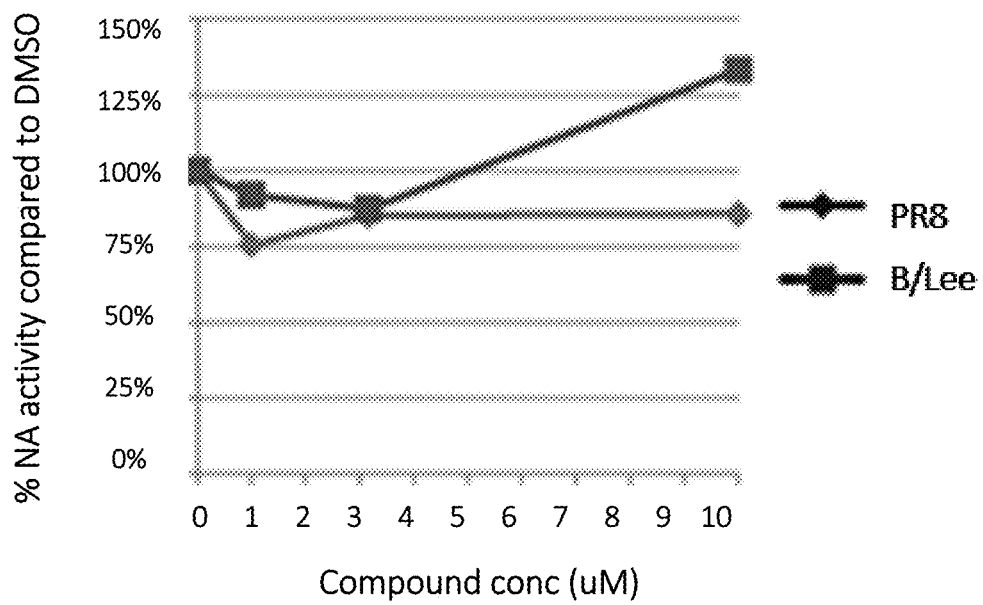
Analog #9
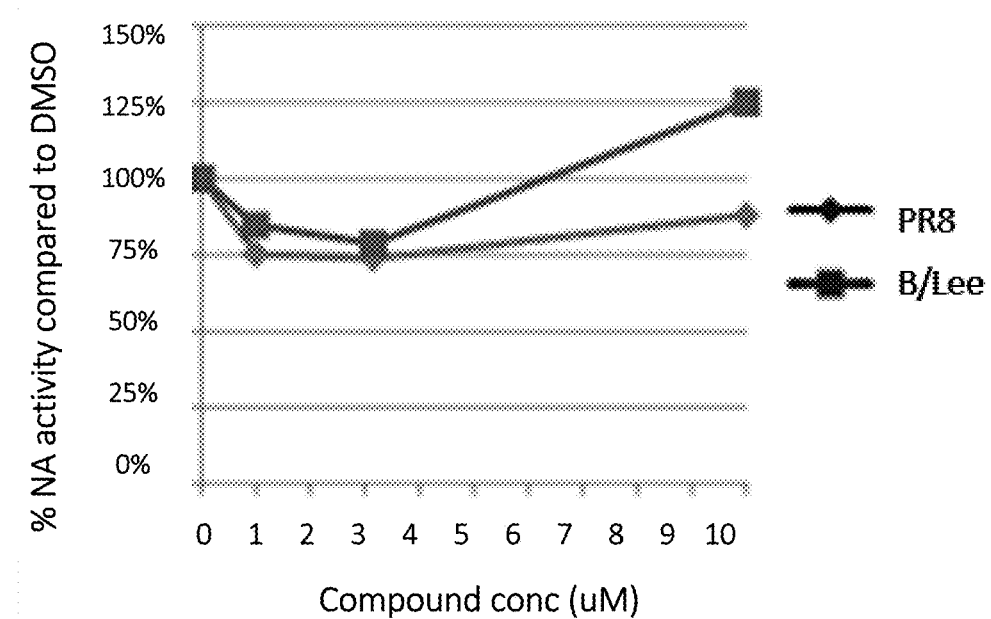

FIG.7B – continued
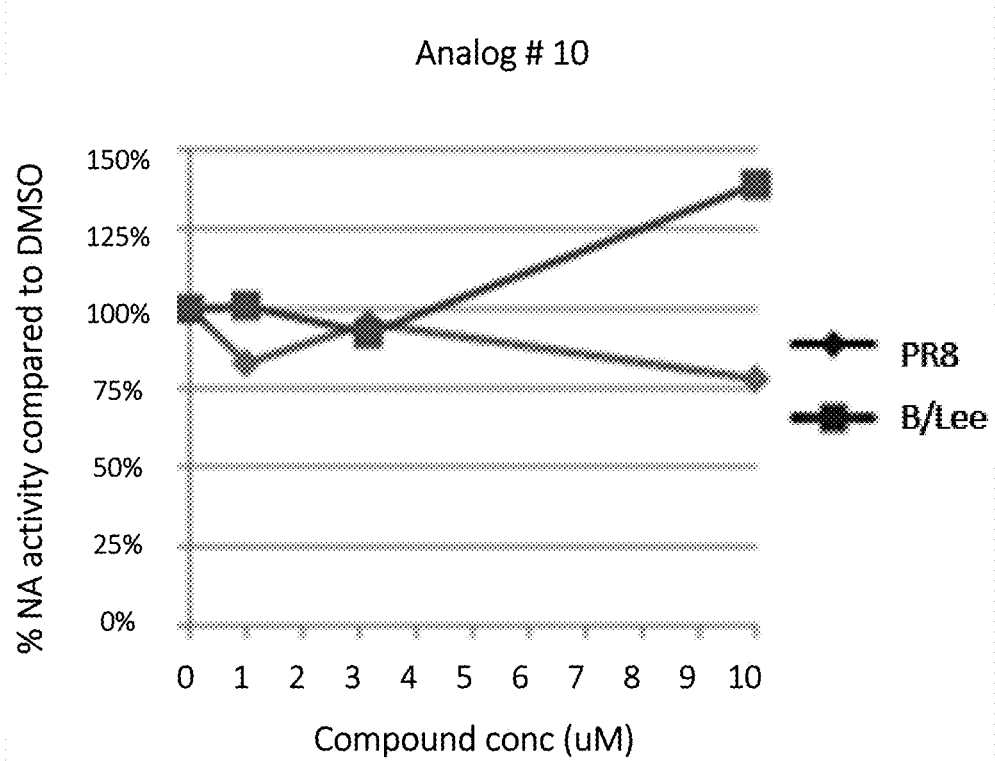

FIG. 10B
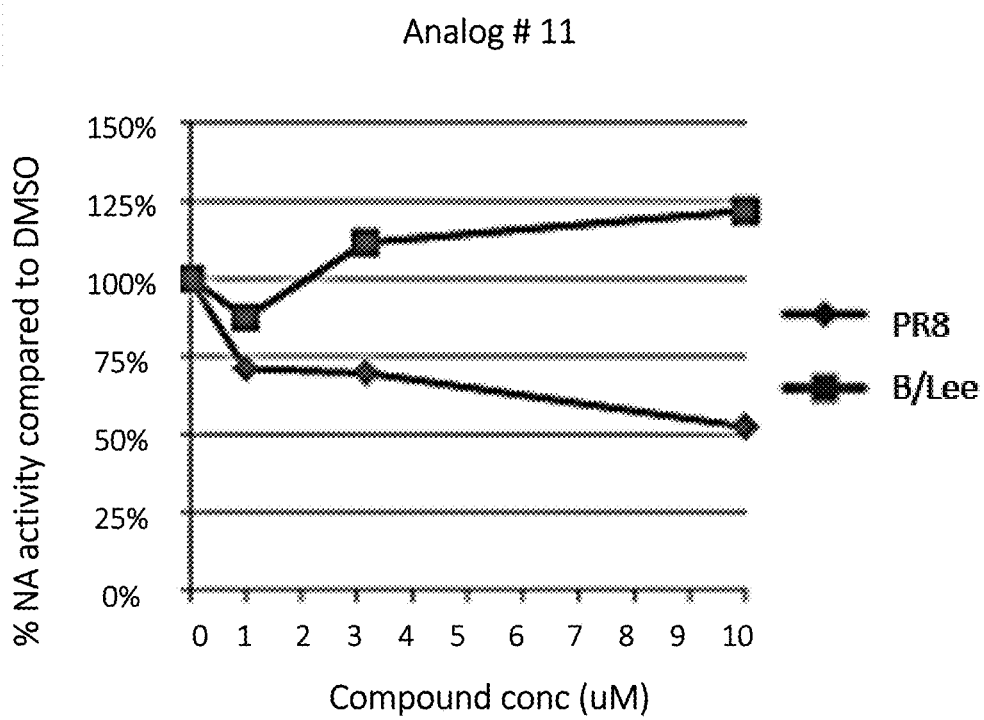
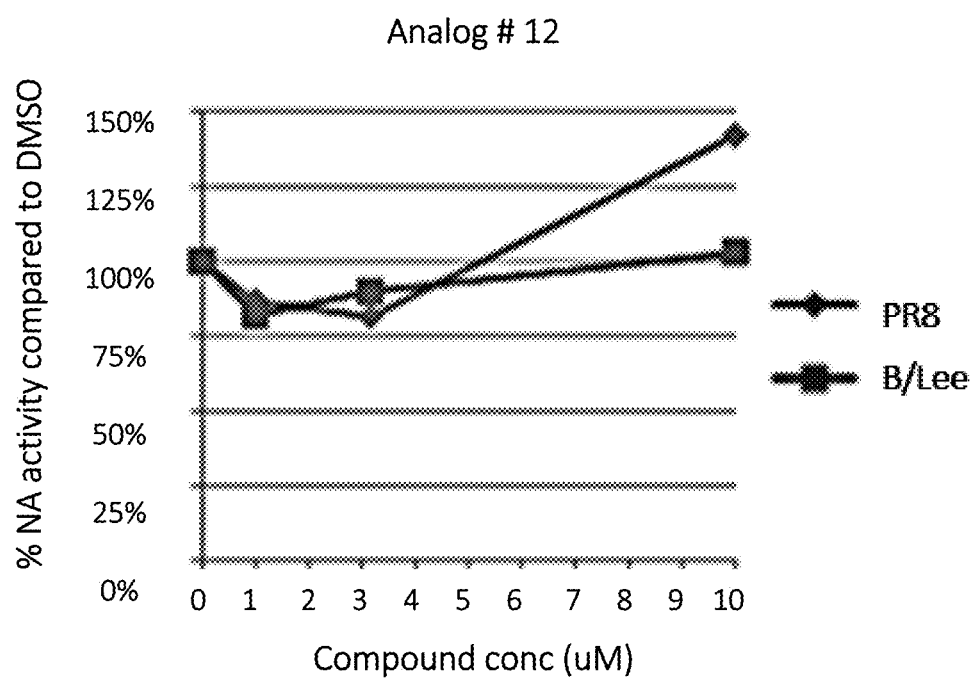

FIG. 10B - continued
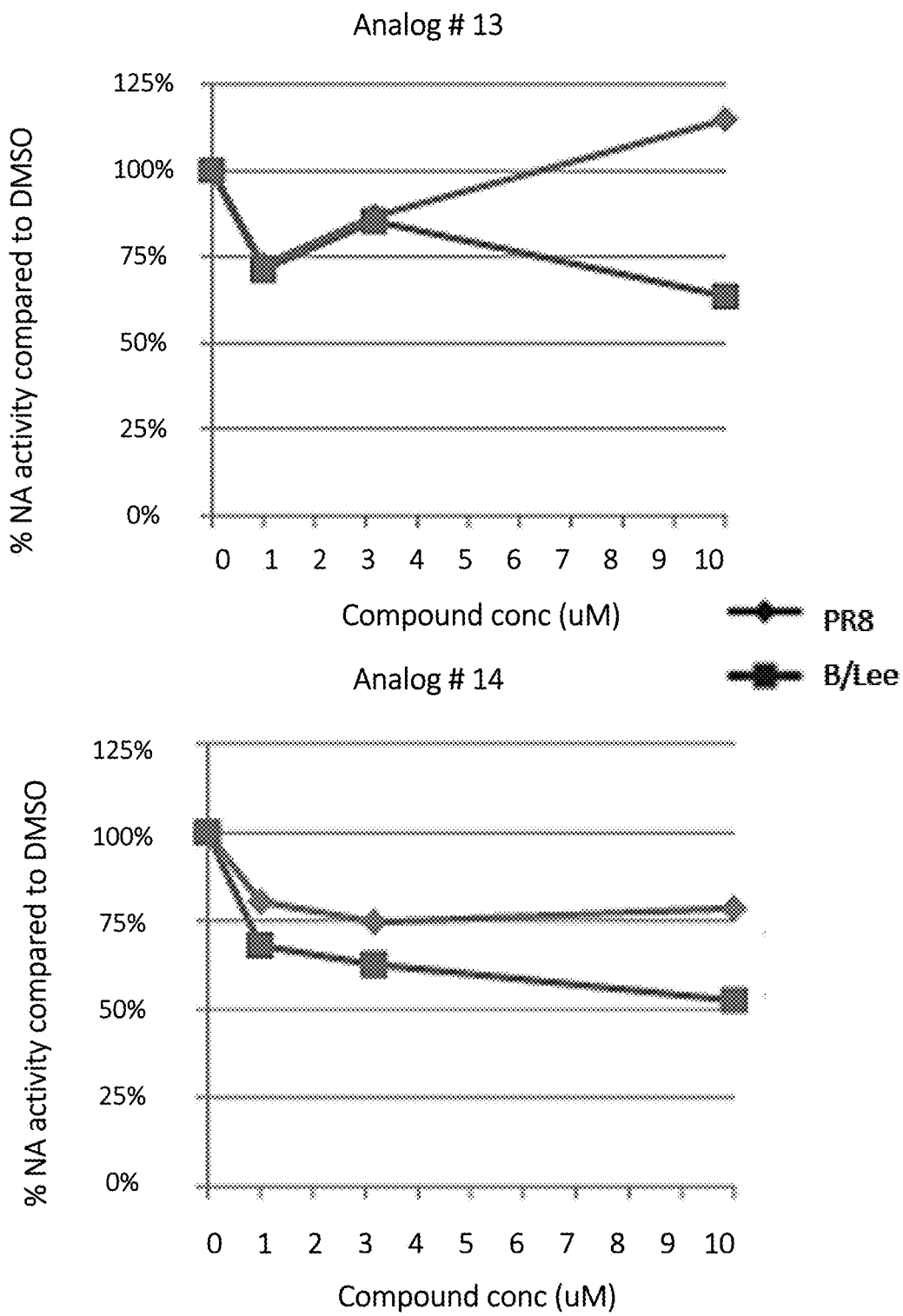

FIG. 10B – continued
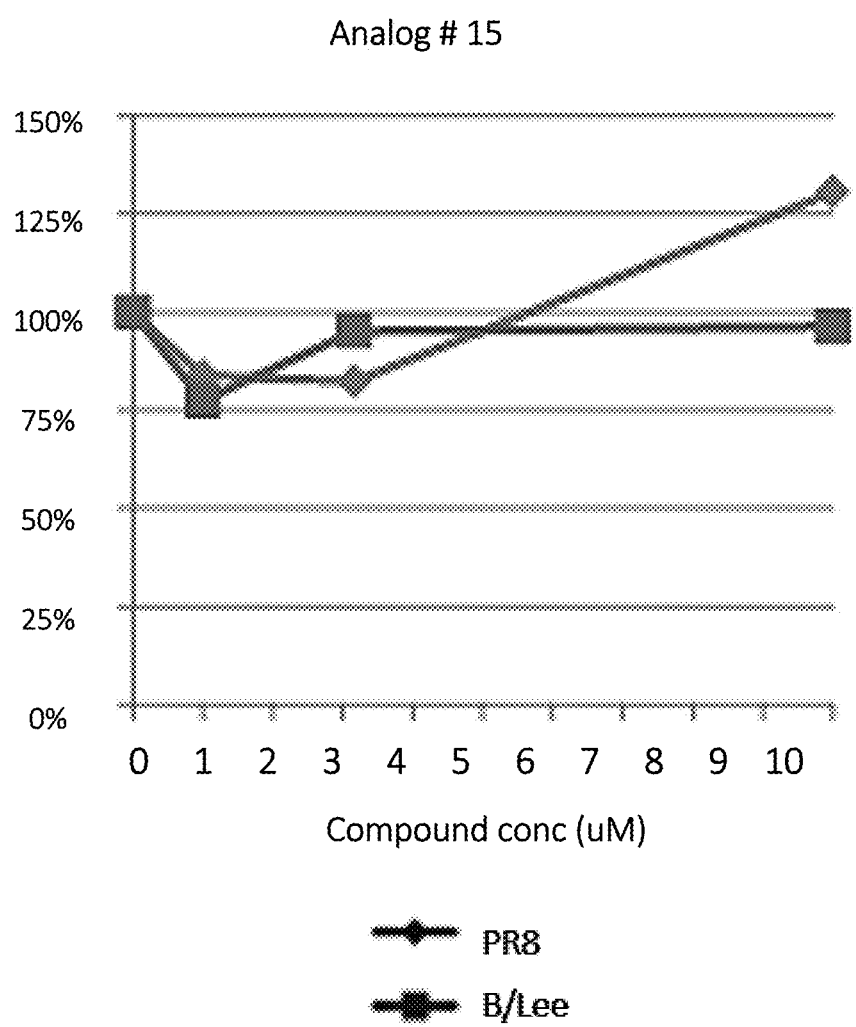

FIG. 15B - continued
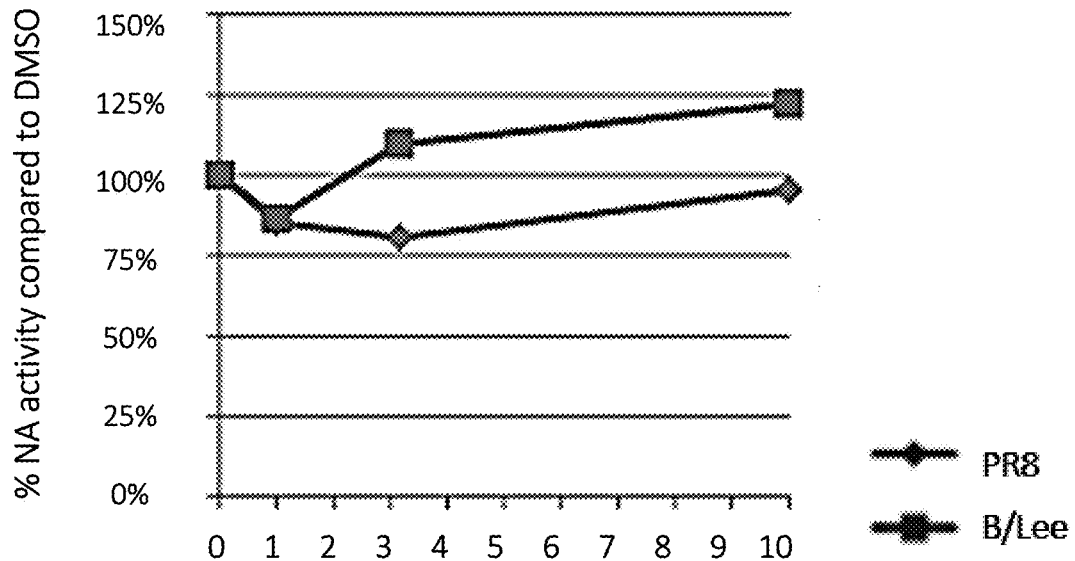
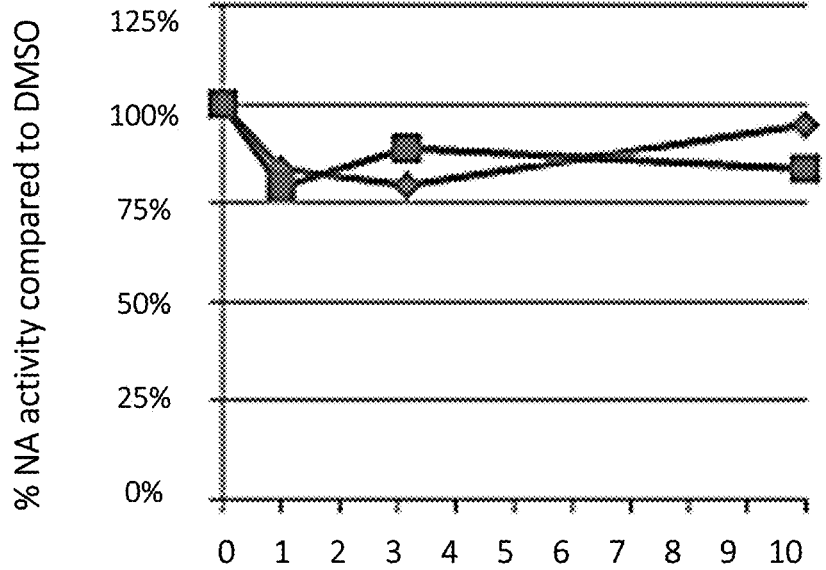

FIG. 15B - continued
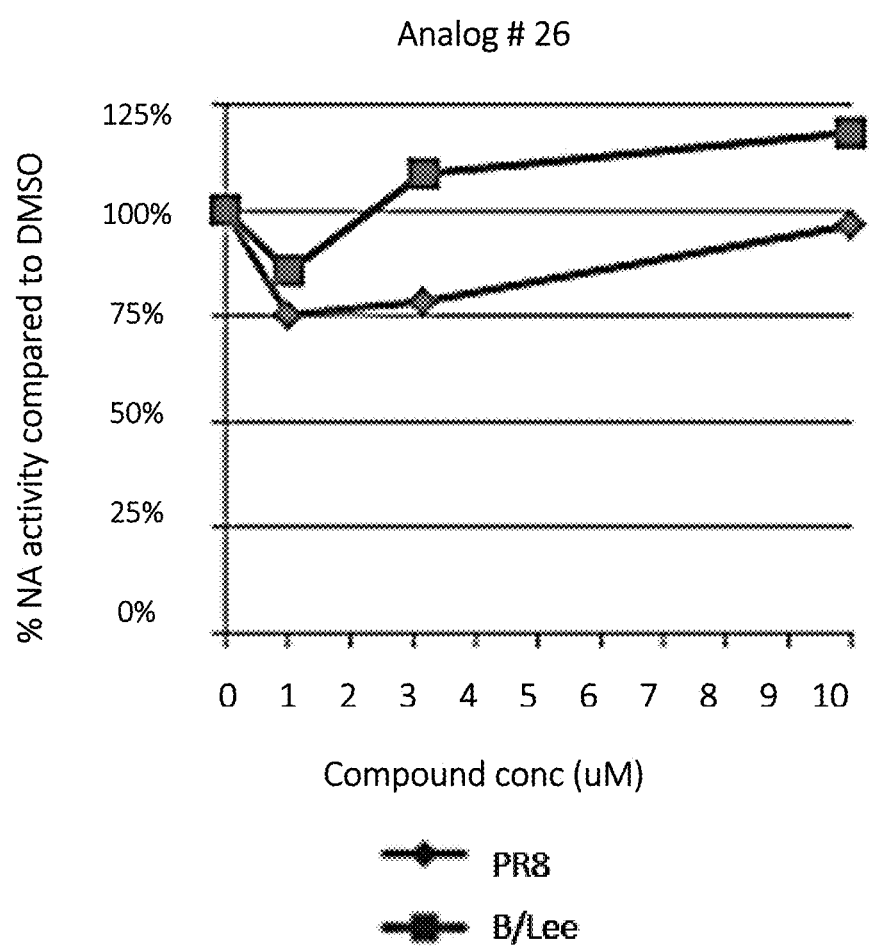

Compound # 3

FIG. 16B
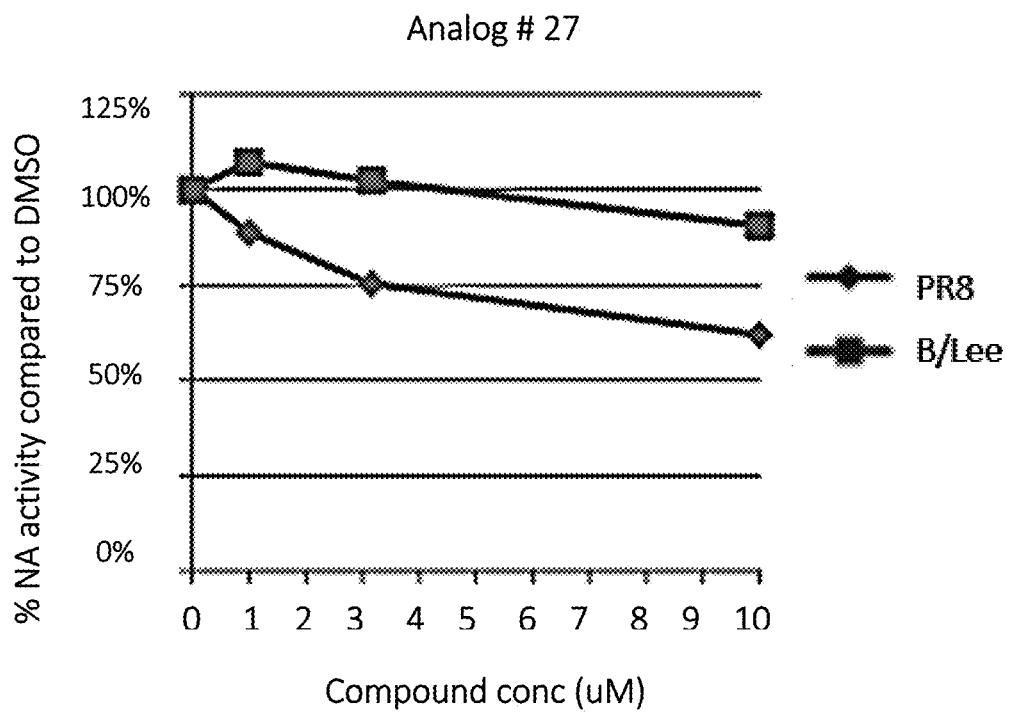
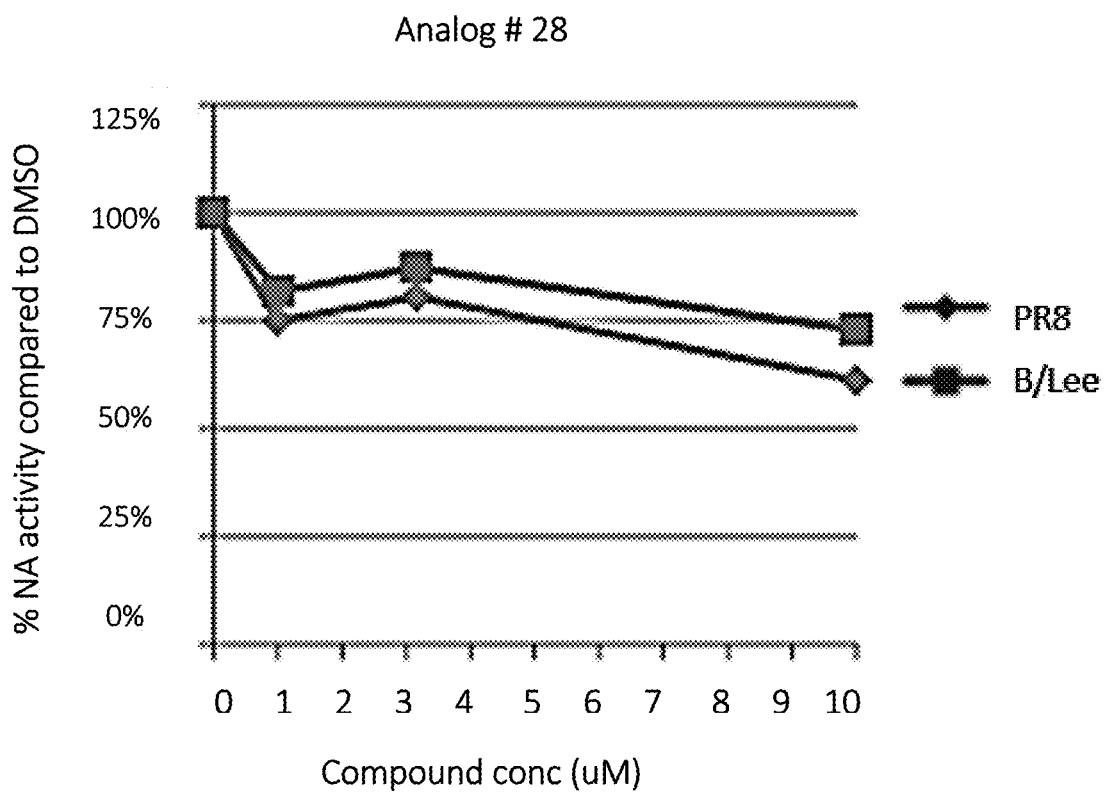

FIG. 16B – continued
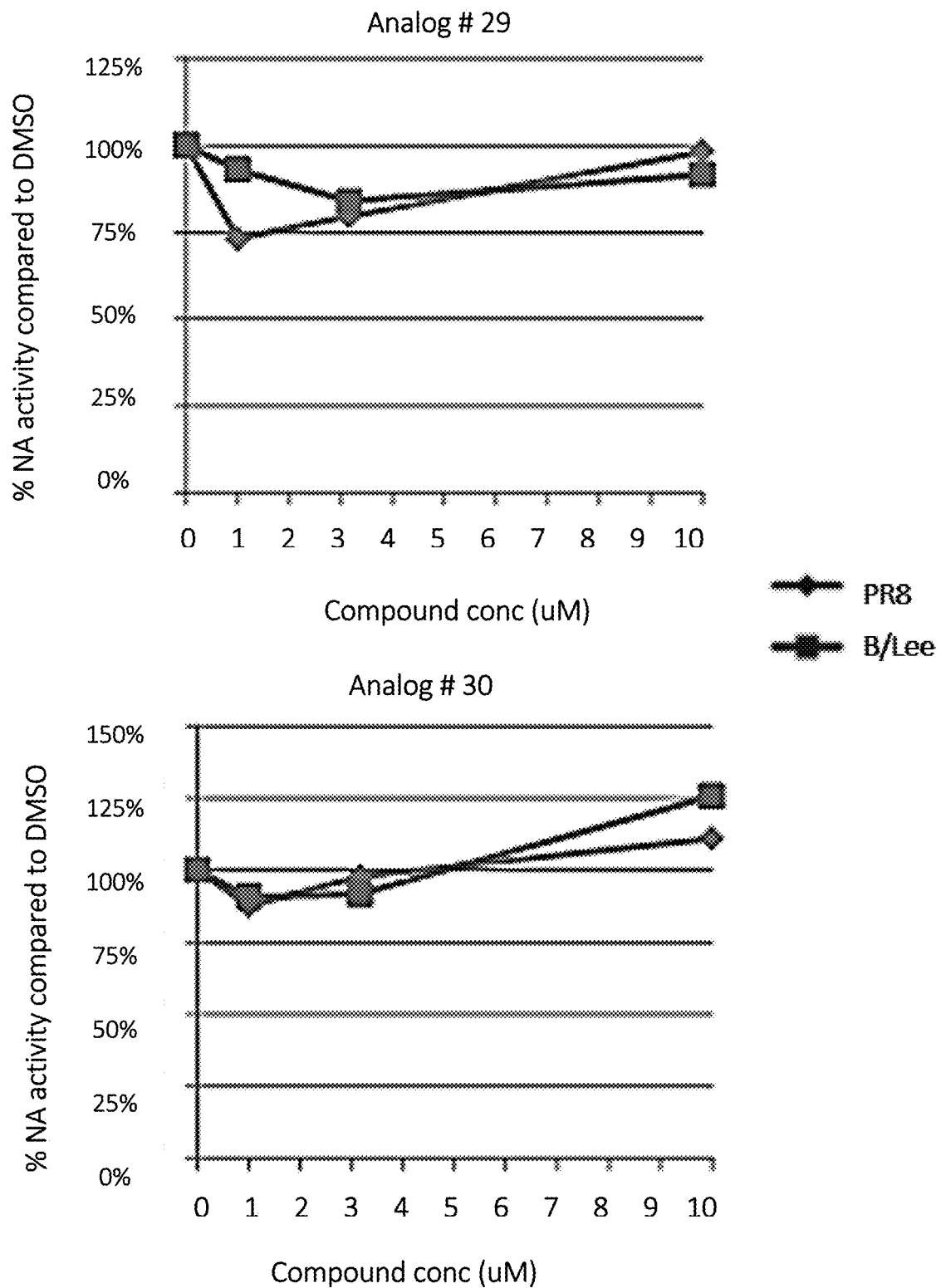

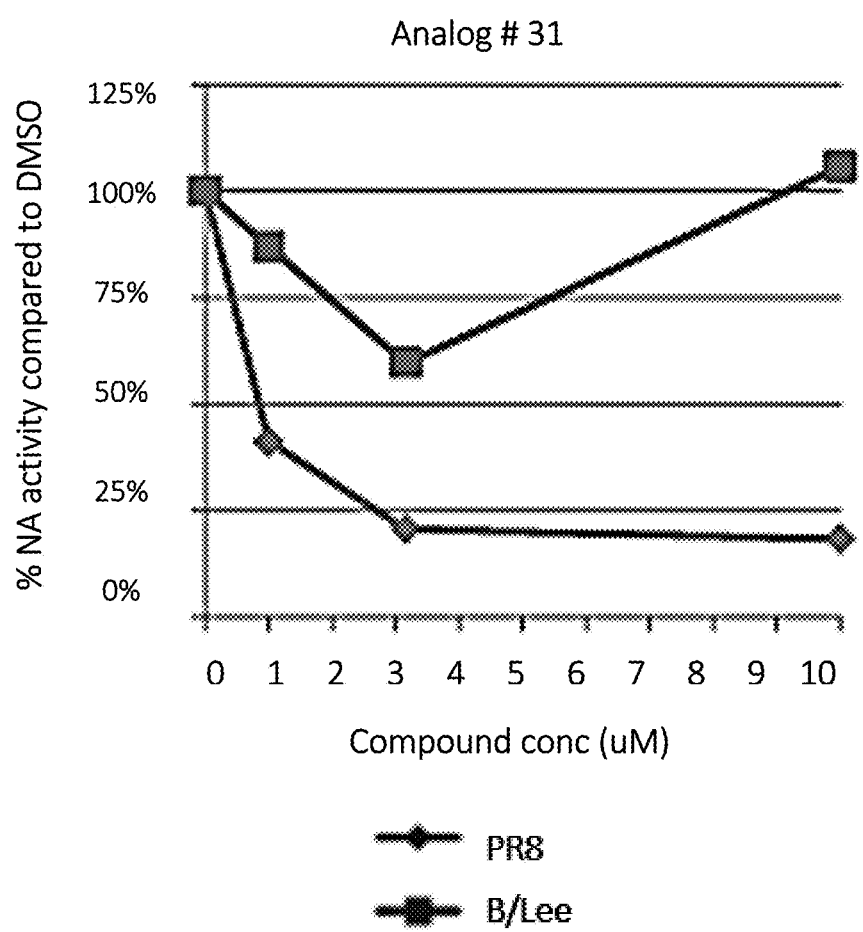
FIG. 16B - continued

FIG. 19 – continued
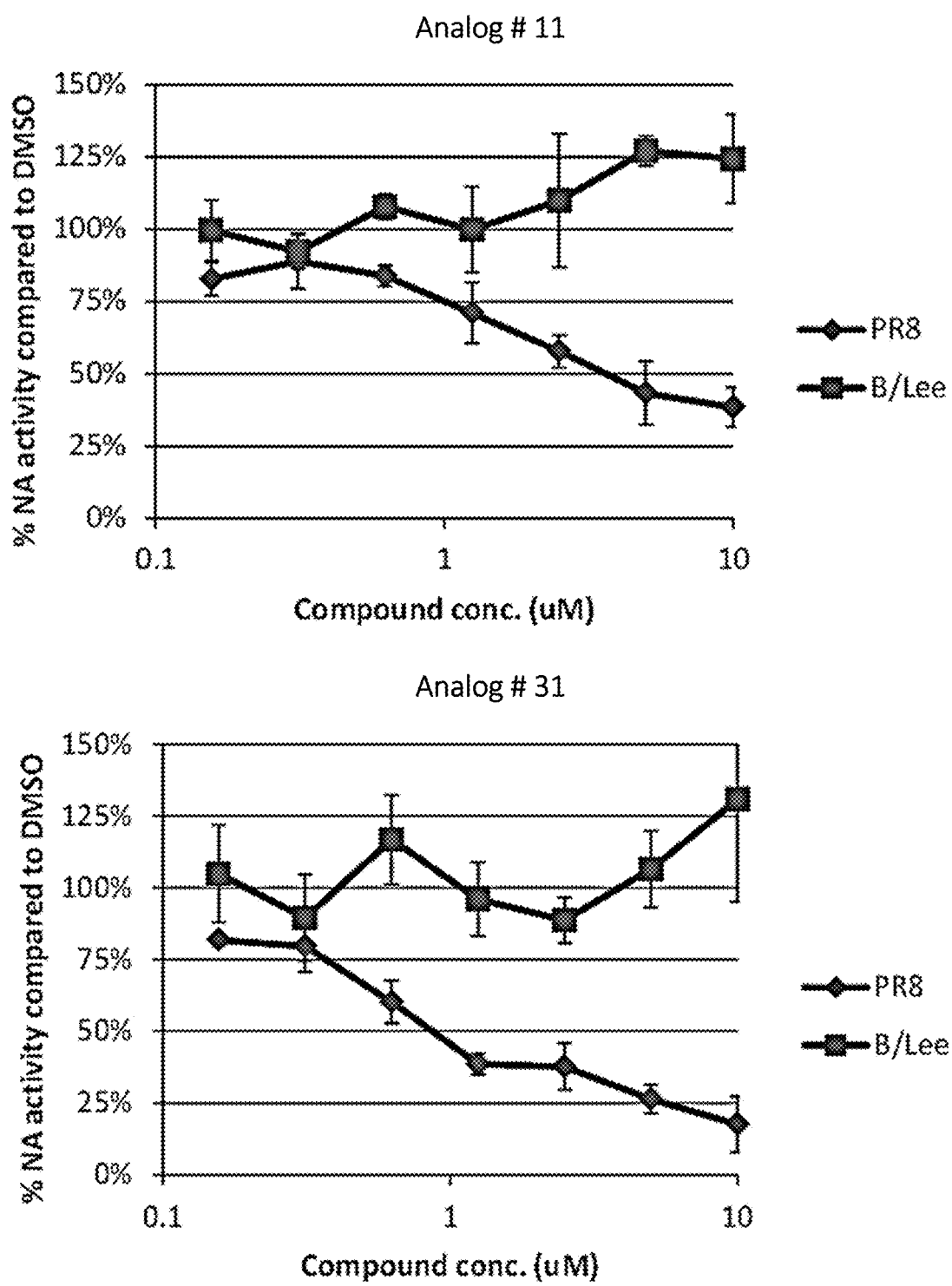

FIG. 19 – continued
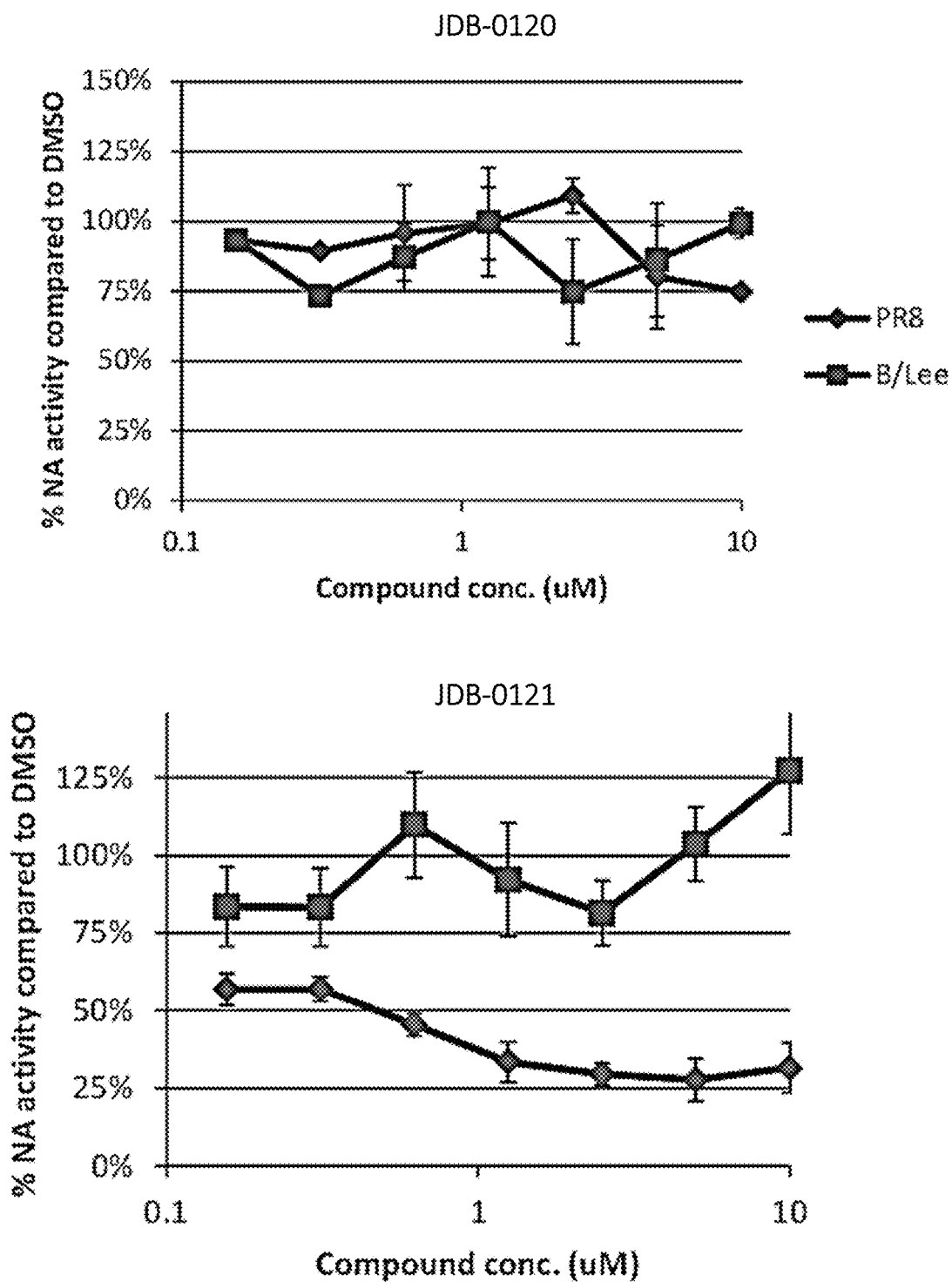

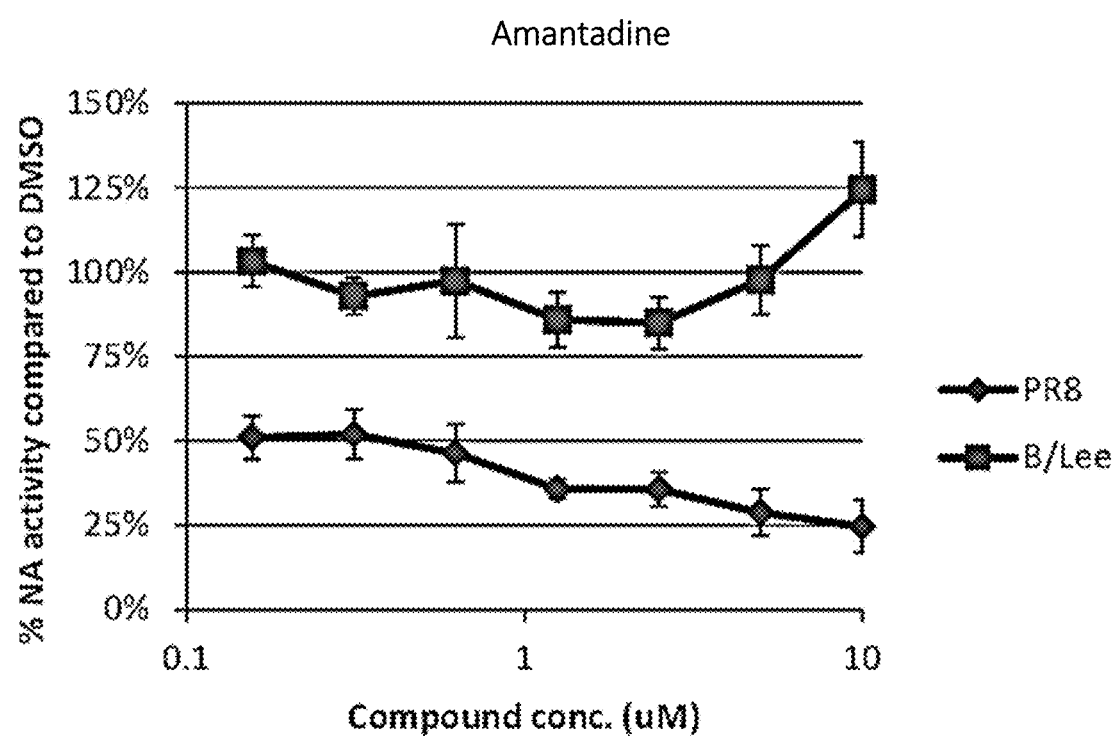
FIG. 19 – continued

FIG. 21
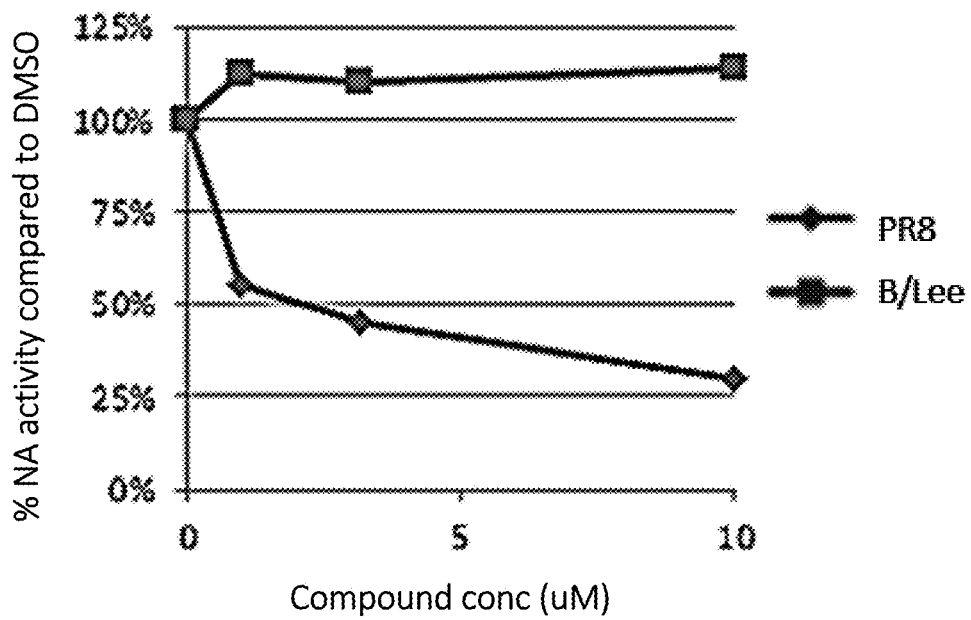
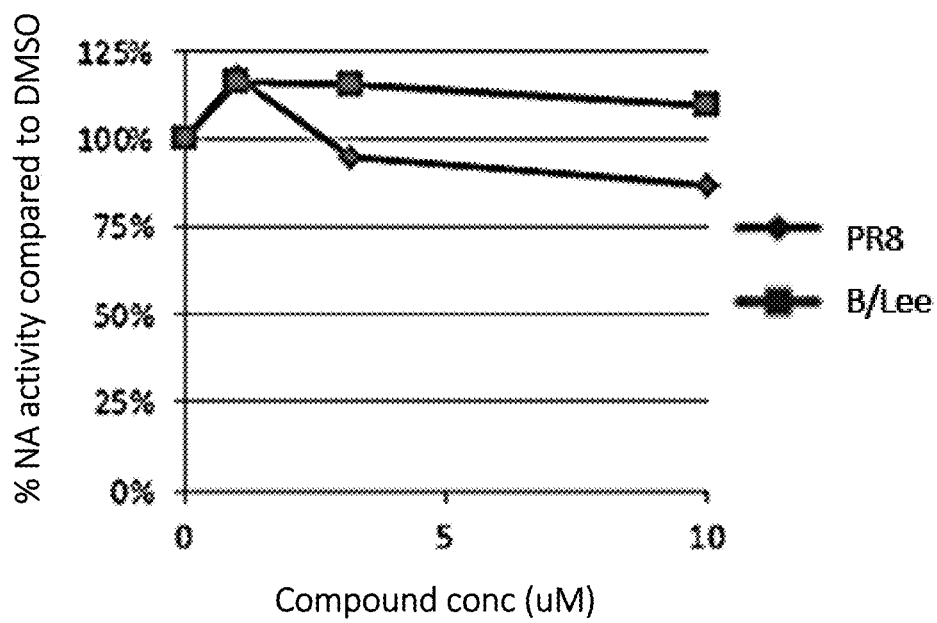

FIG. 21- continued
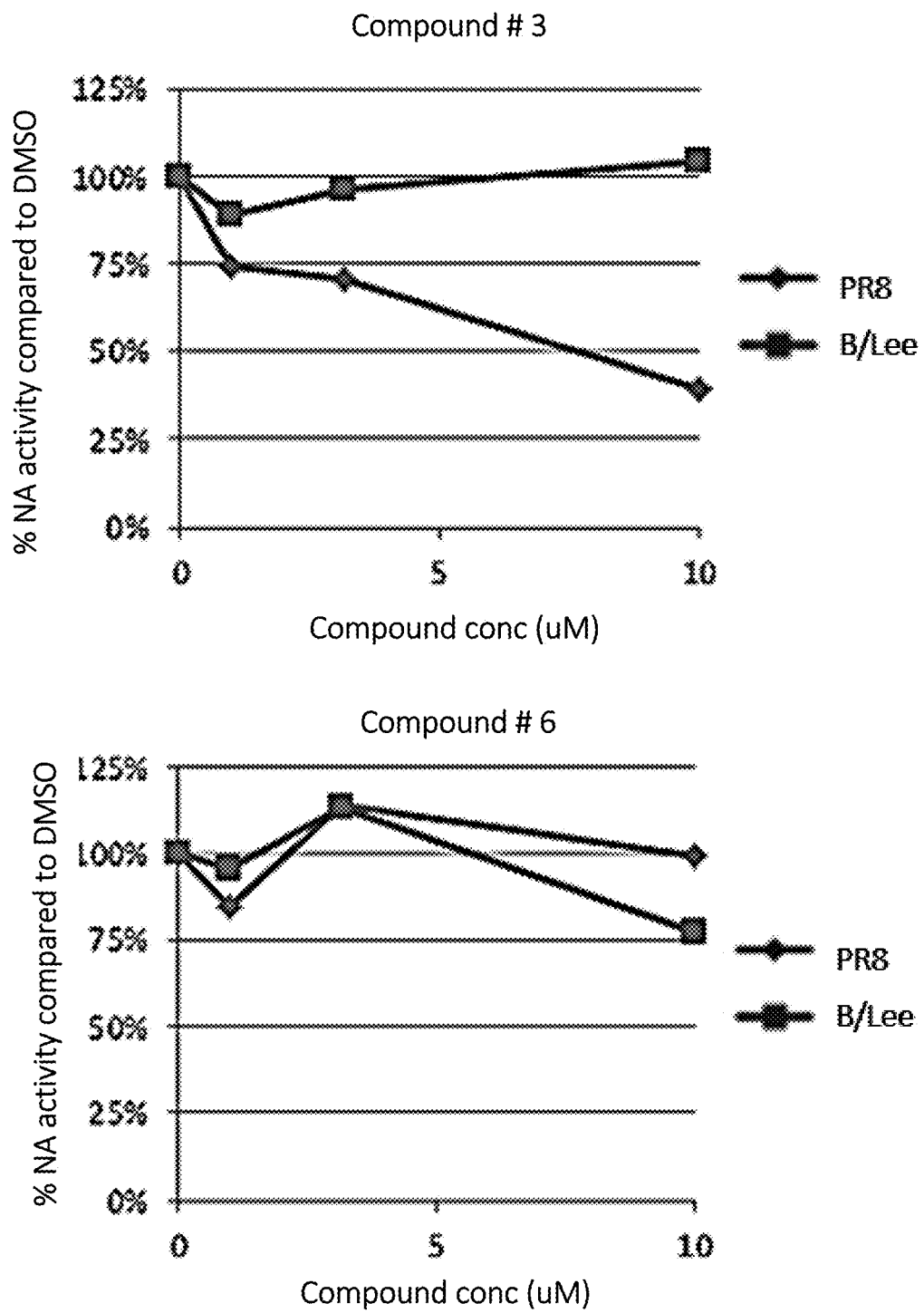

FIG. 21 - continued
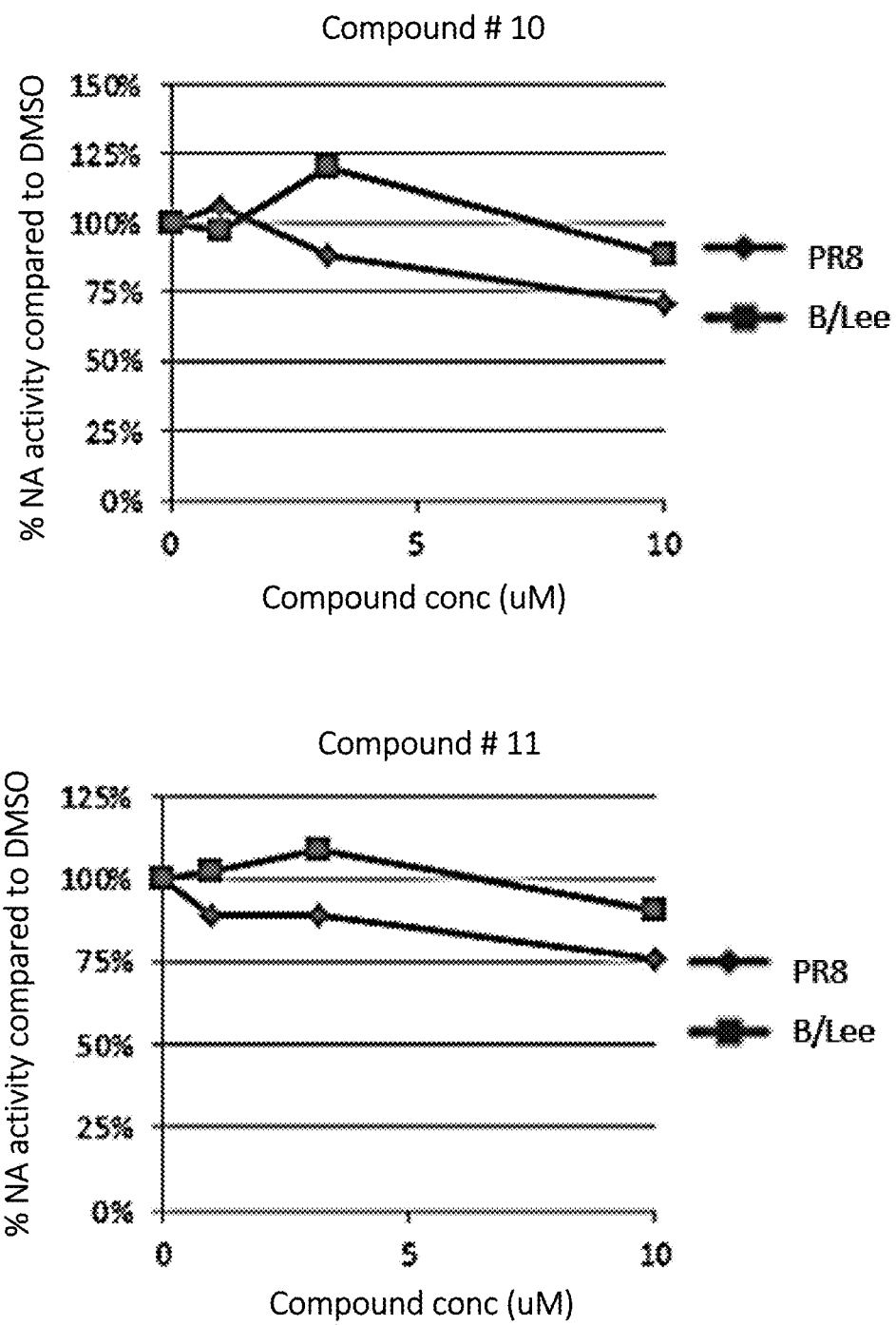

FIG. 21 – continued
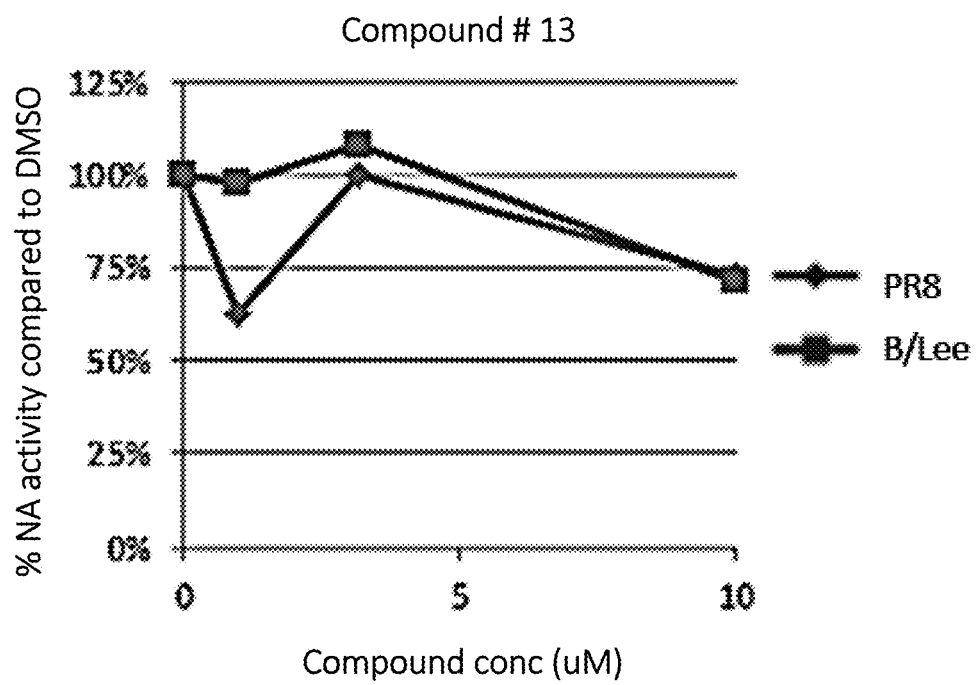
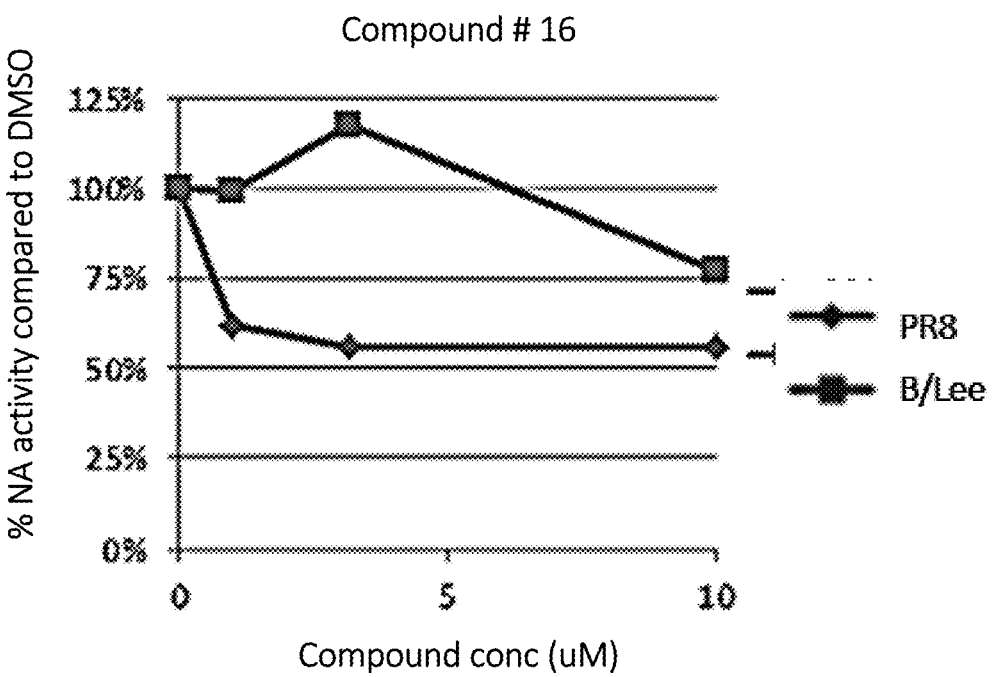

FIG. 21 – continued
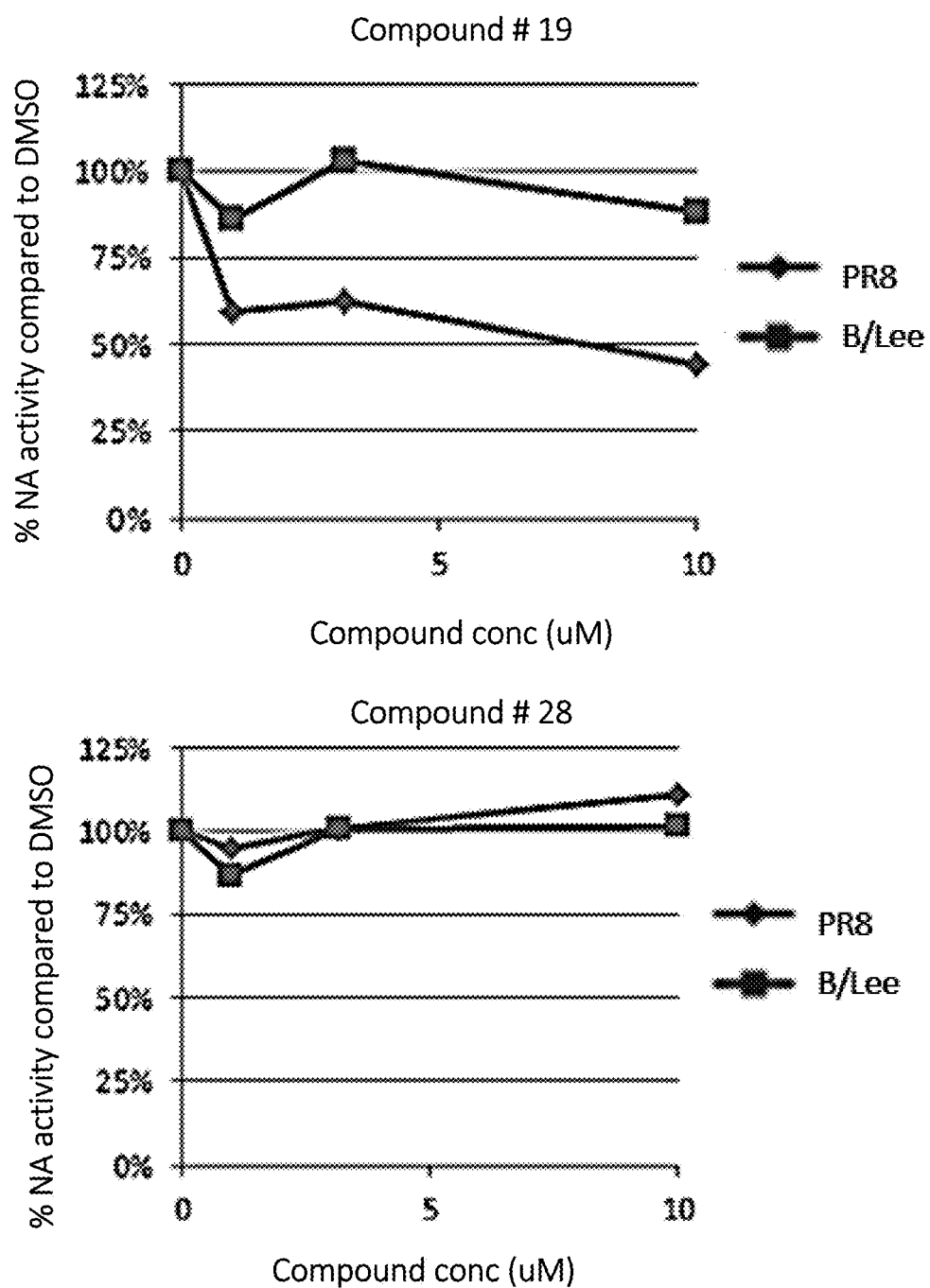

FIG. 21 – continued
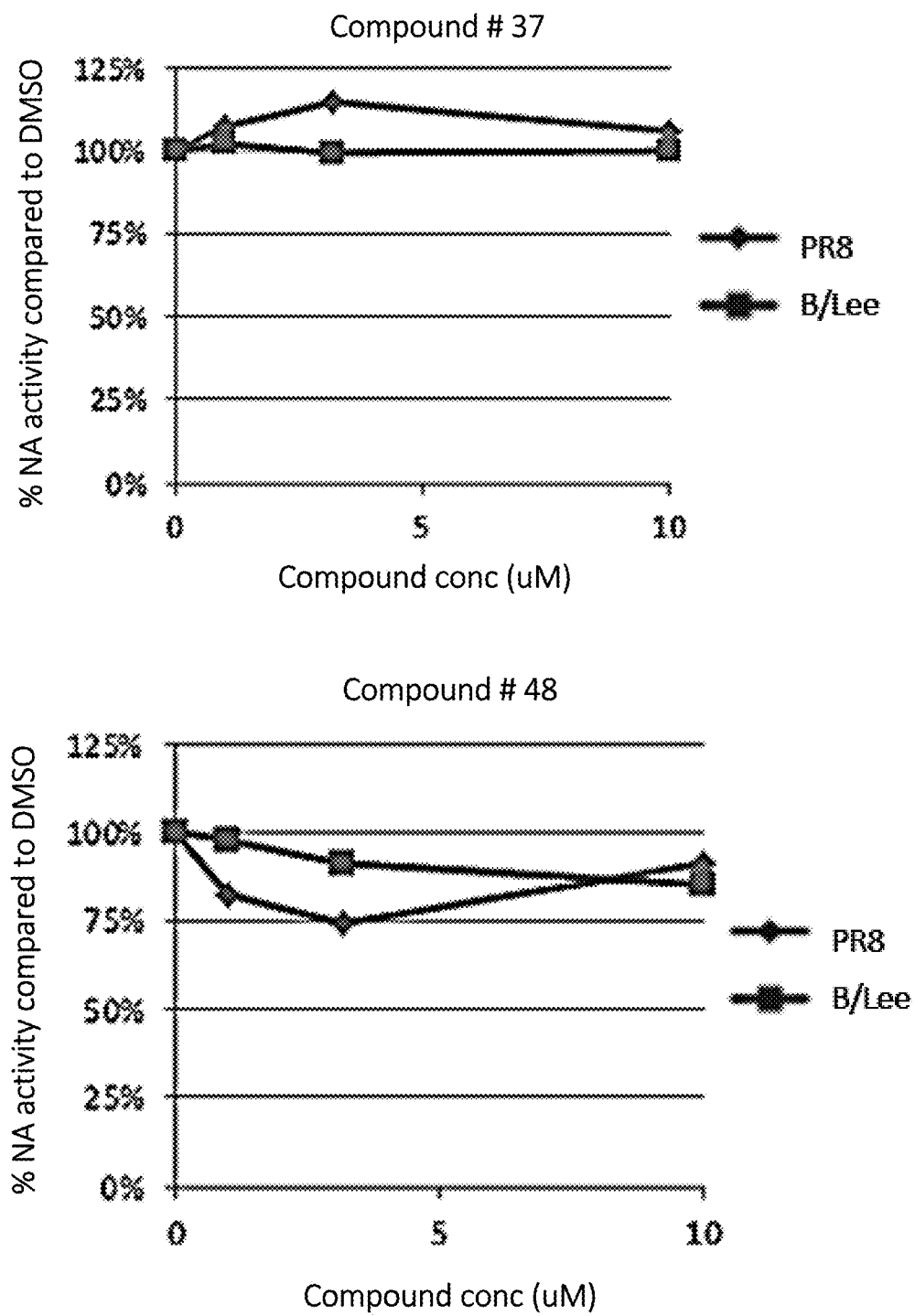

FIG. 21 – continued
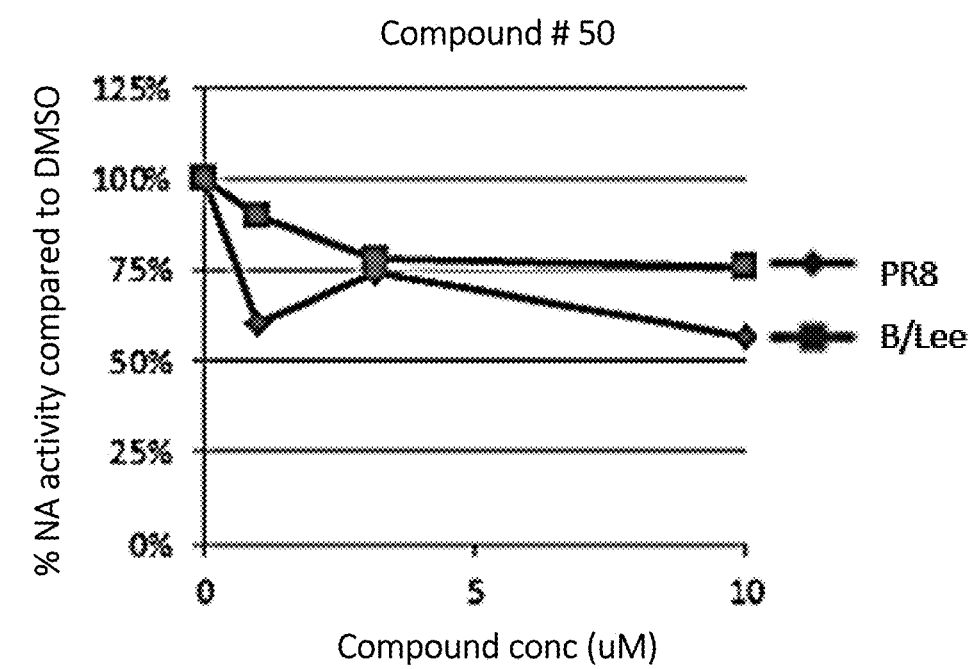
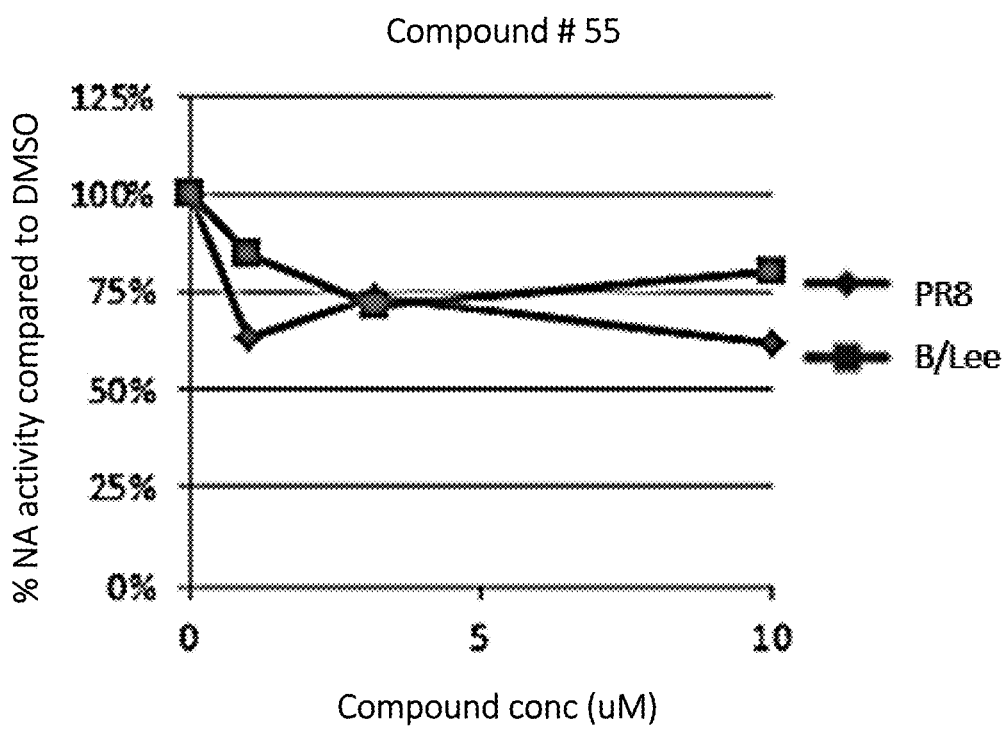

FIG. 22
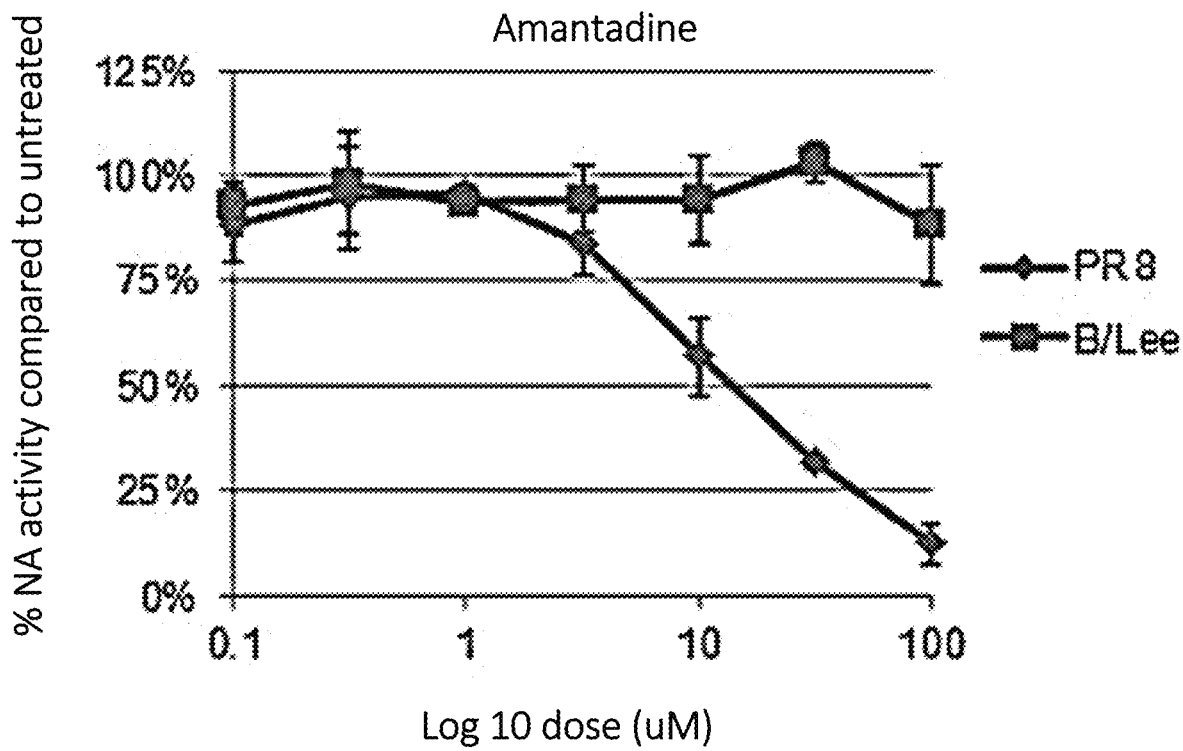
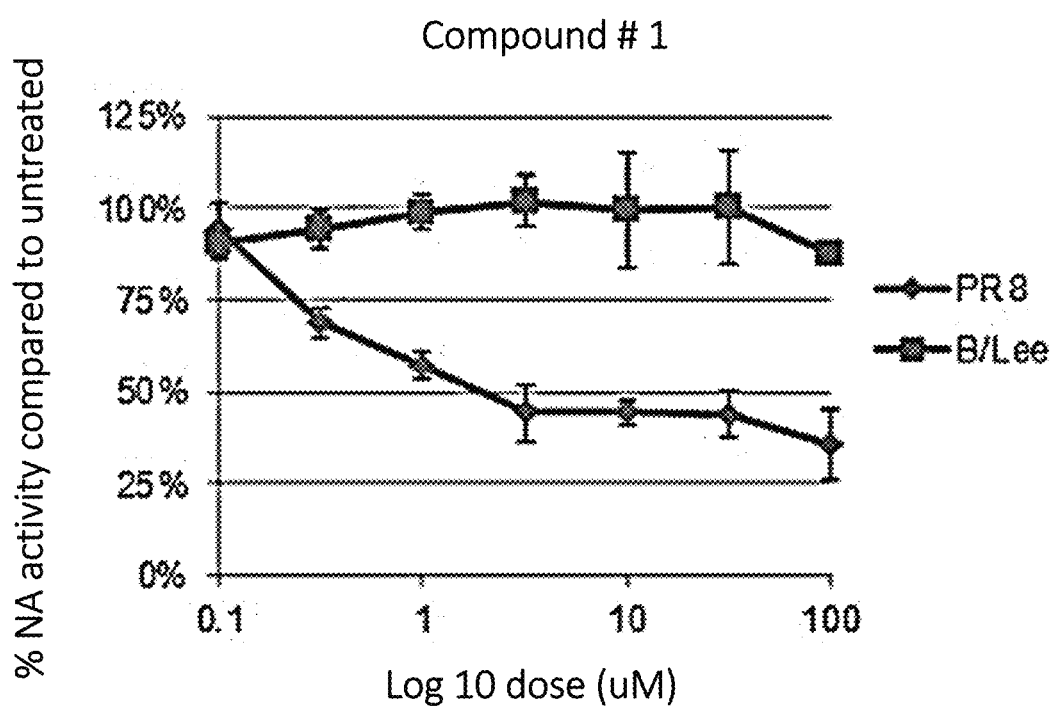

FIG. 22 - continued
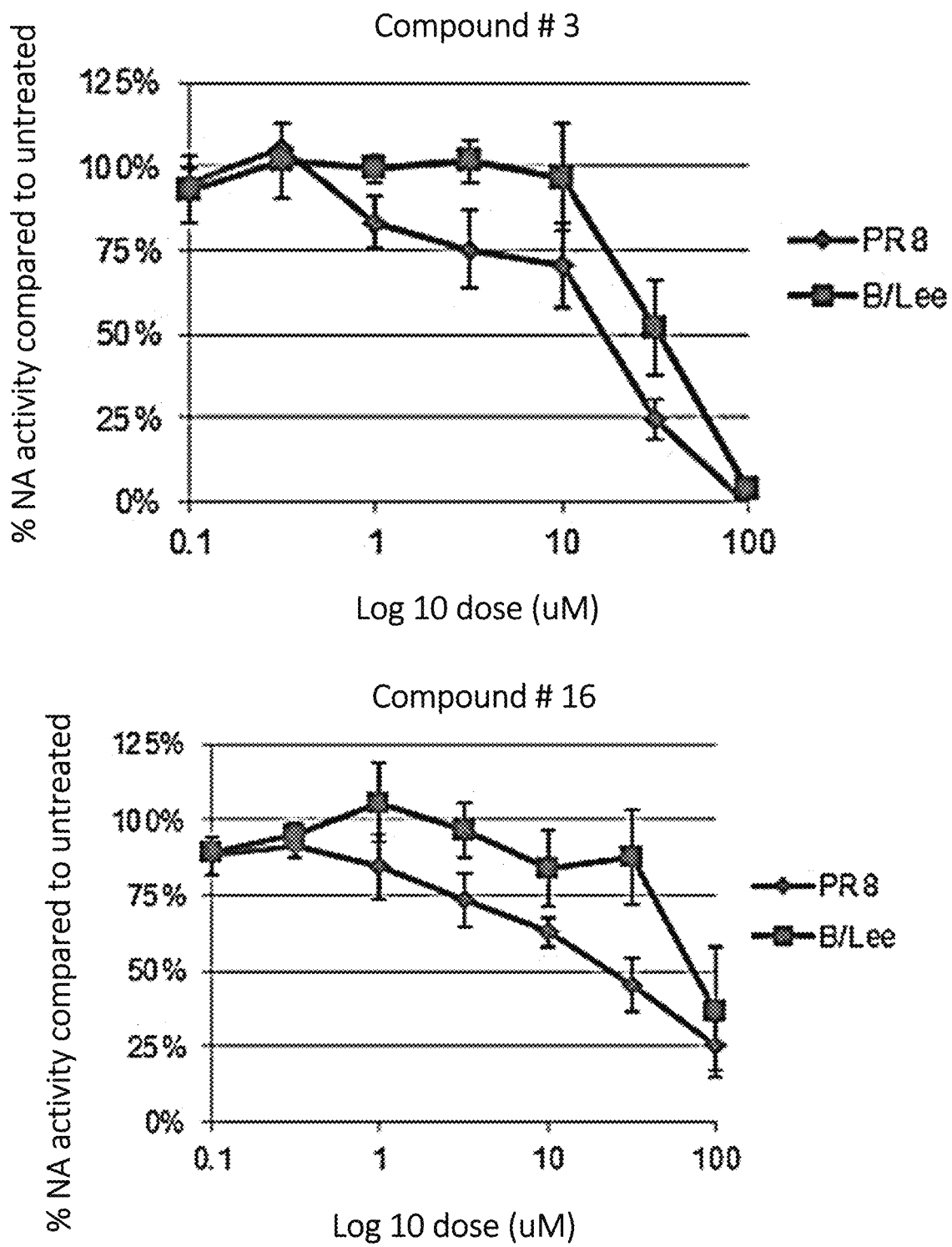

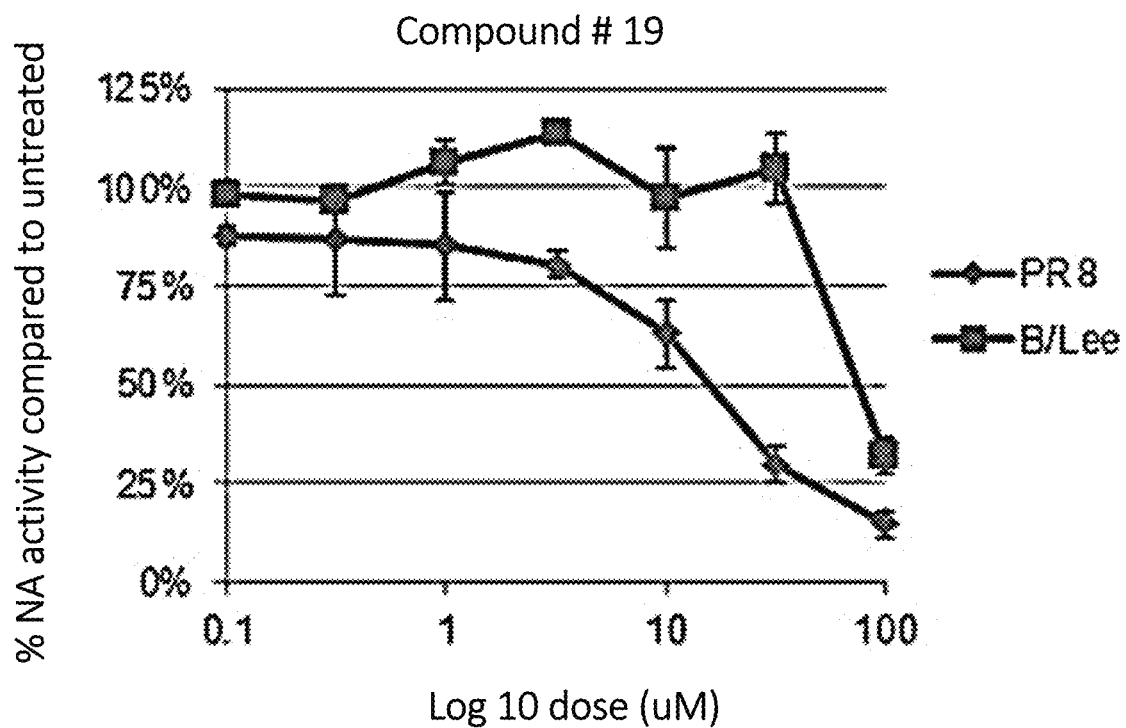
FIG. 22 – continued

FIG. 25

Influenza viruses used in assays

PR8

M2 sequence:
MSLLTEVETPIRNEWGCRCNGSSDPLAIAANII
GILHLTLWILDRLFFKCIYRRFKY

FIG. 26
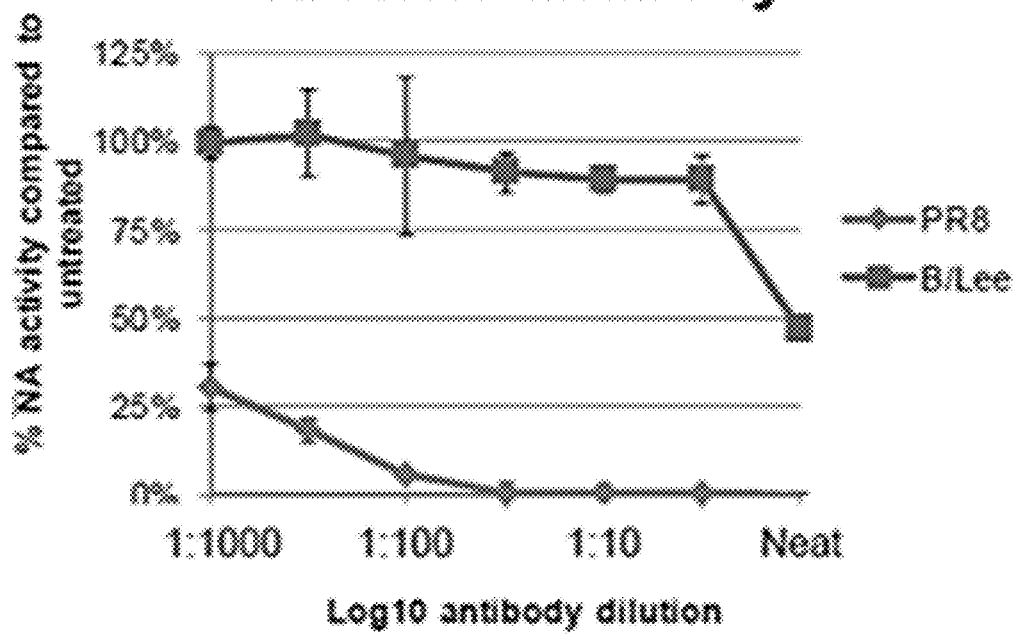
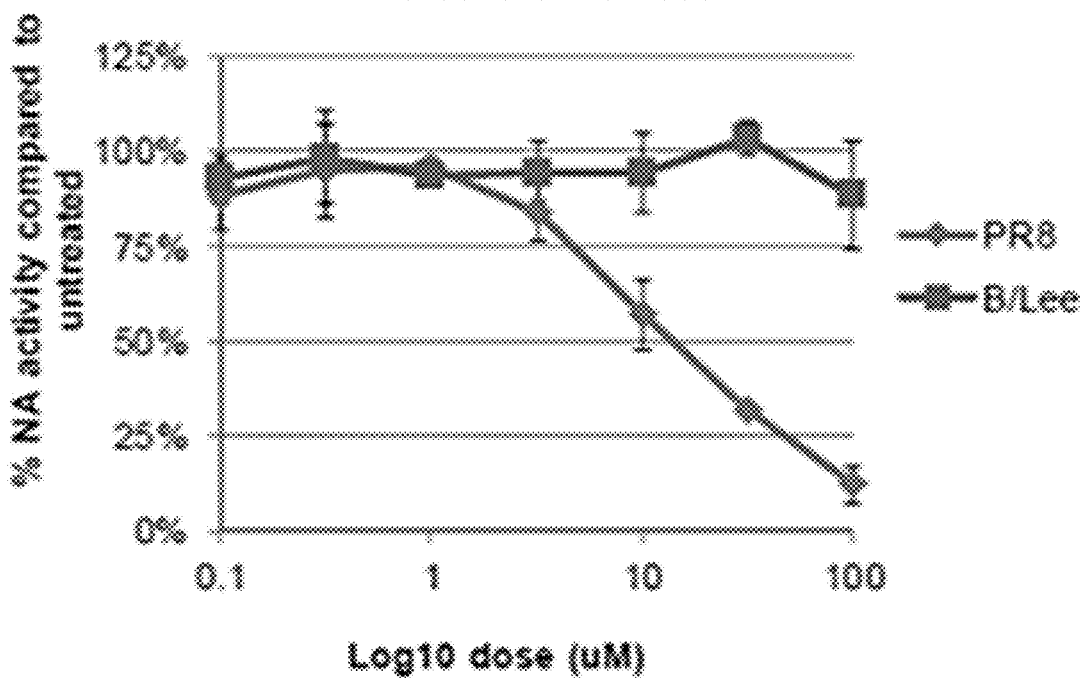

ANTIVIRAL AGENTS FOR DRUG-RESISTANT INFLUENZA A

CROSS-REFERENCE TO RELATED APPLICATIONS

This application is a continuation of U.S. application Ser. No. 16/062,253, filed Jun. 14, 2018, which is a U.S. National Stage Application of International Application No. PCT/US16/67470, filed Dec. 19, 2016, which claims the benefit of U.S. Provisional Application No. 62/268,802, filed Dec. 17, 2015, which is hereby incorporated by reference in its entirety.

FIELD OF INVENTION

The FDA approved drug amantadine (Symmetrel) was approved in 1966 as an antiviral for treatment of influenza A infections. Since then, it has also received approval for anti-parkinson activity. In the 1960's many common strains of influenza A were sensitive to amantadine. However, today approximately 97-100% of seasonal influenza A strains (including the most common H1N1 and H3N2) are resistant to amantadine. This is due to a specific mutation S31N in the M2 channel of influenza A that renders the virus resistant to amantadine.

Today, severe acute cases of influenza A are the largest number of influenza related hospitalizations on a yearly basis. Each year approximately 200,000 patients are hospitalized with influenza-related illnesses, resulting in thousands of deaths. As mentioned previously nearly 97-100% of these infections are resistant to amantadine. The primary drug treatment for these hospitalized patients is treatment with neuraminidase inhibitors such as oseltamivir (Tamiflu). However, each year there are increasing numbers of cases of resistance to neuraminidase inhibitors, making other therapeutic strategies of significant interest.

An effective therapeutic agent for the M2 channel (replacing amantadine) could be a very important therapeutic tool for the treatment of influenza A. This would allow treatment of neuraminidase-resistant strains as a single agent, and/or would also allow combination treatment (neuraminidase inhibitors with M2 channel inhibitors).

Certain patents and/or publications have previously described some of the compounds that are described herein. However, while these compounds have been previously determined to have pharmacological activity, these have not been previously indicated for antiviral activity against influence A. For example, U.S. Pat. No. 7,875,721 describes certain small molecules for binding to the estrogen receptor or GPR30, but not for antiviral activity. U.S. Pat. No. 7,049,468 is a related patent for the exact compound, but not for antiviral activity.

Further publications relate to compounds that are indicated for influenza A treatment and prevention including: U.S. Pat. Nos. 8,569,284 and 8,557,836. These patents provide compounds that are capable of modulating the activity of the influenza A virus via interaction with the M2 transmembrane protein.

Additionally, U.S. Pat. No. 8,440,720 (the '720 patent) relates, in part, to methods of treatment, prevention, and inhibition of viral disorders. In one aspect, the '720 patent relates to the inhibition of the M2 proton channel of influenza viruses (e.g. influenza A virus) and other similar viroporins (e.g., VP24 of Ebola and Marburg viruses; and NS3 protein of Bluetongue).

SUMMARY OF INVENTION

In one aspect of the present invention, there is provided a compound of Formula 1:

wherein $X_1$, $X_2$, $X_3$, $X_4$, $X_6$, $X_7$, and $X_8$ are independently a hydroxyl, methoxy, ethoxy, hydrogen, alkyl, alkenyl, alkynyl, cycloalkyl or aryl, F, Cl, or Br; and $X_5$ is a $CH_2OH$, hydroxyl, methoxy, ethoxy, hydrogen, alkyl, alkenyl, alkynyl, cycloalkyl or aryl, F, Cl, or Br; or a pharmaceutically acceptable salt therof, for use in the treatment of amantadine-resistant influenza A infections.

In one embodiment, a compound of Formula 1 is selected from the group consisting of 4-[5-(hydroxymethyl)-2-methyl-7-oxabicyclo[3.3.1]non-2-en-8-yl]phenol, [8-(4-methoxyphenyl)-2,4,9-trimethyl-7-oxabicyclo[3.3.1]non-en-5-yl]methanol, 4-(2,2,6-trimethyl-3-oxabicyclo[3.3.1] non-6-en-4-yl)phenol, and 4-[5-(hydroxymethyl)-2,4,9-trimethyl-7-oxabicyclo[3.3.1]non-2-en-8-yl]-2-methoxyphenol, for use in the treatment of amantadine-resistant influenza A infections.

A further aspect of the present invention includes a compound of Formula 2:

wherein $X_1$, $X_2$, $X_4$, $X_5$, $X_6$, $X_7$, $X_8$, $X_9$, $X_{10}$, $X_{11}$, and $X_{12}$ hydroxyl, methoxy, ethoxy, hydrogen, alkyl, alkenyl, alkynyl, cycloalkyl or aryl, F, Cl, or Br; and $X_3$ is a nitro, nitrile, carboxyl, ester, sulfonamide, methylsulfone, hydroxyl, methoxy, ethoxy, hydrogen, alkyl, alkenyl, alkynyl, cycloalkyl or aryl, F, Cl, or Br; or a pharmaceutially acceptable salt thereof, for use in the treatment of amantadine-resistant influenza A infections.

In one embodiment, a compound of Formula 2 is selected from the group consisting of N-benzyl-2,4,6-trimethylbenzenesulfonamide, 2,4,6-trimethyl-N-[(3-methylphenyl) methyl]benzenesulfonamide, N-[(2-chlorophenyl)methyl]-2,4,6 trimethylbenzenesulfonamide, 2,6-dimethyl-4-nitro-N-(pyridin-2-ylmethyl) benzenesulfonamide, and N-[(2-methoxyphenyl)methyl]-2,4,6 trimethylbenzenesulfonamide, for use in the treatment of amantadine-resistant influenza A infections.

In another embodiment a compound is selected from the group consisting of 2-(1-adamantyl)-N-(4-nitrophenyl)acetamide, 3,5-dimethyl-N-(4-nitrophenyl)adamantane-1-carboxamide, 2-(1-adamantyl)-N-(2-methyl-4-nitrophenyl)acetamide, 3-(4-nitrophenyl)adamantan-1-ol, 1-(4-nitrophenyl)adamantane, or a pharmaceutically acceptable salt of any of these compounds, for use in the treatment of amantadine-resistant influenza A infections.

A method of treating amantadine-resistant influenza A infections, said method comprising administering to an individual a pharmaceutical composition which comprises a theraputically effective amount of a compound described in Formula 1 or Formula 2, or a pharmaceutically acceptable salt therof.

Another aspect of the present invention provides a compound of formula:

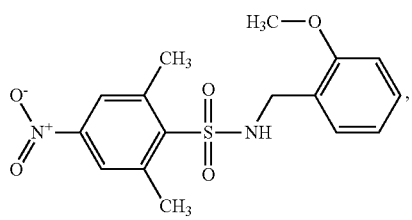

or a pharmaceutically acceptable salt thereof.

One embodiment provides a compound of formula:

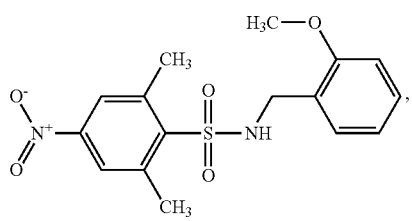 [SMILES: COc1ccccc1CNS(=O)(=O)c1c(C)cc([N+](=O)[O-])cc1C]

or a pharmaceutically acceptable salt thereof, for use as a medicament.

Another embodiment provides a compound of formula:

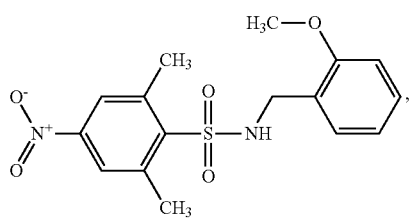

or a pharmaceutically acceptable salt thereof, for use in the treatment of amantadine-resistant influenza A infections.

In yet another embodiment, a pharmaceutical composition comprises a compound of formula:

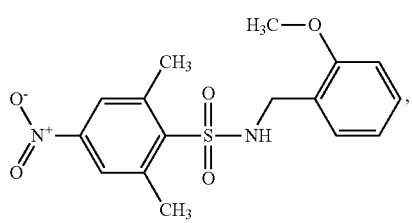

or a pharmaceutically acceptable salt thereof, and a pharmaceutically acceptable diluent or carrier.

Another aspect of the present invention provides a compound of formula:

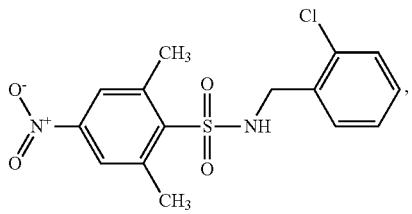 [SMILES: Cc1cc([N+](=O)[O-])cc(C)c1S(=O)(=O)NCc1ccccc1Cl]

or a pharmaceutically acceptable salt thereof.

One embodiment provides a compound of formula:

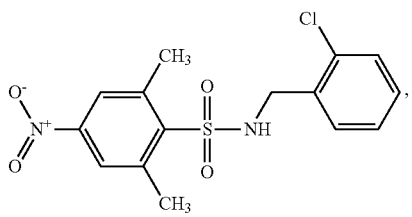 [SMILES: Cc1cc([N+](=O)[O-])cc(C)c1S(=O)(=O)NCc1ccccc1Cl]

or a pharmaceutically acceptable salt thereof, for use as a medicament.

Another embodiment provides a compound of formula:

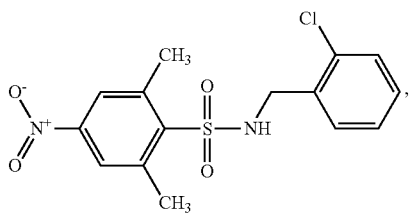 [SMILES: Cc1cc([N+](=O)[O-])cc(C)c1S(=O)(=O)NCc1ccccc1Cl]

or a pharmaceutically acceptable salt thereof, for use in the treatment of amantadine-resistant influenza A infections.

In yet another embodiment, a pharmaceutical composition comprises a compound of formula:

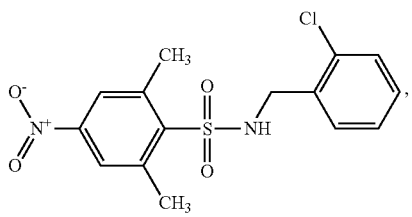 [SMILES: Cc1cc([N+](=O)[O-])cc(C)c1S(=O)(=O)NCc1ccccc1Cl]

or a pharmaceutically acceptable salt thereof, and a pharmaceutically acceptable diluent or carrier.

Another aspect of the present invention provides a method of producing an antiviral effect in a patient, which comprises administering to the patient an effective amount of a compound of formula:

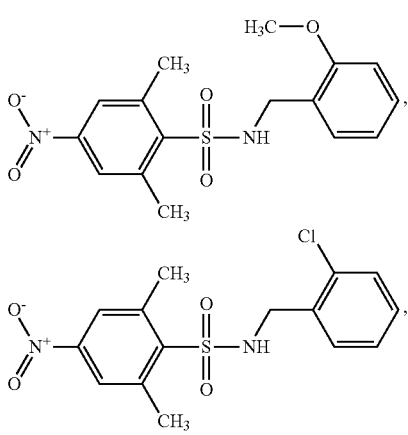

or a pharmaceutically acceptable salt of either compound.

BRIEF DESCRIPTION OF THE DRAWINGS

FIG. 1 depicts a chart identifying compounds and analogs and their activity.

FIGS. 2 A-B demonstrates antiviral activity for the PR8 strain but not the B/Lee Strain for oxabicyclo class compound 1 and analogs 2, 4, and 5.

FIGS. 3 A-B shows antiviral activity for the PR8 strain but not the B/Lee Strain for sulfonamide class compound 3 and analogs 7, 11, and 31.

FIG. 21 shows a series of promising compound hits from the virtual docking screening using the in vitro 4-MUNANA assay described above. The compounds were first tested in half-log dilutions at concentrations ranging from 1-10 uM alongside DMSO (as a negative control) and amantadine (as a partial positive control). The fluorescence values were normalized to the DMSO control. Four compounds (1, 3, 16, and 19) showed selective activity against PR8 strain.

FIG. 22 demonstrates the same in vitro 4-MUNANA assay for the four compounds (1, 3, 16, and 19) but with a larger concentration range of 0.1-100 uM.

FIG. 23A shows the results of an initial experiment that confirms that compounds 1, 3, 16, and 19 provide neuraminidase inhibition via interaction with the M2 channel. FIG. 23B shows that compound 3, analog 7, analog 31, JDB-0120, and JDB-0121 also provide neuraminidase inhibition via interaction with the M2 channel.

Figure 25:
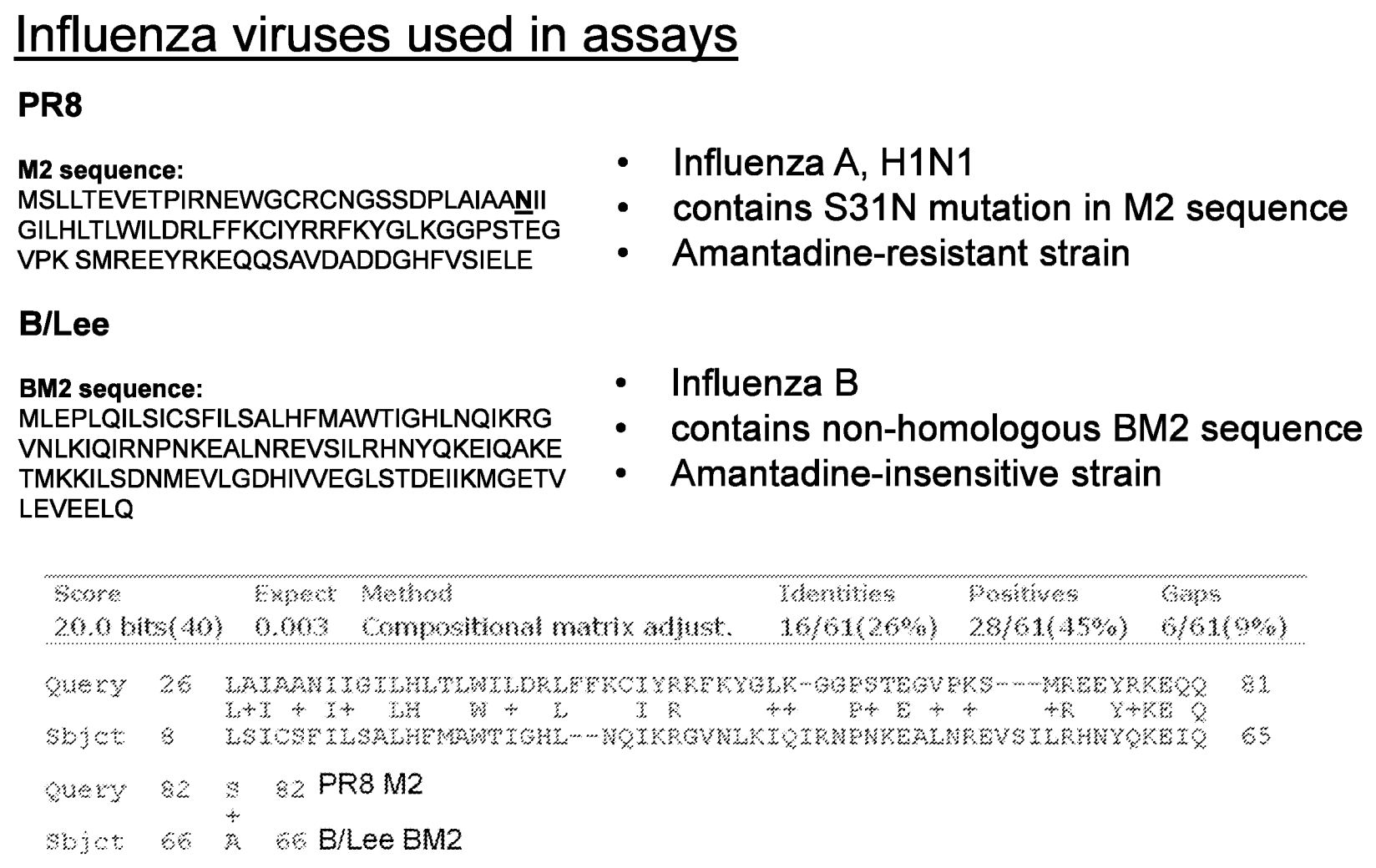

FIG. 25 describes the influenza strains that were selected to test for M2 channel activity. PR8 influenza A H1N1 strain contains the amantadine resistant S31N mutation in the M2 channel sequence. The B/Lee Influenza B strain is not sensitive to amantadine as it does not contain the M2 channel. Compounds within the scope of the present invention exhibit no effect on the B/Lee Influenza B strain as it does not contain the M2 channel.

FIG. 26 this figure depicts assay controls for the assays with the PR8 and B/Lee strains of the virus. The anti-H1 antibody blocked infection and replication of the PR8 virus with no effect on B/Lee as expected. Amantadine was found to moderately inhibit the replication of the PR8 strain as expected while having no effect on the B/Lee strain.

DETAILED DESCRIPTION

Figure 4A:
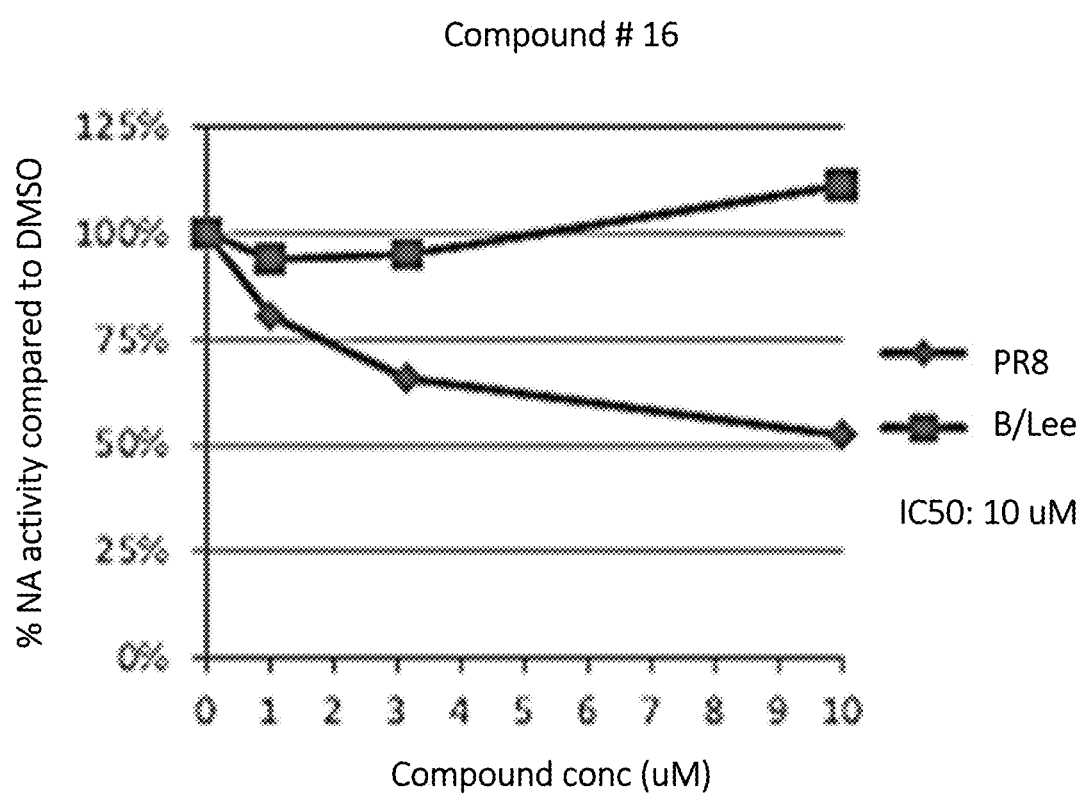
FIGS. 4 A-C demonstrates antiviral activity for the PR8 strain but not the B/Lee Strain for compound 16 and analogs 18 and 21.
Figure 4C:
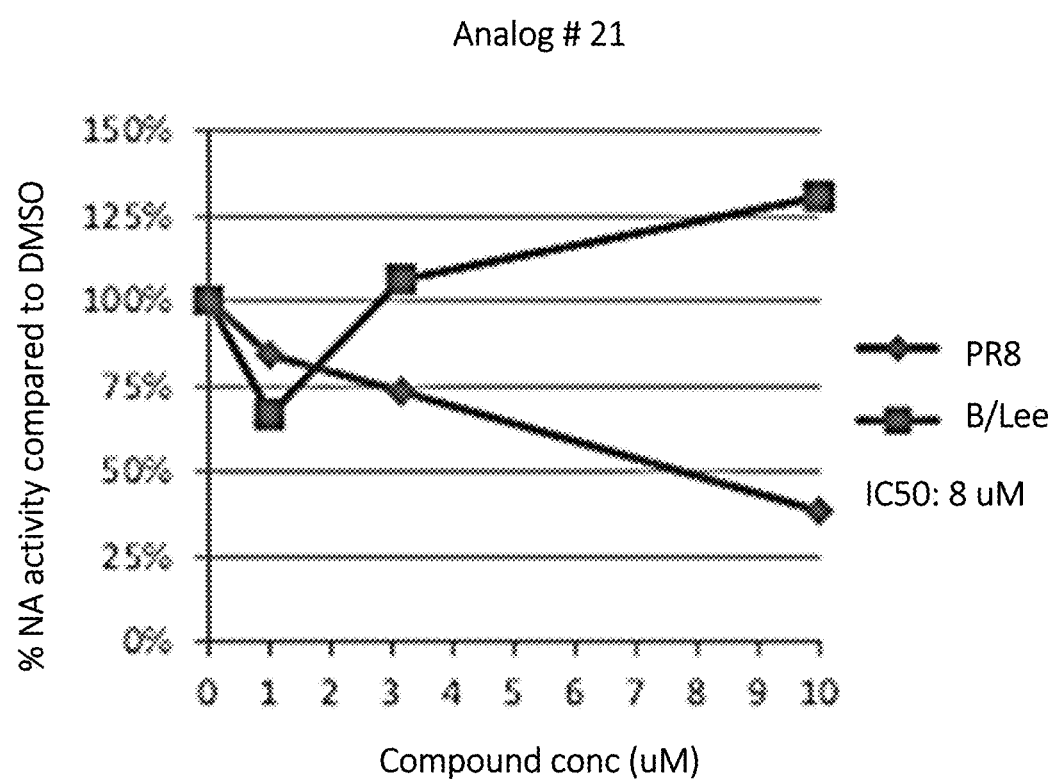
Figure 5B:
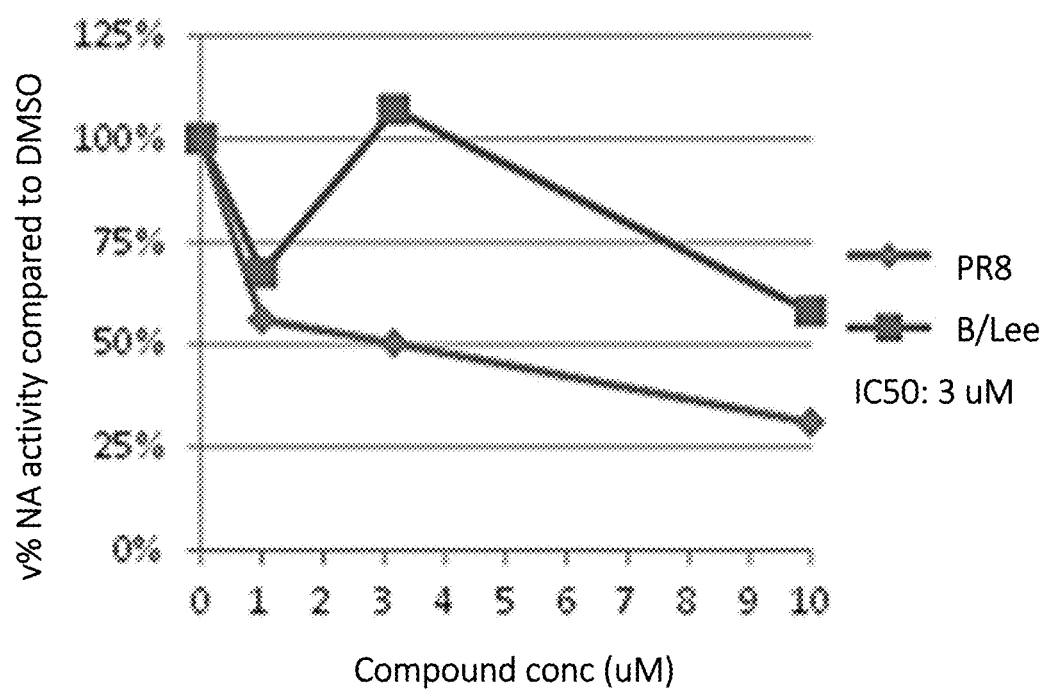
FIG. 5 A-B shows antiviral activity for the PR8 strain but not the B/Lee Strain for compound 19 and analog 23.
Figure 6A:
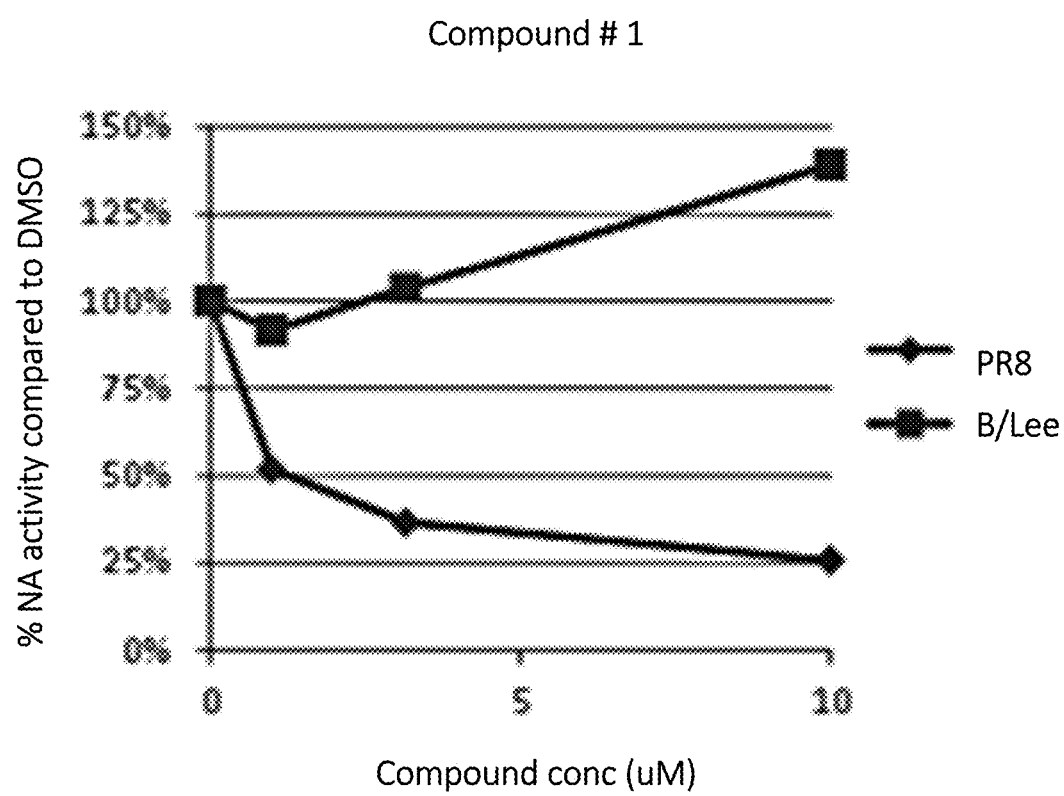
FIGS. 6 A-B demonstrates antiviral activity for the PR8 strain but not the B/Lee Strain for oxabicyclo class compound 1 and analogs 1 through 5, where analogs 2, 4, and 5 were shown to have more potent antiviral activity.
Figure 6B:
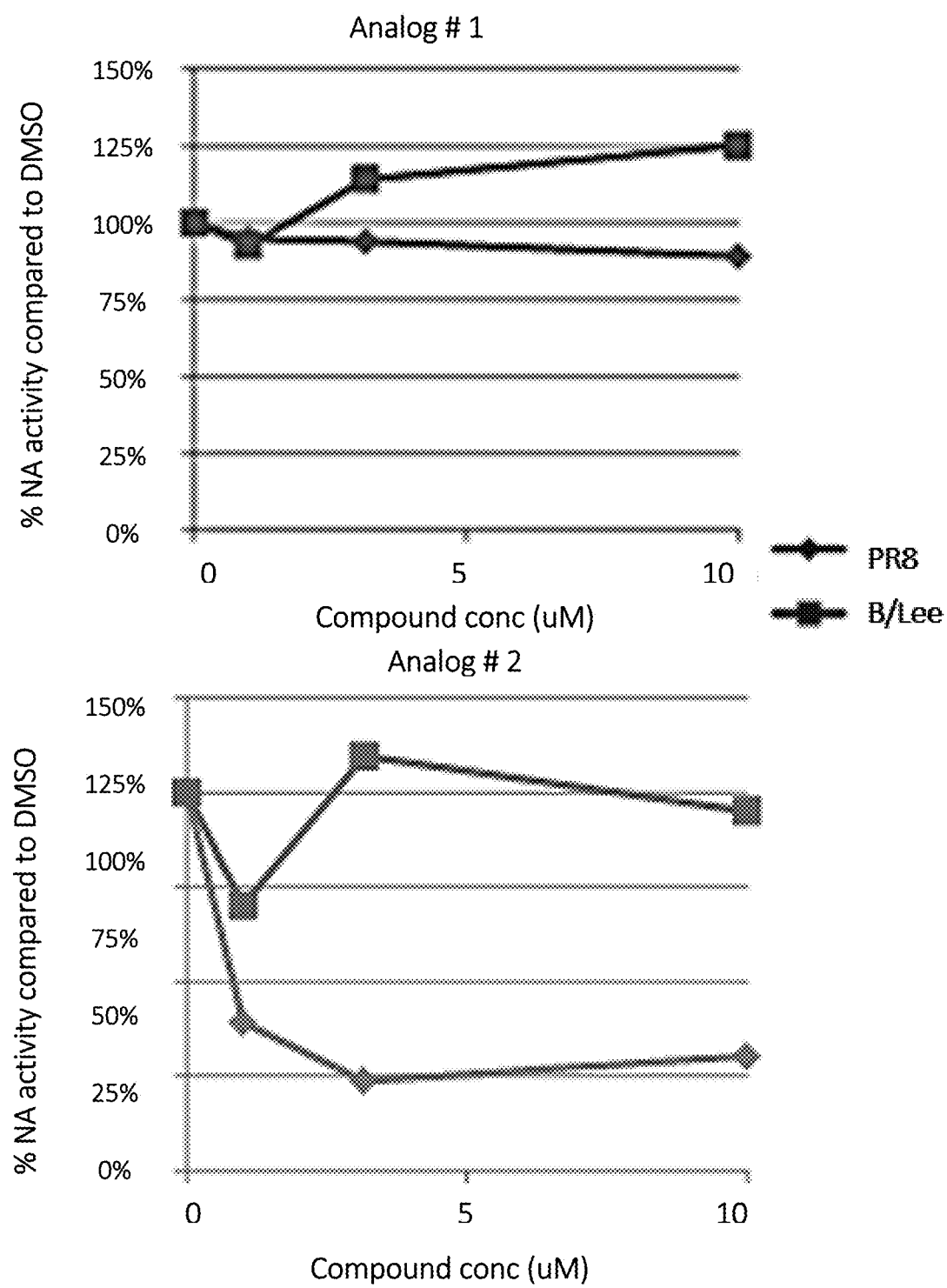
Figure 7A:
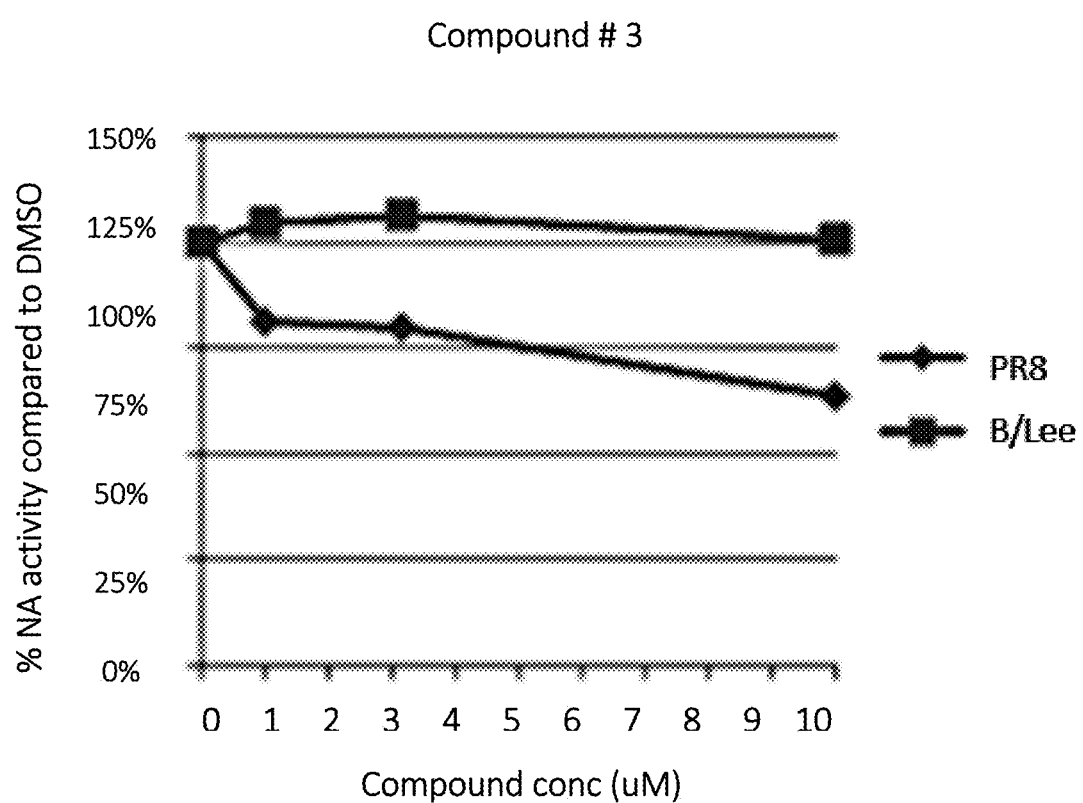
FIGS. 7 A-B shows antiviral activity for the PR8 strain but not the B/Lee Strain for sulfonamide class compound 3 and analogs 6 through 10, where analog 7 was shown to have more potent antiviral activity.
Figure 8:
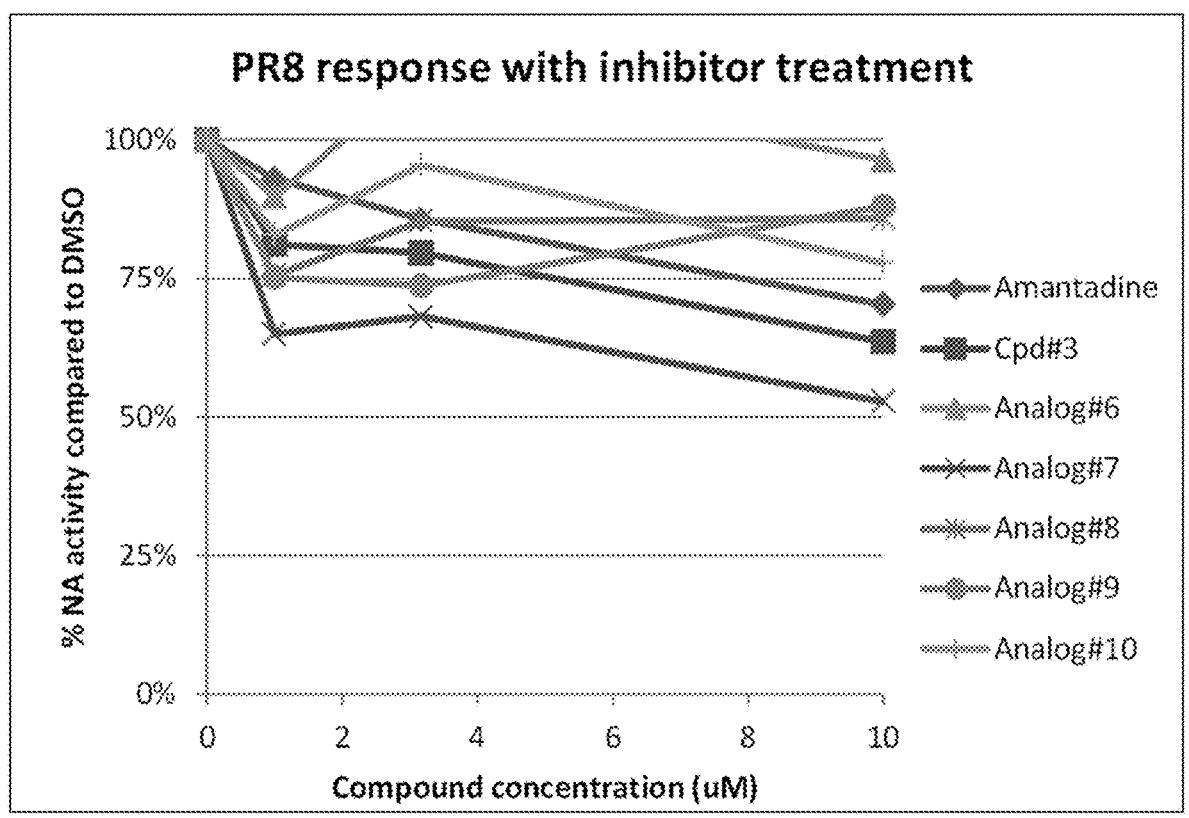
FIG. 8 shows antiviral activity for the PR8 strain for sulfonamide class compounds compared to amantadine, where compound 3 and analog 7 are more potent than amantadine.
Figure 9:
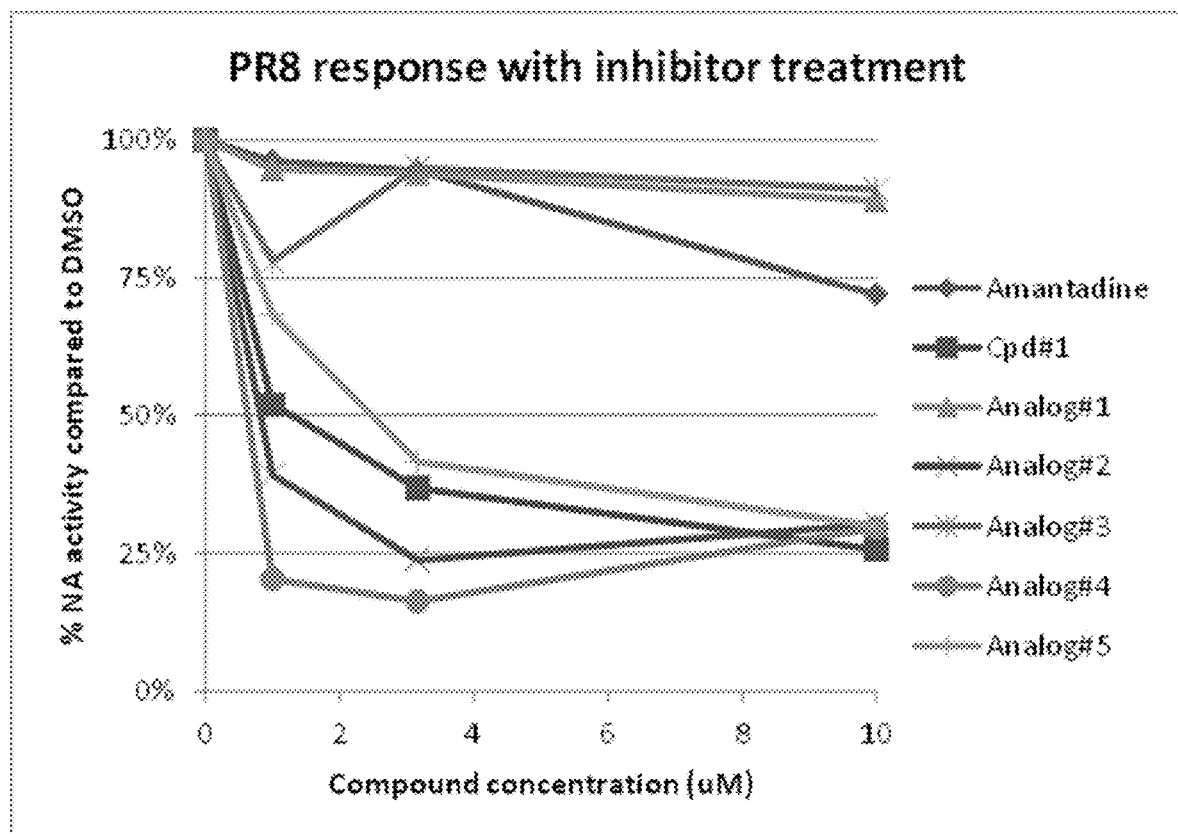
FIG. 9 illustrates antiviral activity for the PR8 strain for oxabicyclo class compounds 1 thru 4 compared to amantadine where analog 4 is the most potent.
Figure 10A:
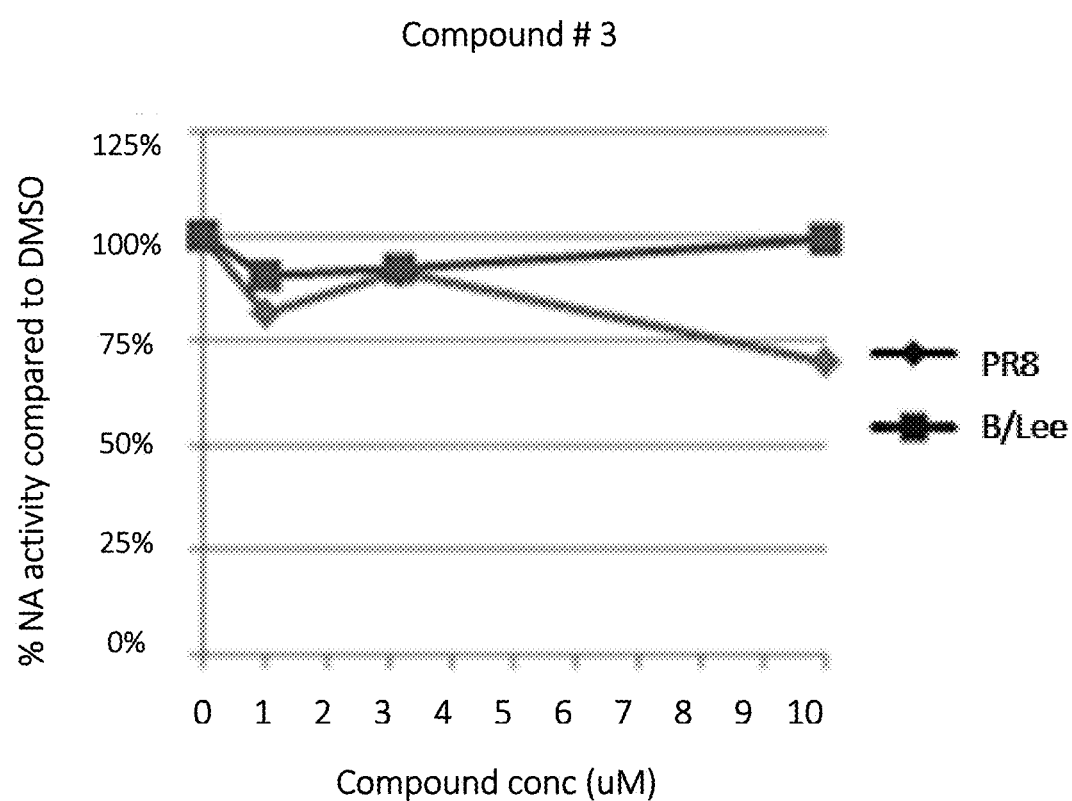
FIGS. 10 A-B shows antiviral activity for the PR8 strain but not the B/Lee Strain of several sulfonamide class compounds where analog 11 is the most potent.
Figure 11:
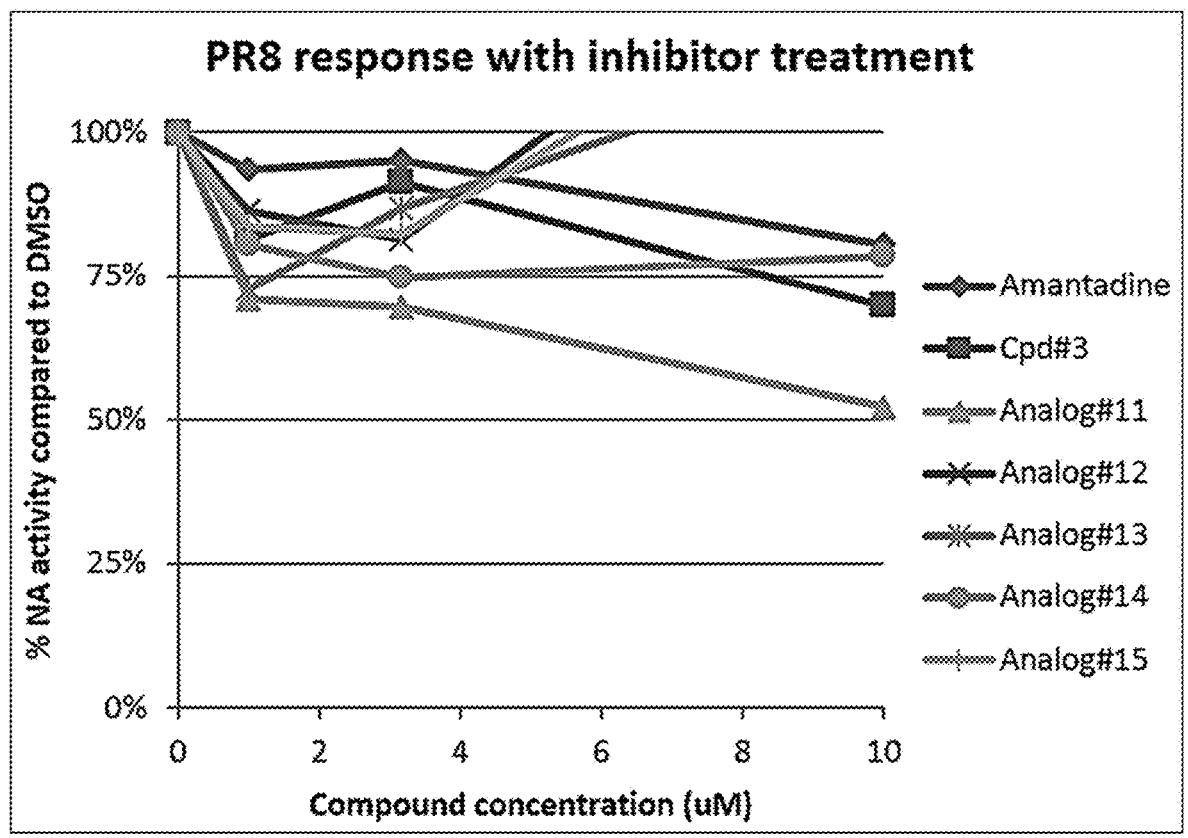
FIG. 11 shows antiviral activity for the PR8 strain for sulfonamide class compounds compared to amantadine, where analog 11 is the most potent.
Figure 12:
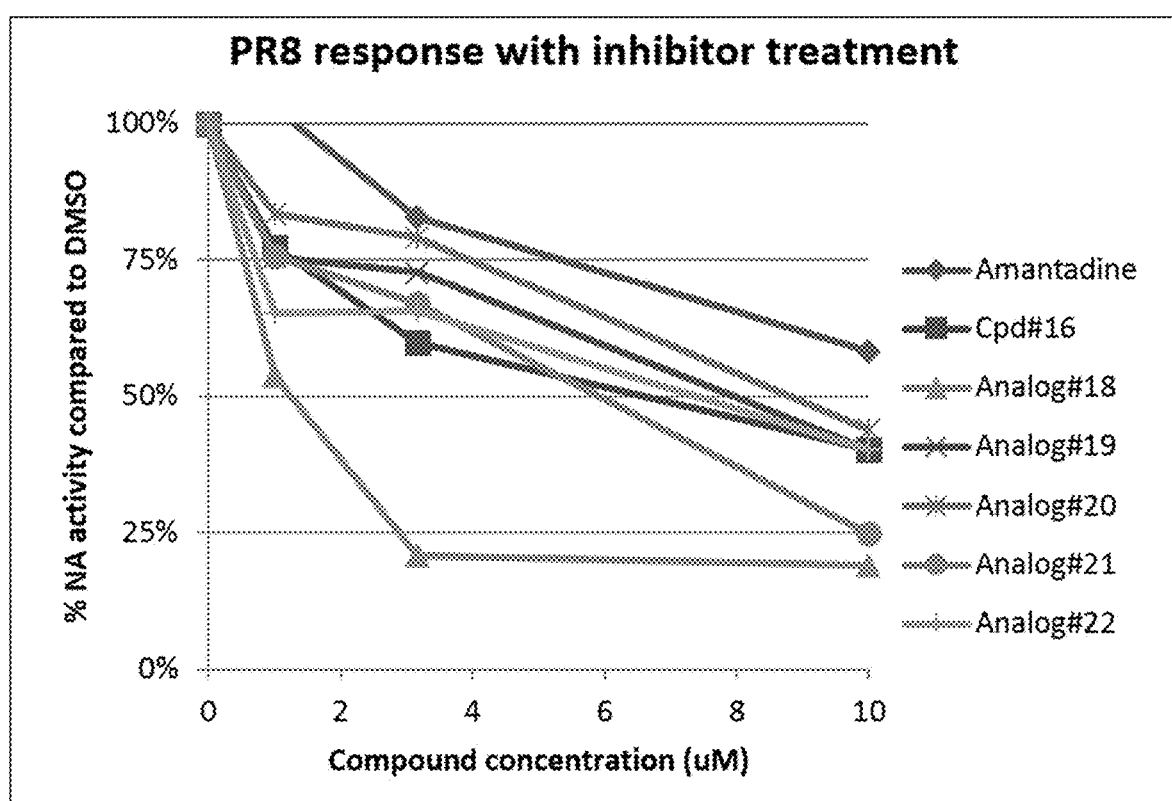
FIG. 12 depicts antiviral activity for the PR8 strain for several compounds compared to amantadine where analog 18 is the most potent.
Figure 13A:
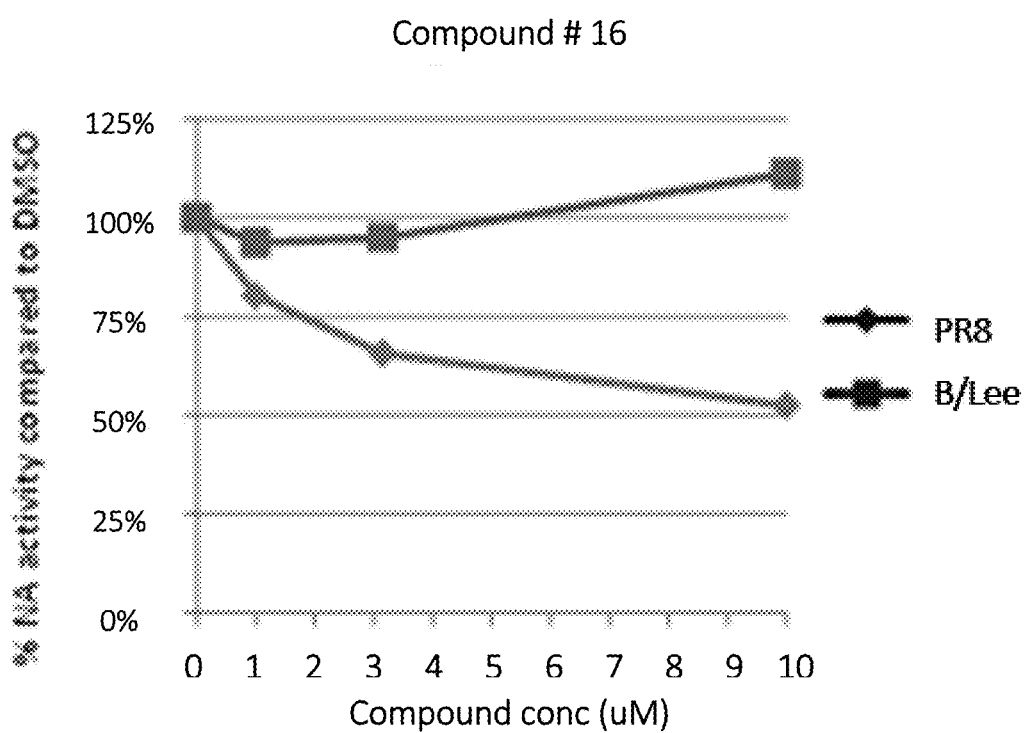
FIGS. 13 A-F demonstrates antiviral activity for the PR8 strain but not the B/Lee Strain for several compounds where analog 18 is the most potent.
Figure 13B:
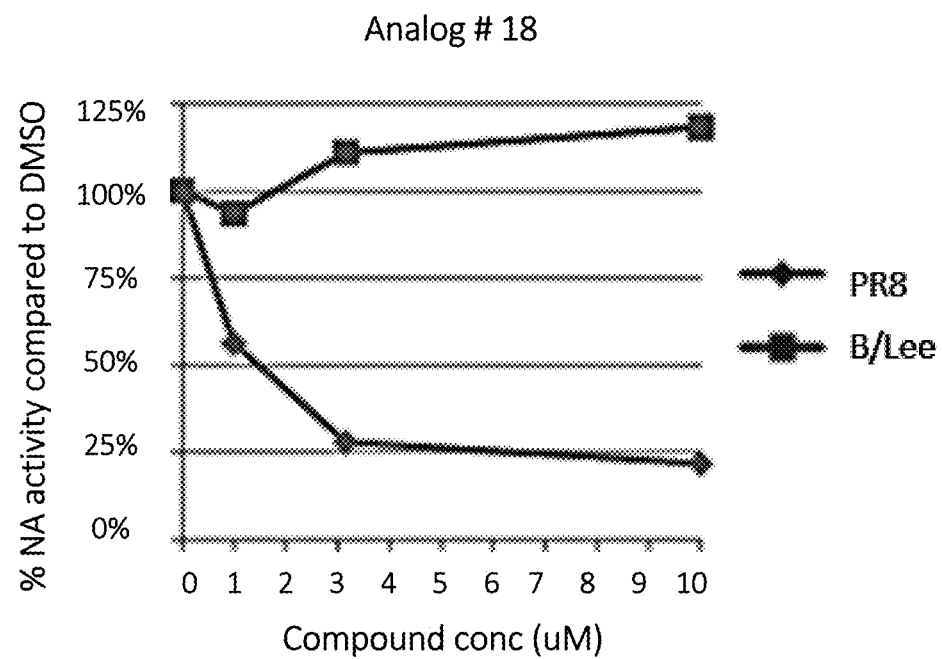
Figure 13C:
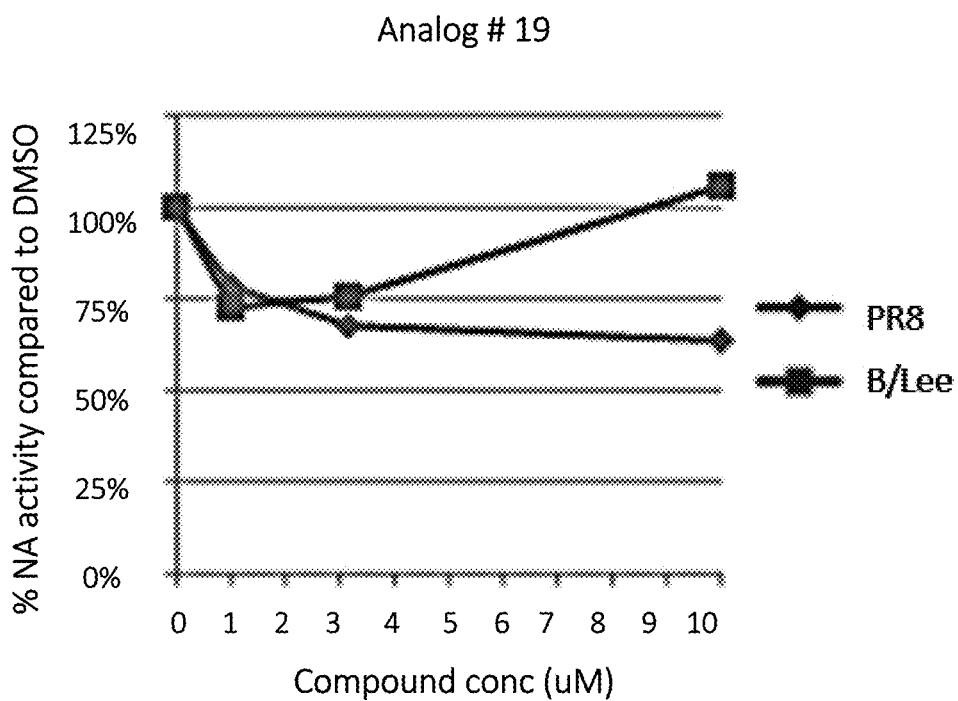
Figure 13D:
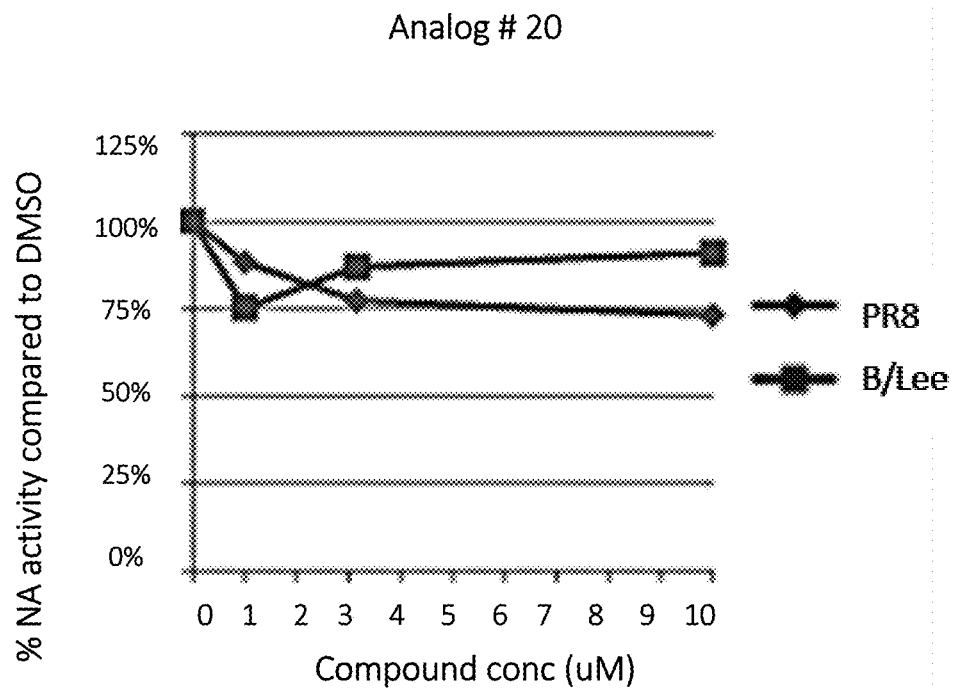
Figure 13E:
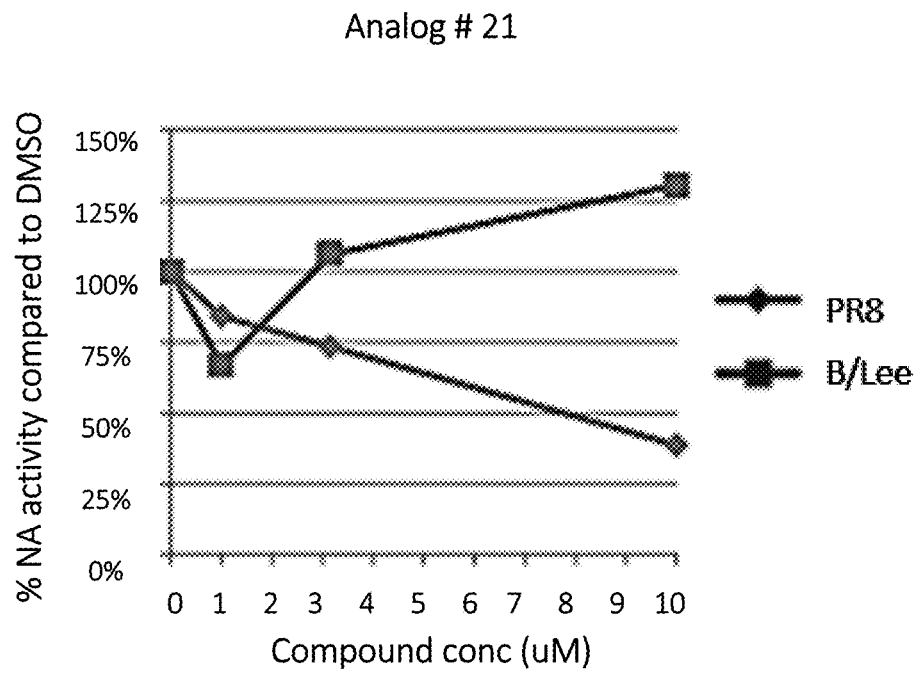
Figure 13F:
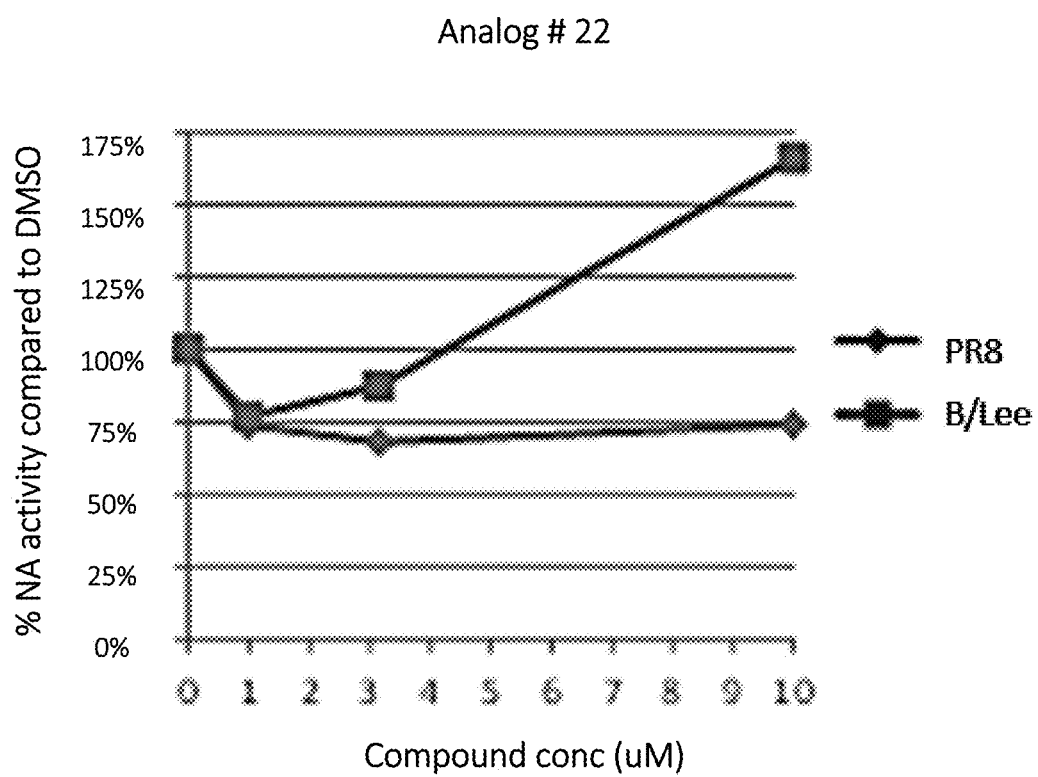
Figure 14:
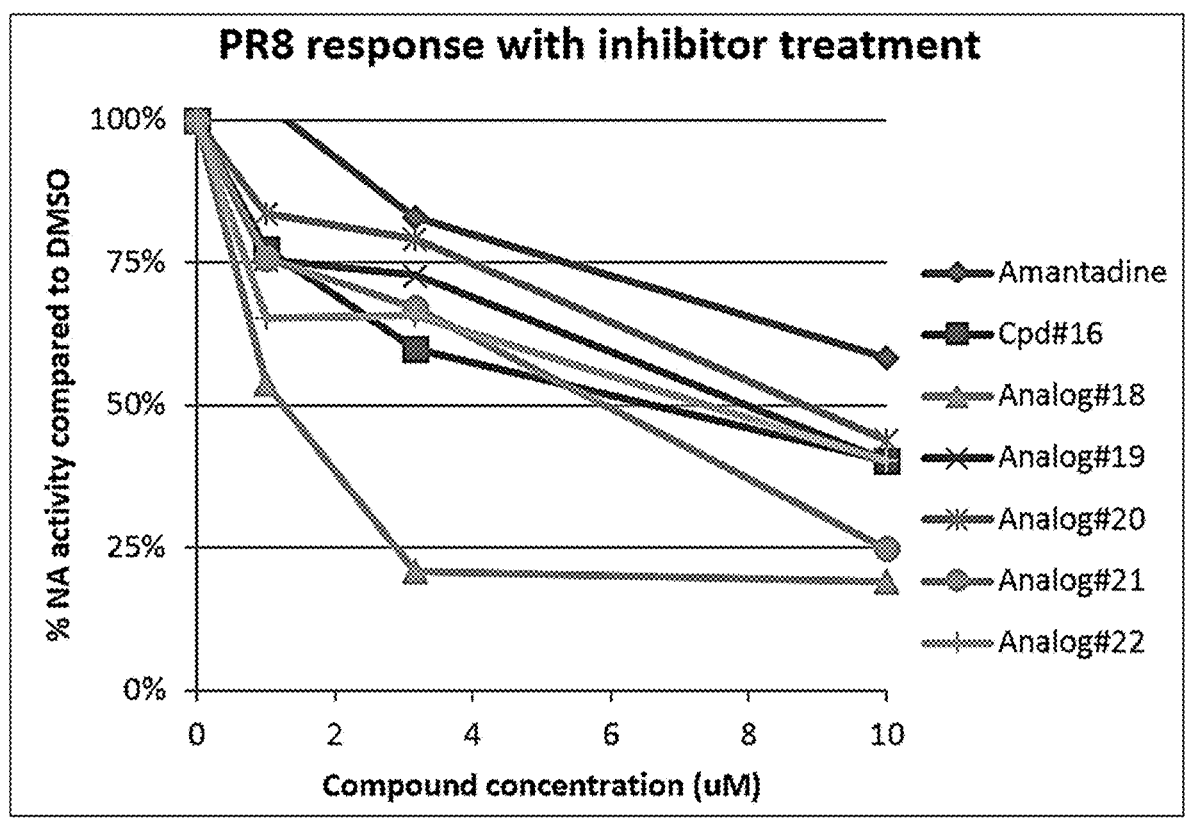
FIG. 14 shows antiviral activity for the PR8 strain for sulfonamide class compounds that do not have activity as compared to analog 18 provides insight into structure activity relationship.
Figure 15A:
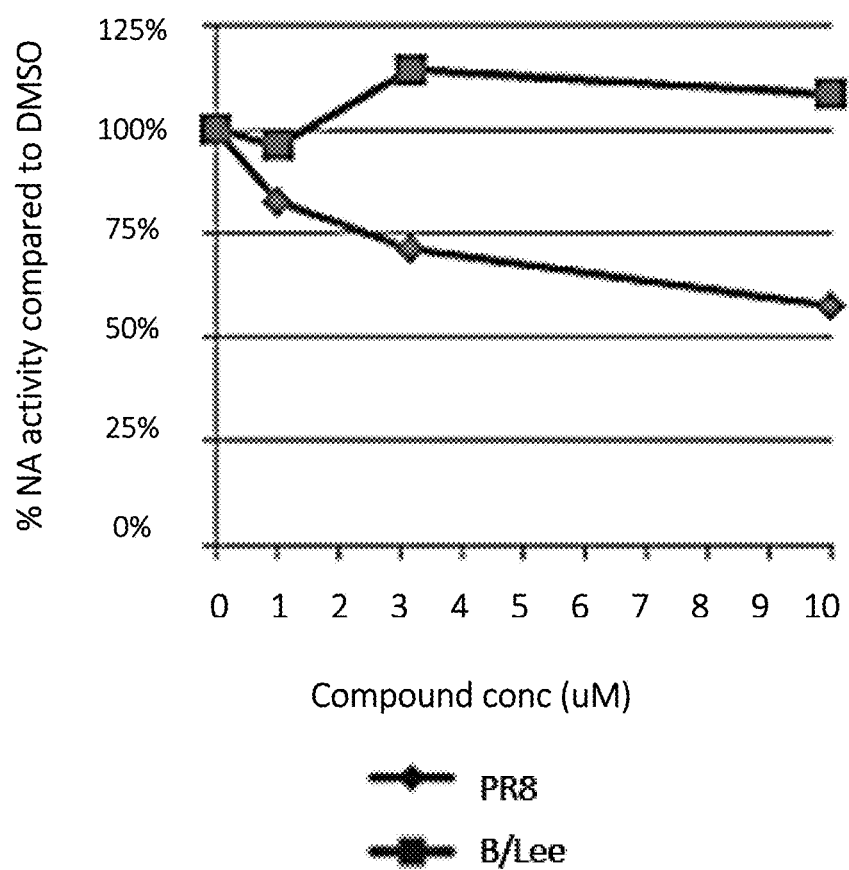
FIGS. 15 A-B illustrates antiviral activity for the PR8 strain but not the B/Lee Strain for sulfonamide class compounds that exhibit weaker activity than compound 3.
Figure 15B:
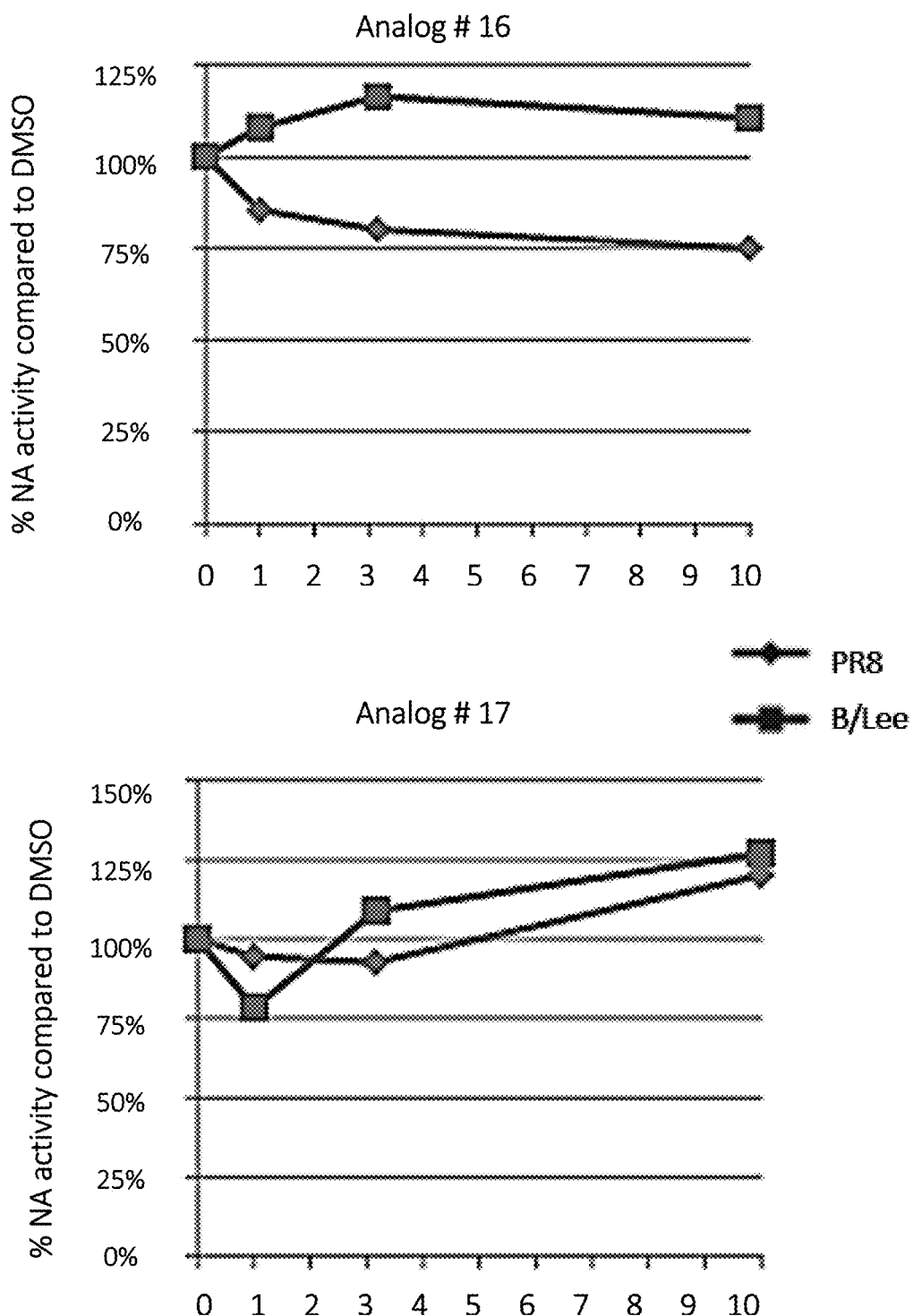
Figure 16A:
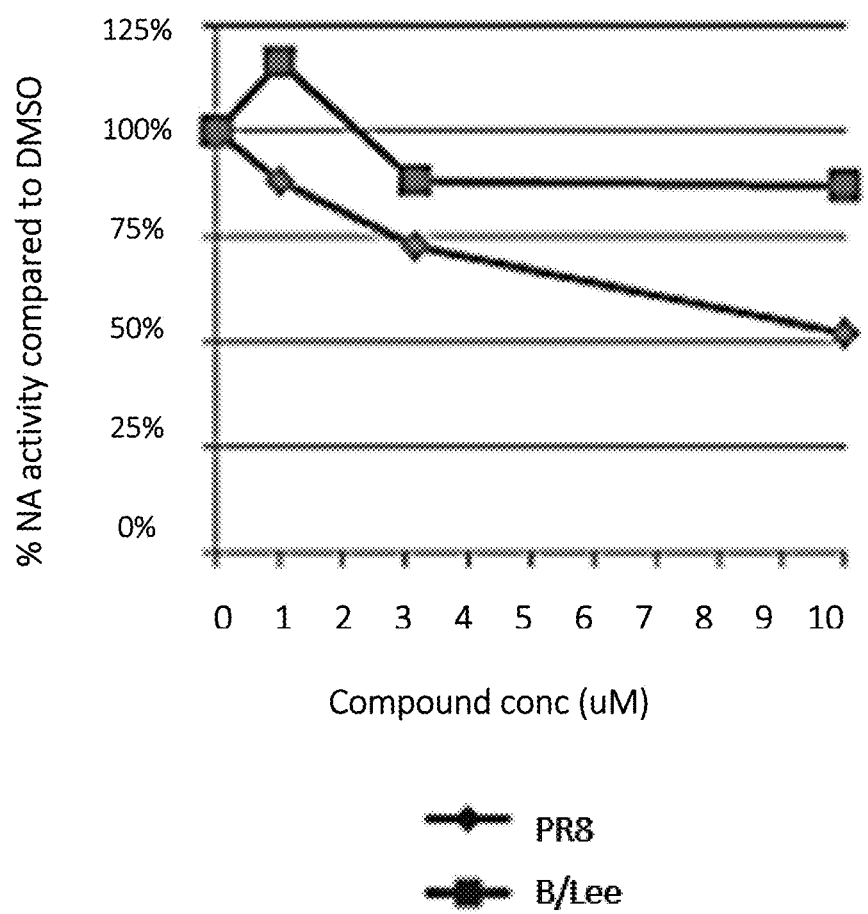
FIGS. 16 A-B shows antiviral activity for the PR8 strain but not the B/Lee Strain for sulfonamide class compounds that exhibit weaker activity than compound 3 and analog 31.
Figure 17:
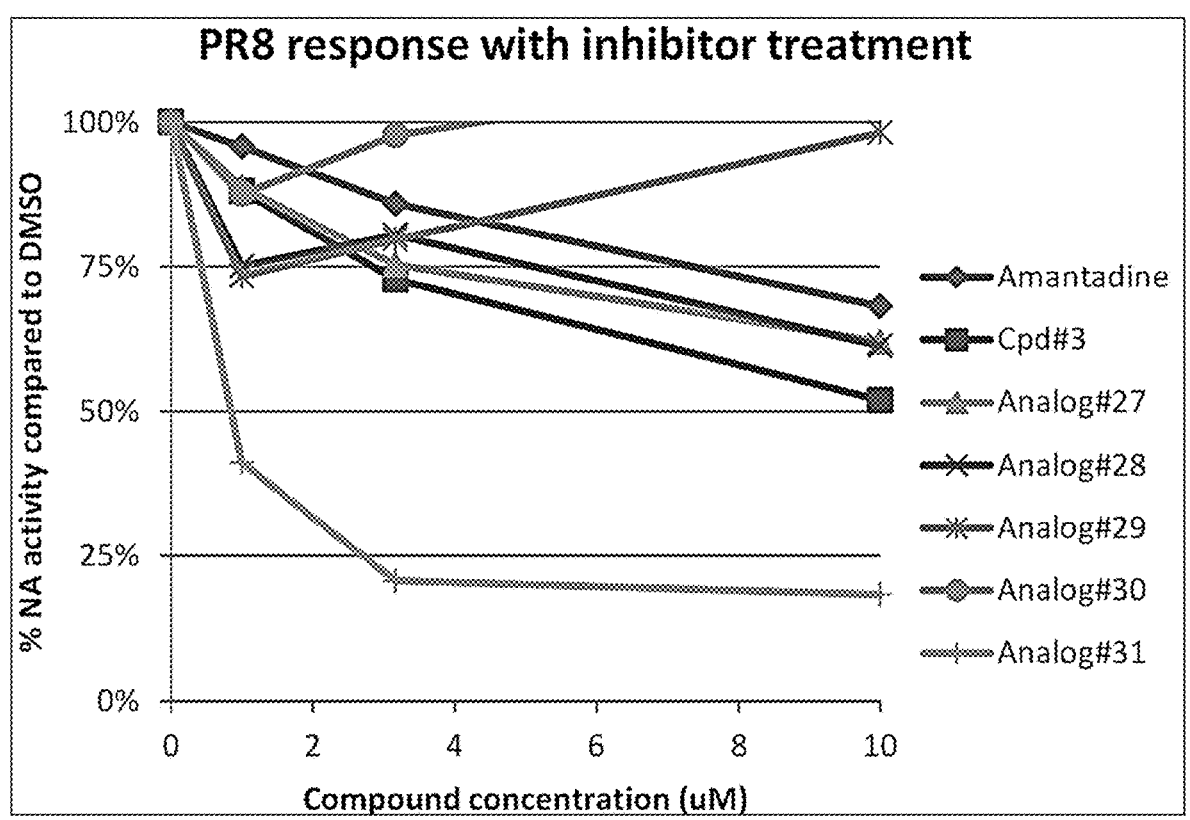
FIG. 17 demonstrates antiviral activity for the PR8 strain for sulfonamide class compounds compared to amantadine, where analog 31 has the greatest activity.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments within the scope of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise.

As used herein, the term "about" means plus or minus 5% of the numerical value of the number with which it is being used. Therefore, about 50% means in the range of 45%-55%.

"Administering" when used in conjunction with a therapeutic means to administer a therapeutic directly to a subject, whereby the agent positively impacts the target. "Administering" a composition may be accomplished by, for example, injection, oral administration, topical administration, or by these methods in combination with other known techniques. Such combination techniques include heating, radiation, ultrasound and the use of delivery agents. When a compound is provided in combination with one or more other active agents, "administration" and its variants are each understood to include concurrent and sequential provision of the compound or salt and other agents.

By "pharmaceutically acceptable" it is meant a carrier, diluent, adjuvant, or excipient must be compatible with other ingredients of the formulation and not deleterious to the recipient thereof.

"Composition" as used herein is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s), and the inert ingredient(s) that make up carrier, diluent, adjuvant, or excipient, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions within the scope of the present invention encompass any composition made by admixing a compound within the scope of the present invention and a pharmaceutically acceptable carrier, diluent, adjuvant, or excipient.

As used herein, the term "agent," "active agent," "active ingredient," "therapeutic agent," or "therapeutic" means a compound or composition utilized to treat, combat, ameliorate, prevent or improve an unwanted condition or disease of a patient. Furthermore, the term "agent," "active agent," "active ingredient," "therapeutic agent," or "therapeutic" encompasses a combination of one or more of the compounds within the scope of the present invention.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refer to both therapeutic treatment and prophylactic or preventative measures, wherein the object is to prevent or slow down (lessen) an undesired physiological condition, disorder, or disease, or to obtain beneficial or desired clinical results. For the purposes of this invention, beneficial or desired results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease. Treatment includes prolonging survival as compared to expected survival if not receiving treatment.

The term "pharmaceutically-acceptable salts" embraces salts commonly used to form alkali metal salts and to form additional salts of free acids or free bases. The nature of the salt is not critical, provided that it is pharmaceutically-acceptable. Suitable pharmaceutically-acceptable acid addition salts of compounds within the scope of the present invention may prepared from an inorganic acid or from an organic acid. Examples of such inorganic acids are hydrochloric, hydrobromic, hydroiodic, nitric, carbonic, sulfuric and phosphoric acid. Appropriate organic acids may include aliphatic, cycloaliphatic, aromatic, araliphatic, heterocyclic, carboxylic and sulfonic classes of organic acids. Examples of such organic acids include formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydrobenzoic, phylacetic, mandelic, embonic, methanesulfonic, ethanesulfonic, benzenesulfonic, pantothenic, 2-hydroxyethanesulfonic, toluenesulfonic, sulfanilic, cyclohyexylaminosuflonic, stearic, algenic, $\beta$-hydrobutyric, galactaric and galacturnoic acid. Suitable pharmaceutically-acceptable base addition salts of compounds within the scope of the present invention include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, triethylamine, trimethylamine. All the listed salts of the corresponding compound of the invention may be prepared by conventional means known to one of ordinary skill in the art. One example of a conventional method of salt formation is by reacting the appropriate acid or base with the compounds within the scope of the present invention at various mole ratios. Another method is by using different mole ratios of the appropriate acid or base in various solvent systems to control the concentration of the dissociated species of the compounds within the scope of the present invention to maximize salt formation.

As shown in FIG. 1, fourteen novel screening compounds were more effective than amantadine in virus replication assays using the PR8 influenza A H1N1 virus, which contains the S31N mutation in the M2 channel that conveys resistance to amantadine. The fourteen novel small-molecule screening compounds belong to three chemical classes: (1) oxabicyclo; (2) sulfonamide; and (3) amantadine derivatives.

The mechanism of action of these compounds is M2 channel inhibition. The initial screening compounds were specifically designed to be more effective for the S31N M2 channel than amantadine and were identified using computational molecular docking methodology.

Without wishing to be bound by theory, experimental structure-activity-relationship (SAR) data for these fourteen novel small-molecule screening compounds, as depicted below and their activity shown in FIGS. 2 through 23, separate oxabicyclo, sulfonamide, and amantadine compounds that are not potent or significantly less potent M2 channel inhibitors than the oxabicyclo, suflonamide, and amantadine compounds within the scope of the present invention.

Figure 18:
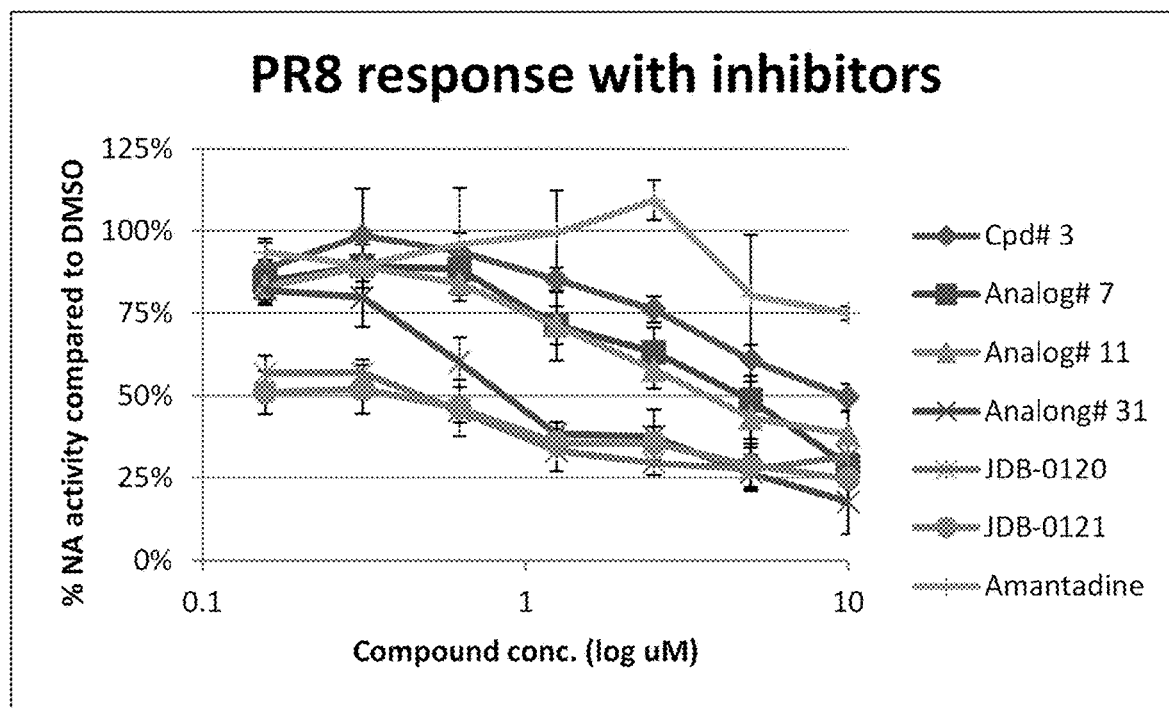
FIG. 18 illustrates antiviral activity for the PR8 strain for sulfonamide class compounds compared to amantadine, where the novel synthetic JDB-0120 and JDB-0121 have the greatest activity.

FIG. 18 presents data regarding two additional compounds—JDB-0120 and JDB-0121—that were synthesized and shown to demonstrate the greatest biological activity in the sulfonamide series.

In certain embodiments, an oxabicyclo compound of Formula 1 below or a pharmaceutically acceptable salt, and all the possible combination thereof, can be provided in a pharmaceutical composition wherein the pharmaceutical ingredient is defined by the following Formula 1:

Wherein: $X_1$, $X_2$, $X_3$, $X_4$, $X_6$, $X_7$, and $X_8$ are independently hydroxyl, methoxy, ethoxy, hydrogen, alkyl, alkenyl, alkynyl, cycloalkyl or aryl, F, Cl, or Br; and $X_5$ is $CH_2OH$, hydroxyl, methoxy, ethoxy, hydrogen, alkyl, alkenyl, alkynyl, cycloalkyl or aryl, F, Cl, or Br.

Exemplary compounds according to Formula 1 include: 4-[5-(hydroxymethyl)-2-methyl-7-oxabicyclo[3.3.1]non-2-en-8-yl]phenol, [8-(4-methoxyphenyl)-2,4,9-trimethyl-7-oxabicyclo[3.3.1]non-2-en-5-yl]methanol, (2,2,6-trimethyl-3-oxabicyclo[3.3.1]non-6-en-4-yl)phenol, 4-[5-(hydroxymethyl)-2,4,9-trimethyl-7-oxabicyclo[3.3.1]non-2-en-8-yl]-2-methoxyphenol In further embodiments, a sulfonylamide compound of Formula 2 below or a pharmaceutically acceptable salt, and all the possible combination thereof, can be provided in a pharmaceutical composition wherein the pharmaceutical ingredient is defined by the following Formula 2:

Formula 2

Ring1 may be either an aryl, heteroaryl, or fused ring (including benzofurazan and phthalide), while Ring2 may be either either a an aryl or heteroaryl ring. $X_1$, $X_2$, $X_4$, $X_5$, $X_6$, $X_7$, $X_8$, $X_9$, $X_{10}$, $X_{11}$, and $X_{12}$ are hydroxyl, methoxy, ethoxy, hydrogen, alkyl, alkenyl, alkynyl, cycloalkyl or aryl, F, Cl, or Br. $X_3$ is a nitro, nitrile, carboxyl, ester, sulfonamide, methylsulfone, hydroxyl, methoxy, ethoxy, hydrogen, alkyl, alkenyl, alkynyl, cycloalkyl or aryl, F, Cl, or Br.

Exemplary compounds according to Formula 2 include: N-benzyl-2,4,6-trimethylbenzenesulfonamide, 2,4,6-trimethyl-N-[(3-methylphenyl)methyl]benzenesulfonamide, N-[(2-chlorophenyl)methyl]-2,4,6 trimethylbenzenesulfonamide, 2,6-dimethyl-4-nitro-N-(pyridin-2-ylmethyl) benzenesulfonamide, N-[(2-methoxyphenyl)methyl]-2,4,6 trimethylbenzenesulfonamide.

The following list of compounds are preferred embodiments included within the scope of the present invention:

Formula 1

Compound #1

IPUAC: 4-[5-(hydroxymethyl)-2-methyl-7-oxabicyclo [3.3.1]non-2-en-8-yl]phenol

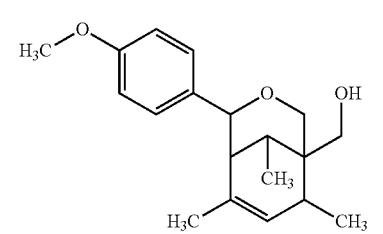

IPUAC: [8-(4-methoxyphenyl)-2,4,9-trimethyl-7-oxabicyclo[3.3.1]non-2-en-5-yl]methanol Analog #2

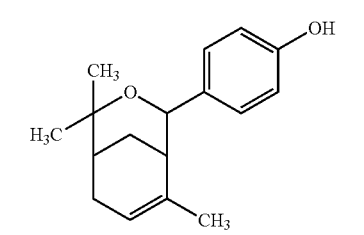

IPUAC: 4-(2,2,6-trimethyl-3-oxabicyclo[3.3.1]non-6-en-4-yl)phenol

Analog #4

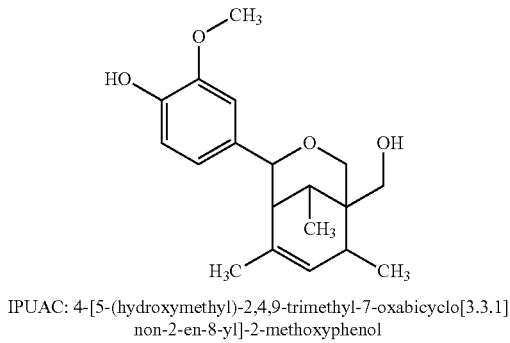

IPUAC: 4-[5-(hydroxymethyl)-2,4,9-trimethyl-7-oxabicyclo[3.3.1]non-2-en-8-yl]-2-methoxyphenol Analog #5

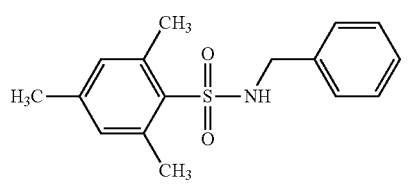

IPUAC: N-benzyl-2,4,6-trimethylbenzenesulfonamide

Compound #3

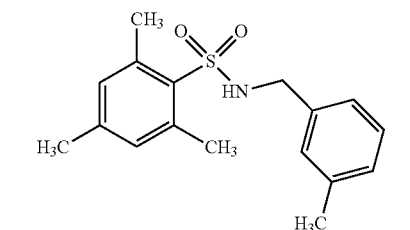

IPUAC: 2,4,6-trimethyl-N-[(3-methylphenyl)methyl]benzenesulfonamide

Analog #7

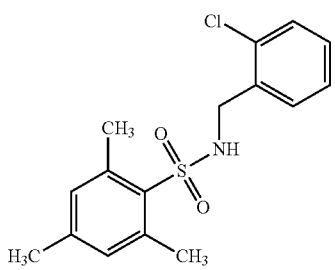

IPUAC: N-[(2-chlorophenyl)methyl]-2,4,6-trimethylbenzenesulfonamide

Analog #11

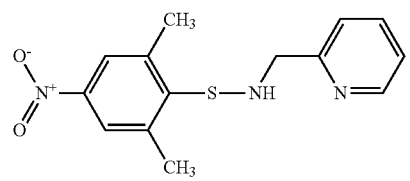

IPUAC: 2,6-dimethyl-4-nitro-N-(pyridin-2-ylmethyl)benzenesulfonamide

Analog #27

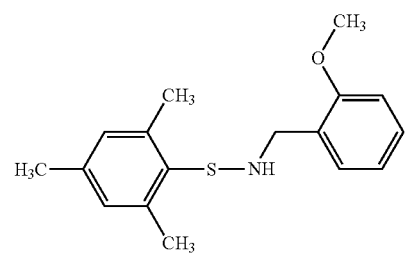

IPUAC: N-[(2-methoxyphenyl)methyl]-2,4,6-trimethylbenzenesulfonamide

Analog #31

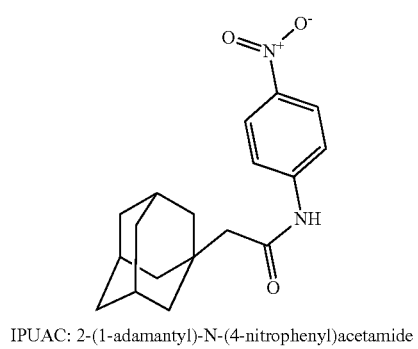

IPUAC: 2-(1-adamantyl)-N-(4-nitrophenyl)acetamide

Compound #16

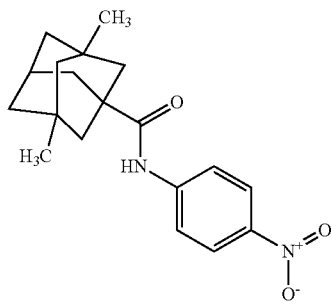

IPUAC: 3,5-dimethyl-N-(4-nitrophenyl)adamantane-1-carboxamide

Analog #21

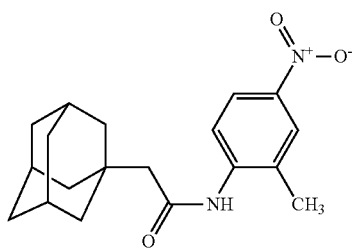

IPUAC: 2-(1-adamantyl)-N-(2-methyl-4-nitrophenyl)acetamide

Compound #19

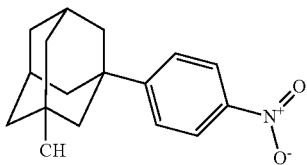

IPUAC: 3-(4-nitrophenyl)adamantan-1-ol

Analog #23

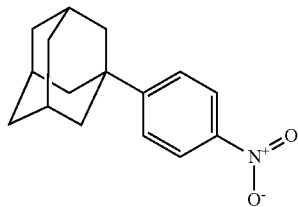

IPUAC: 1-(4-nitrophenyl)adamantane

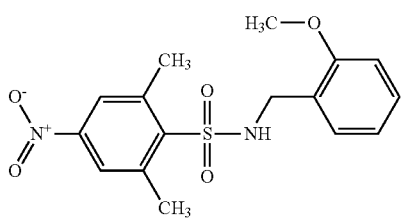

IPUAC: N-[(2-methoxyphenyl)methyl]-2,6-dimethyl-4-nitrobenzene-1-sulfonamide

Analog #18

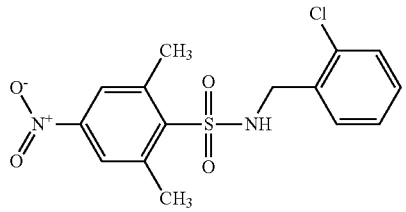

IPUAC: N-[(2-chlorophenyl)methyl]-2,6-dimethyl-4-nitrobenzene-1-sulfonamide

The compounds described herein are tested for efficacy against infection in the protocol as described below and in the figures. In certain situations, the compounds described herein are preferentially suitable for treatment of influenza A where the strains have proven to be amantadine resistant.

JDB-0120 was synthesized as follows: 2,6-dimethyl-4-nitrobenzene-1-sulfonyl chloride (25 mg, 0.1 mmol) (EN300-98212 purchased from Enamine BB) was added to a stirred solution of 2-methoxybenzylamine (15 mg, 0.11 mmol) (159883 purchased from Sigma Aldrich) in a solution of pyridine (1 ml) and CH2Cl2 (2.5 ml) at room temperature. The mixture was stirred for 24 hours at room temperature and the reaction progress was monitored with TLC. At 24 h, the reaction was quenched with 5% aqueous HCl solution (1 mL). The mixture was diluted with $CH_2Cl_2$ (20 mL) and was subsequently washed with 5% aqueous HCl (3×10 mL). The organic layer was separated, dried with $Na_2SO_4$ and concentrated to provide a residue that was purified by column chromatography (0-50% EtOAc-Hexanes) to give the desired product JDB-0120 as a white solid (29 mg, 82.8%). $^1$H NMR (400 MHz, CDCl$_3$) δ 2.70 (s, 6H), 3.77 (s, 3H), 4.18 (d, J=6.4 Hz, 2H), 5.44 (t, H=6.2 Hz, 1H), 6.68 (m, 2H), 6.89, (dd, J=7.8, 1.47 Hz, 1H), 7.13 (dd, J=7.9, 1.6 Hz, 1H), 7.79 (s, 2H). MS (ESI, m/z): 373.08 [M+Na]$^+$.

JDB-0121 was synthesized as follows: 2,6-dimethyl-4-nitrobenzene-1-sulfonyl chloride (25 mg, 0.1 mmol) (EN300-98212 purchased from Enamine BB) was added to a stirred solution of 2-Chlorobenzylamine (16 mg, 0.11 mmol) (C27204 purchased from Sigma Aldrich) in a solution of pyridine (1 ml), triethylamine (1 ml) and $CH_2Cl_2$ (2.5 ml) at room temperature. The mixture was stirred for 24 hours and the reaction progress was monitored with TLC. At 24 h, the reaction was quenched with 5% aqueous HCl solution (1 mL). The mixture was diluted with $CH_2Cl_2$ (20 mL) and was subsequently washed with 5% HCl (3×10 mL). The organic layer was separated, dried with $Na_2SO_4$ and concentrated to provide a residue that was purified by column chromatography (0-50% EtOAc-Hexanes) to give the desired product JDB-0121 as an off-white solid (23 mg, 64.9%). $^1$H NMR (400 MHz, CDCl$_3$) δ 2.75 (s, 6H), 4.31 (d, J=6.0 Hz, 2H), 5.22 (t, H=6.2 Hz, 1H), 7.10 (m, 2H), 7.15 (dd, J=9.6, 1.6 Hz, 1H), 7.27 (dd, J=7.9, 1.6 Hz, 1H), 7.87 (s, 2H). MS (ESI, m/z): 377.03 [M+Na]$^+$.

Administration and Compositions

The compounds within the scope of the present invention and pharmaceutically-acceptable salts thereof can be administered by means that produces contact of the active agent with the agent's site of action. They can be administered by conventional means available for use in conjunction with pharmaceuticals in a dosage range of 0.001 to 1000 mg/kg of mammal (e.g. human) body weight per day in a single dose or in divided doses. One dosage range is 0.01 to 500 mg/kg body weight per day orally in a single dose or in divided doses. Administration can be delivered as individual therapeutic agents or in a combination of therapeutic agents. They can be administered alone, but typically are administered with a pharmaceutically acceptable excipient selected on the basis of the chosen route of administration and standard pharmaceutical practice.

Compounds can be administered by one or more ways. For example, the following routes may be utilized: oral, parenteral (including subcutaneous injections, intravenous, intramuscular, intrasternal injection or infusion techniques), inhalation, buccal, sublingual, or rectal, in the form of a unit dosage of a pharmaceutical composition containing an effective amount of the compound and optionally in combination with one or more pharmaceutically-acceptable excipients such as stabilizers, anti-oxidants, lubricants, bulking agents, fillers, carriers, adjuvants, vehicles, diluents and other readily known excipients in standard pharmaceutical practice.

Liquid preparations suitable for oral administration (e.g. suspensions, syrups, elixirs and other similar liquids) can employ media such as water, glycols, oils, alcohols, and the like. Solid preparations suitable for oral administration (e.g. powders, pills, capsules and tablets) can employ solid excipients such as starches, sugars, kaolin, lubricants, binders, disintegrating agents, antioxidants and the like.

Parenteral compositions typically employ sterile water as a carrier and optionally other ingredients, such as solubility aids. Injectable solutions can be prepared, for example, using a carrier comprising a saline solution, a glucose solution or a solution containing a mixture of saline and glucose. Further guidance for methods suitable for use in preparing pharmaceutical compositions is provided in *Remington: The Science and Practice of Pharmacy*, 21$^{st}$ edition (Lippincott Williams & Wilkins, 2006).

Other embodiments of the invention include the active agent prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

In another exemplary embodiment, an oily preparation of an active agent prepared as described above may be lyophilized to form a solid that may be mixed with one or more pharmaceutically acceptable excipient, carrier or diluent to form a tablet, and in yet another embodiment, the active agent may be crystallized to from a solid which may be combined with a pharmaceutically acceptable excipient, carrier or diluent to form a tablet.

The means and methods for tableting are known in the art and one of ordinary skill in the art can refer to various references for guidance. For example, *Pharmaceutical Manufacturing Handbook: Production and Processes*, Shayne Cox Gad, John Wiley & Sons, Inc., Hoboken, N.J. (2008), which is hereby incorporated by reference in its entirety can be consulted.

Therapeutic compounds can be administered in a dosage range of about 0.001 to 1000 mg/kg of mammal (e.g. human) body weight per day in a single dose or in divided doses. One dosage range is about 0.01 to 500 mg/kg body weight per day orally in a single dose or in divided doses.

For oral administration, the compositions can be provided in the form of tablets or capsules containing about 1.0 to 1000 mg of the active ingredient, particularly about 1, 5, 10, 15, 20, 25, 50, 75, 100, 150, 200, 250, 300, 400, 500, 750, and 1000 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In view of the factors affecting the specific dose level and frequency it is contemplated that the dose frequency can range from multiple doses daily to monthly dosages. The preferred dose frequency ranges from twice a day to every two weeks. A more preferred dose frequency ranges from twice a day to weekly. A most preferred dose frequency ranges from twice a day to twice a week.

In the methods of various embodiments, pharmaceutical compositions including the active agent can be administered to a subject in an "effective amount." An effective amount may be any amount that provides a beneficial effect to the patient, and in particular embodiments, the effective amount is an amount that may (1) prevent the subject from experiencing one or more adverse effects associated with a administered agents, such as those used to diagnose, identify, and treat medical conditions, (2) reduce side effects experienced by the subject as a result of a medical therapy or reduce the side effects known to result from such therapies, and/or (3) eliminate side effects resulting from a medical treatment experienced by the subject prior to administration of the active agent or eliminate the side effects known to result from such treatment.

The means and methods for administration are known in the art and an artisan can refer to various pharmacologic references for guidance. For example, Modern Pharmaceutics, Banker & Rhodes, Marcel Dekker, Inc. (1979); and *Goodman & Gilman's, The Pharmaceutical Basis of Therapeutics*, 6th Edition, MacMillan Publishing Co., New York (1980) both of which are hereby incorporated by reference in their entireties can be consulted.

In preferred embodiments, a preferred method of treatment comprises the step of administering to a patient having influenza A an effective amount of a pharmaceutical composition comprising one of the compounds identified herein. In a further embodiment, an additional step comprises testing the patient for influenza A strain and determining whether said strain is amantadine-resistant, whereby the subsequent step is to administer to the patient an effective amount of the active ingredient or pharmaceutical compositions described herein.

The compounds as described herein are made under ordinary chemical synthesis by one of ordinary skill in the art. Furthermore, the compounds can thereafter be formulated into compositions suitable for oral or injectable administration to a human patient.

Bioactivity

In Vitro 4-MUNANA Assay to Determine Compound IC50 for Influenza Infection

Indicated compounds were purchased, suspended in DMSO at stock concentrations of 10 mM, and stored in aliquots at −20 C. Fibroblast cells L929 (2.5×10$^4$/well) were pretreated with half-log dilutions of indicated compounds for 30 minutes in PBS/BSA (0.1%). Then, pre-treated cells were infected with influenza virus diluted in cold PBS/BSA (0.1%) for 30 minutes. Virus stocks used in the experiments were Influenza A virus strain A/Puerto Rico/8/1934 H1N1 (PR8; amantadine-resistant) and Influenza B virus strain B/Lee/1940 (B/Lee; amantadine-insensitive). Infected cells were maintained in the presence of compounds overnight (18-20 hours) until the assay was developed. To screen for inhibition of infection, we monitored neuraminidase (NA) activity as a read-out for viral protein synthesis/replication. The cells were lysed in the presence of 4-MUNANA, a fluorometric substrate specific for active NA. Substrate cleavage by intracellular NA resulted in a fluorescence signal that was read at 340/510 nm using a Wallac1420 plate reader.

Figure 27A:
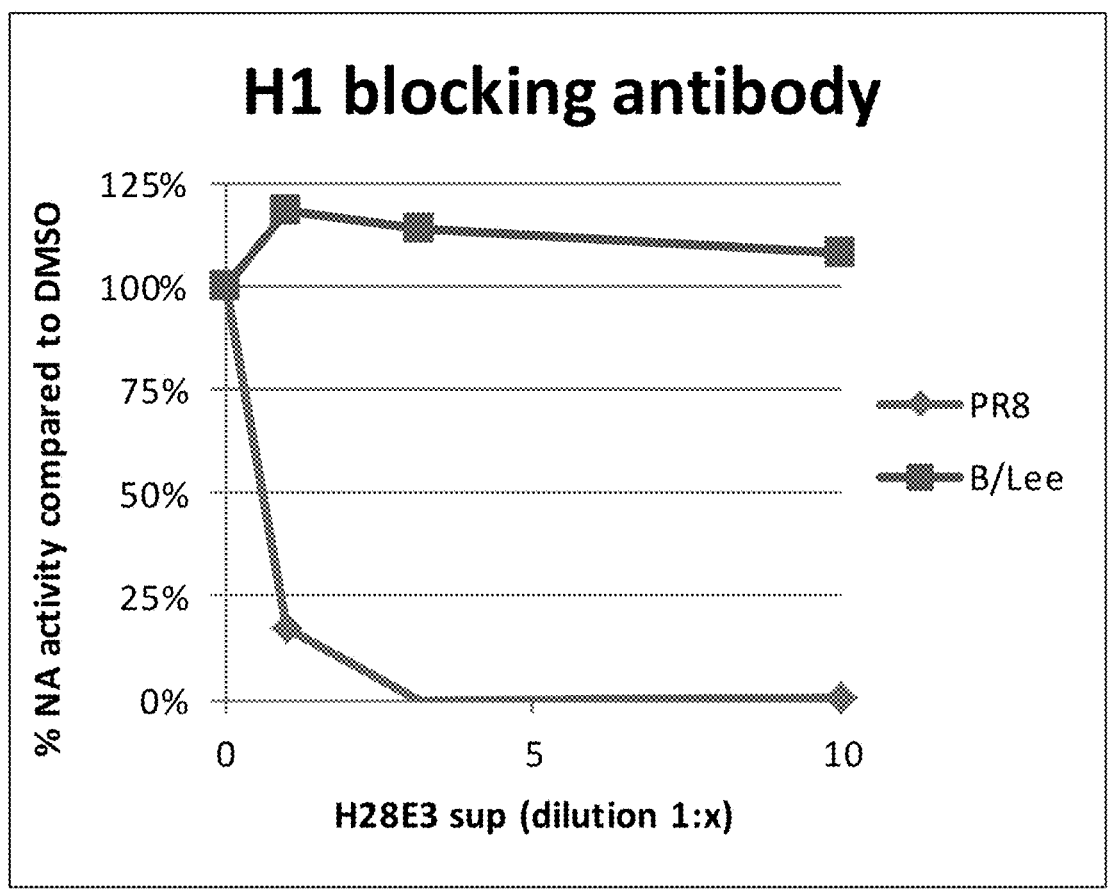
FIGS. 27A-B illustrates the controls used to determine effective inhibition of PR8 virus replication and prevention of infection. The positive control shown in FIG. 27A represents inhibition of PR8 virus replication by antibody H28E3. The partial positive control shown in FIG. 27B represents inhibition of PR8 virus replication by amantadine. Although the PR8 virus contains the amantadine-resistant S31N mutation, amantadine treatment moderately inhibited PR8 replication at high enough concentrations.
Figure 27B:
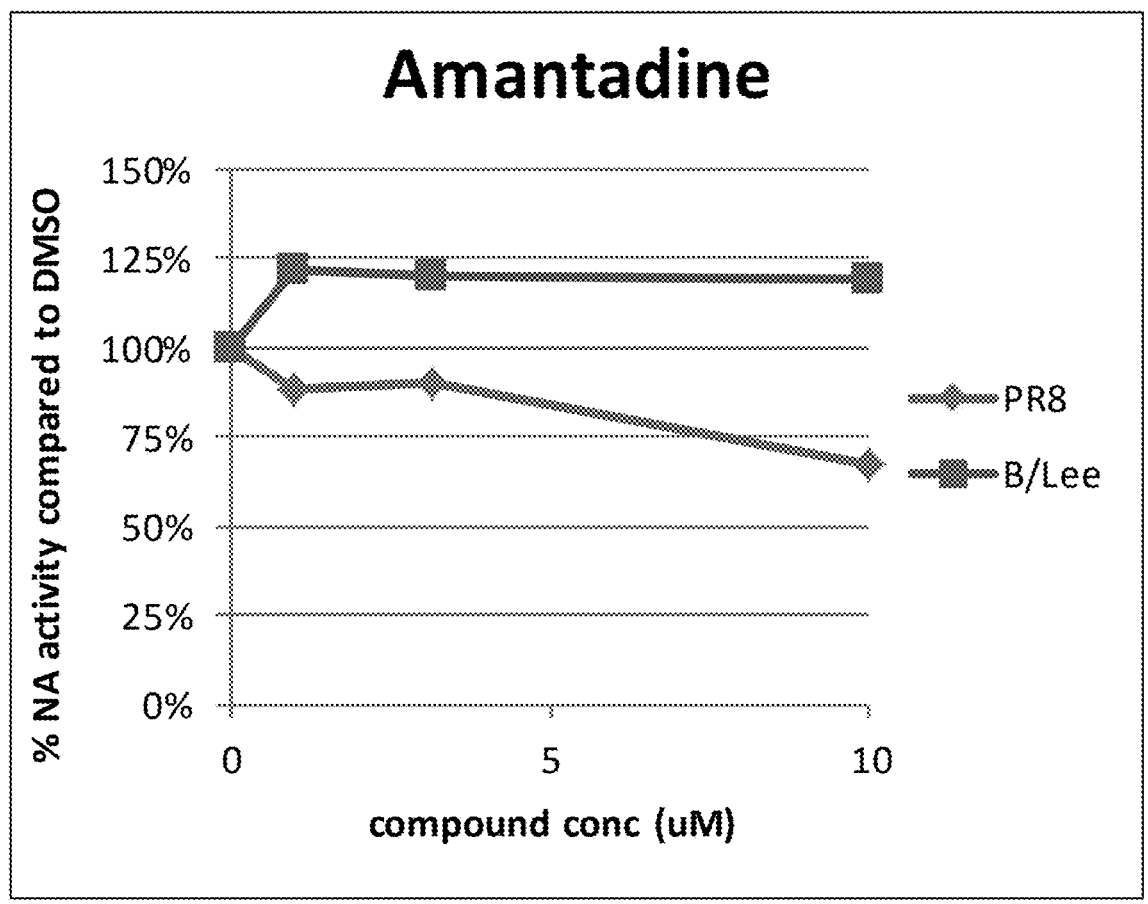

FIGS. 26 and 27A-B, show two controls were included in the screen. As a positive control, H28E3 (anti-H1) antibody effectively blocked infection and replication of PR8 virus (FIG. 27A), with no impact on B/Lee virus (which contains a non-homologous HA protein). Surface hemagglutinin on the virion binds to sialic acids on the cells and is essential for viral entry. The H1 antibody effectively blocks viral entry of the cell by binding to surface hemagglutinin. Despite PR8 containing the amantadine-resistant S31N mutation, amantadine treatment moderately inhibited PR8 replication (FIG. 27B) at high enough concentrations, without affecting B/Lee (which contains non-homologous BM2 sequence). This showed that under certain conditions, we could detect inhibition of PR8 replication using this assay format. Accordingly, amantadine was used as a partial positive control.

As shown in FIG. 21, a series of promising compounds were screened using the in vitro 4-MUNANA assay described above. The compounds were first tested in half-log dilutions at concentrations ranging from 1-10 alongside DMSO (as a negative control) and amantadine (as a partial positive control). The fluorescence values were normalized to the DMSO control.

The bold boxes in FIG. 21 identify the four compounds (1, 3, 16, and 19) that showed selective activity against PR8 strain. Using the same in vitro 4-MUNANA assay, compounds 1, 3, 16, and 19 were tested using a larger concentration range of 0.1-100 μM (FIG. 22).

Figure 23A:
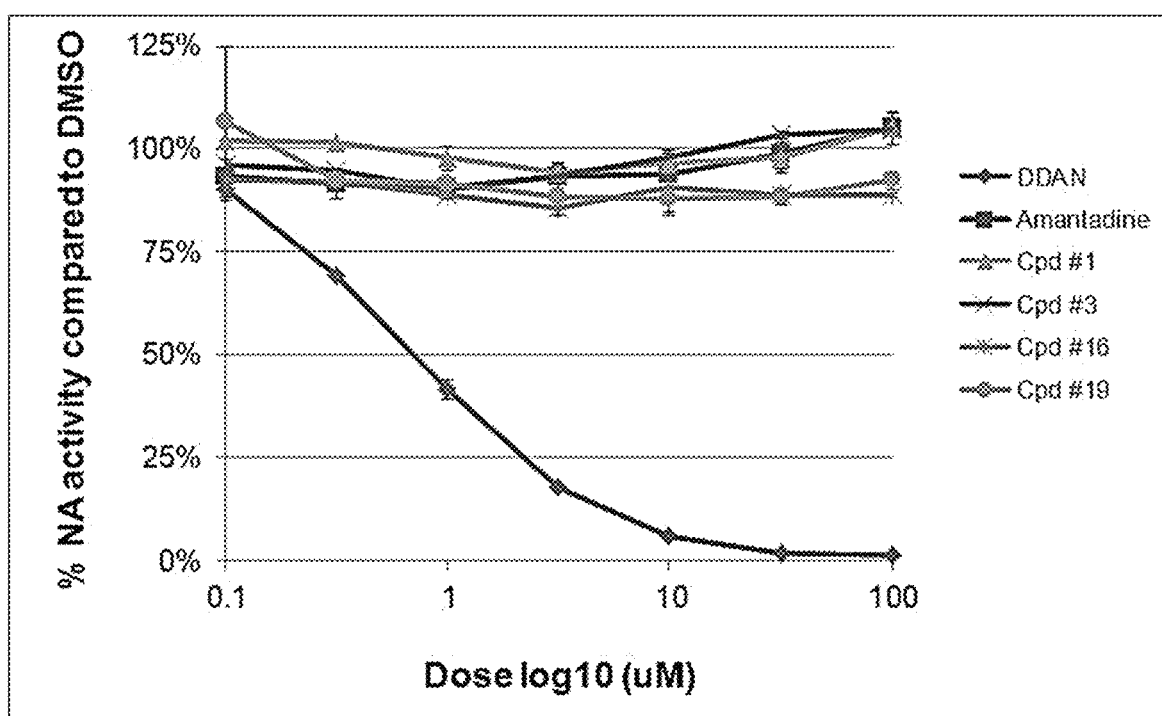
FIG. 23A-B illustrates that the compounds from the sulfonamide series do not have NA activity supporting indicating that neuraminidase inhibition by the sulfonamide series of compounds is modulated at the M2 channel protein.
Figure 23B:
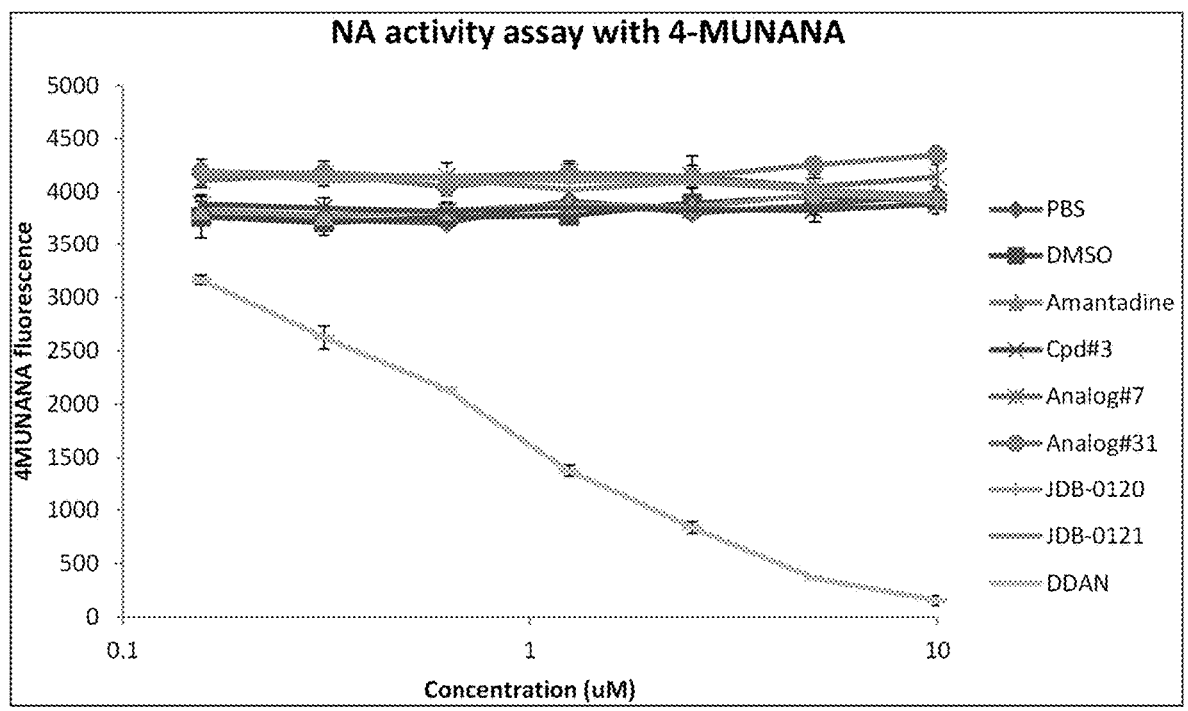
Figure 24:
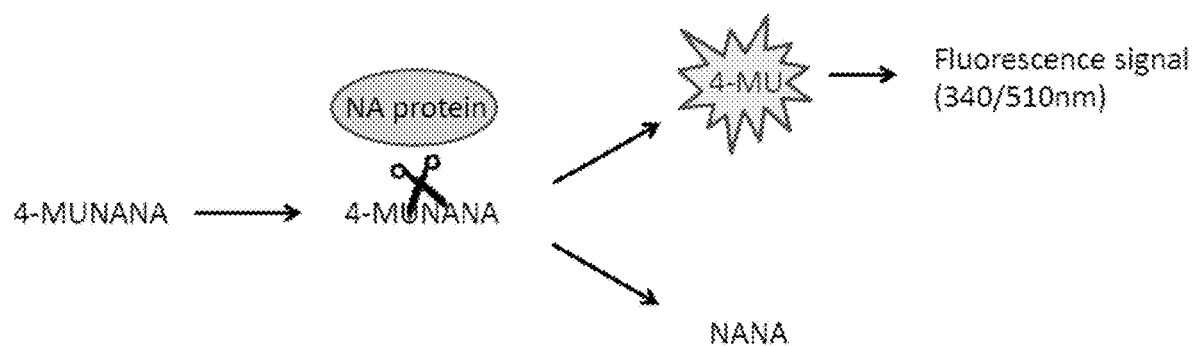
FIG. 24 depicts the NA activity assay.

Since the in vitro 4-MUNANA assay detects active neuraminidase (NA), there is the possibility that the observed inhibition could be explained by direct inhibition of NA activity and not due to direct interaction with the M2 channel. To rule out this possibility, assays which used PR8 virus stocks (which contain active NA surface proteins) were pre-treated with select compounds for 30 minutes. A previously described neuraminidase inhibitor, DDAN (N-Acetyl-2,3-dehydro-2-deoxyneuraminic acid), was included as a positive control. After 30 minutes, the 4-MUNANA substrate was added to screen for neuraminidase (NA) activity. Responses were normalized to DMSO. As shown in FIG. 23A-B, DDAN effectively inhibited NA activity in a dose-dependent manner, whereas the test compounds had no impact, even at the highest concentration (100 μM). Based on this data, the observed loss of in vitro NA activity following drug treatment is not due to an indirect inhibition of NA protein. FIG. 23A specifically confirms that NA inhibition by compounds 1, 3, 16, and 19 is due to M2 channel inhibition, not an indirect inhibition of NA protein. FIG. 23B specifically confirms that NA inhibition by compound 3, analog 7, analog 31, JDB-0120, and JDB-0121 is also due to M2 channel inhibition, not an indirect inhibition of NA protein.

As shown in FIGS. 1 through 20, analogs of compounds 1, 3, 16, and 19 were tested to (1) determine which compounds exhibited the most potent inhibition of neuraminidase (NA) and (2) establish structure activity relationship (SAR).

FIGS. 3A-B, 7A-B, 8, 10A-B, 11, 15A-B, 16A-B, and 17 demonstrate the potency of analogs within the sulfonamide class of compounds, where analogs 7, 11, and 31 were shown to be potent inhibitors of NA activity and PR8 virus replication.

Figure 19:
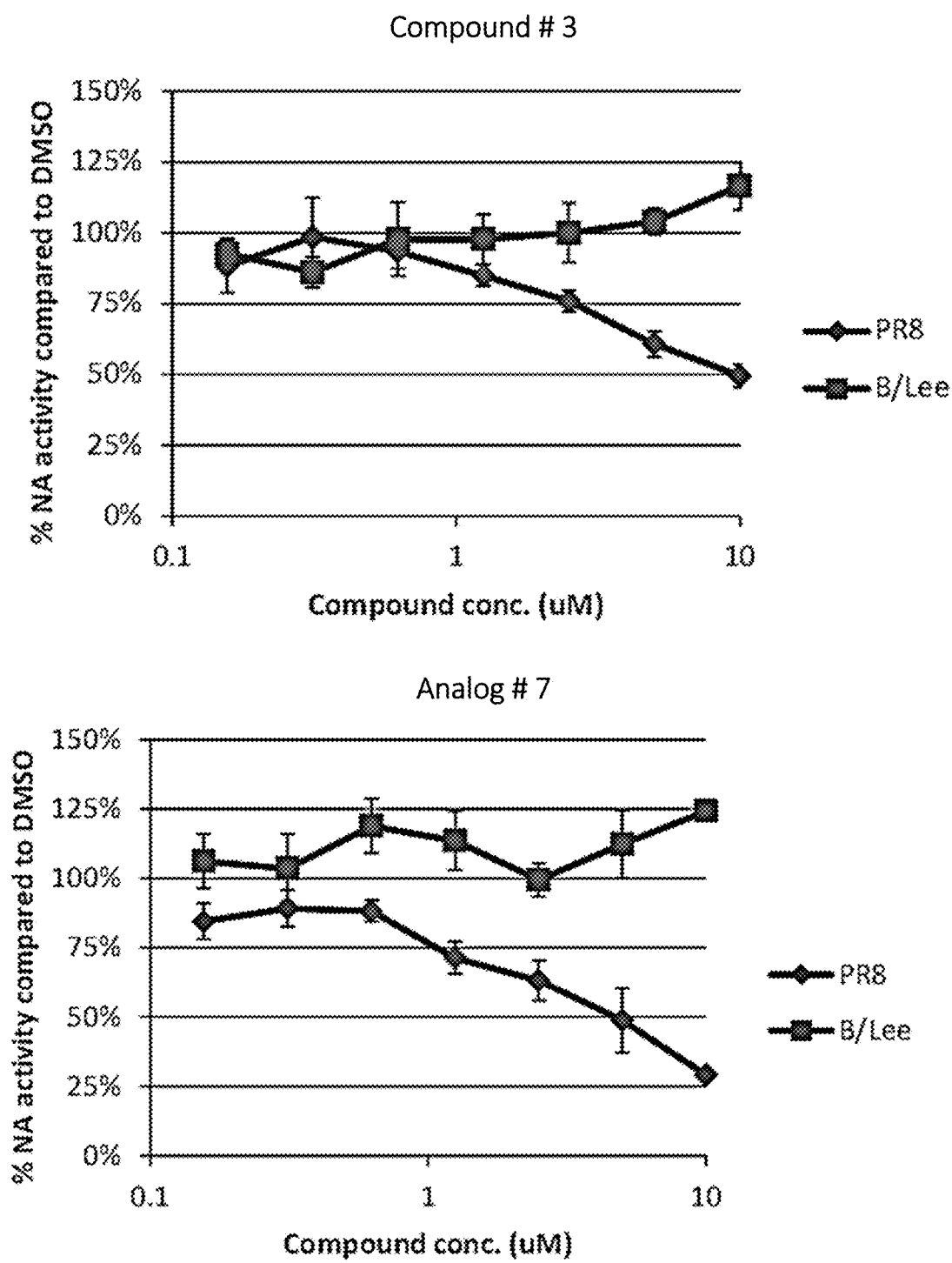
FIG. 19 depicts antiviral activity for the PR8 strain but not the B/Lee Strain for sulfonamide class compounds compared to amantadine, where the novel synthetic JDB-0120 and JDB-0121 have the greatest activity.
Figure 20:
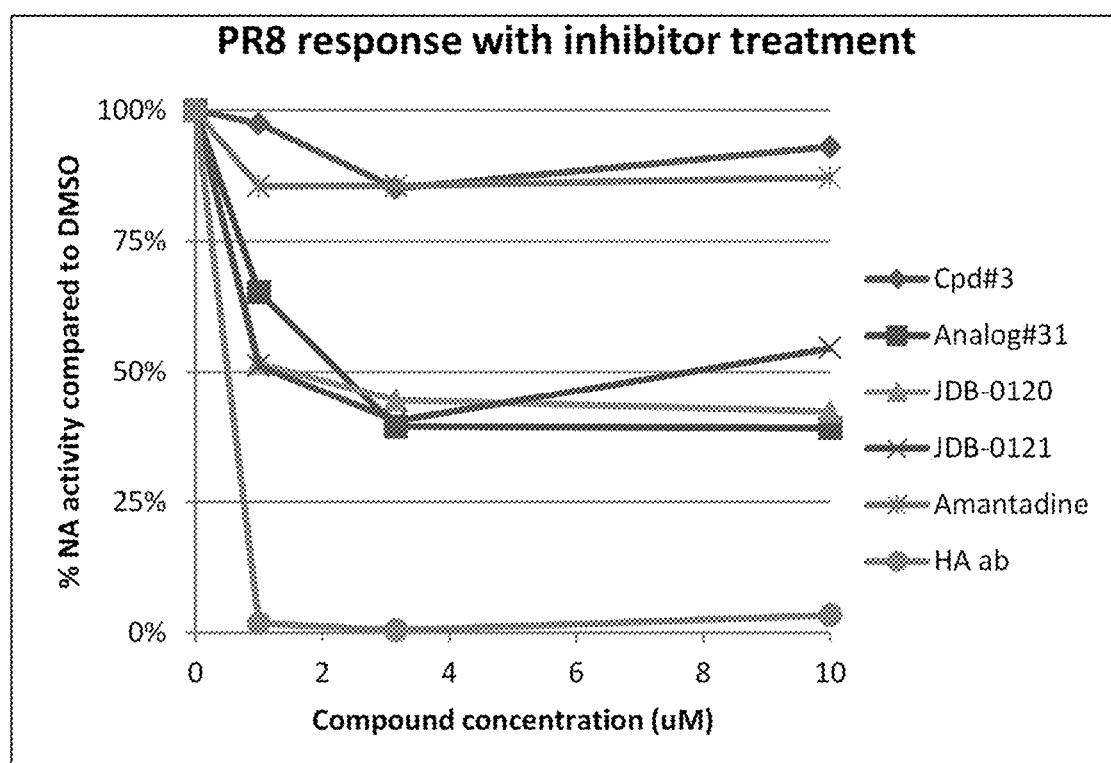
FIG. 20 shows antiviral activity for the PR8 strain for sulfonamide class compounds compared to amantadine, where the novel synthetic JDB-0120 and JDB-0121 have the greatest activity for small molecules and an antibody for HA shows maximum possible positive control activity.

As shown in FIGS. 18, 19, and 20, JDB-0120 and JDB-0121 were the most potent inhibitors of NA activity and PR8 virus replication in the class sulfonamide compounds.

FIGS. 2A-B, 6A-B, and 9 illustrate the antiviral activity for the PR8 strain and inhibition of NA activity for oxabicyclo compound 1 and analogs 2, 4, and 5 compared to amantadine, where analog 4 is the most potent.

FIGS. 4A-C, 5A-B, 12, 13A-F, 14 illustrates the antiviral activity for the PR8 strain and inhibition of NA activity for amantadine derivatives, where analog 18 was found to be the most potent.

What is claimed is:

1. A method of treating amantadine-resistant influenza A infections comprising administering an effective amount of a compound of Formula 1:

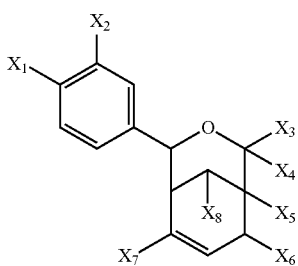

wherein $X_1$, $X_2$, $X_3$, $X_4$, $X_6$, $X_7$, and $X_8$ are independently a hydroxyl, methoxy, ethoxy, hydrogen, alkyl, alkenyl, alkynyl, cycloalkyl or aryl, F, Cl, or Br; and $X_5$ is a $CH_2OH$, hydroxyl, methoxy, ethoxy, hydrogen, alkyl, alkenyl, alkynyl, cycloalkyl or aryl, F, Cl, or Br; or a pharmaceutically acceptable salt thereof.

2. The method of claim 1, wherein the compound is selected from the group consisting of 4-[5-(hydroxymethyl)-2-methyl-7-oxabicyclo[3.3.1]non-2-en-8-yl]phenol, [8-(4-methoxyphenyl)-2,4,9-trimethyl-7-oxabicyclo[3.3.1]non-2-en-5-yl]methanol, 4-(2,2,6-trimethyl-3-oxabicyclo[3.3.1]non-6-en-4-yl)phenol, 4-[5-(hydroxymethyl)-2,4,9-trimethyl-7-oxabicyclo[3.3.1]non-2-en-8-yl]-2-methoxyphenol, N-benzyl-2,4,6-trimethylbenzenesulfonamide, 2,4,6-trimethyl-N-[(3-methylphenyl)methyl]benzenesulfonamide, N-[(2-chlorophenyl)methyl]-2,4,6 trimethylbenzenesulfonamide, 2,6-dimethyl-4-nitro-N-(pyridin-2-ylmethyl) benzenesulfonamide, and N-[(2-methoxyphenyl)methyl]-2,4,6 trimethylbenzenesulfonamide; 2-(1-adamantyl)-N-(4-nitrophenyl)acetamide, 3,5-dimethyl-N-(4-nitrophenyl)adamantane-1-carboxamide, 2-(1-adamantyl)-N-(2-methyl-4-nitrophenyl)acetamide, 3-(4-nitrophenyl)adamantan-1-ol, 1-(4-nitrophenyl)adamantane, or a pharmaceutically acceptable salt of any of these compounds.

3. The method of claim 2, wherein the compound is selected from the group consisting of 2-(1-adamantyl)-N-(4-nitrophenyl)acetamide, 3,5-dimethyl-N-(4-nitrophenyl)adamantane-1-carboxamide, 2-(1-adamantyl)-N-(2-methyl-4-nitrophenyl)acetamide, 3-(4-nitrophenyl)adamantan-1-ol, 1-(4-nitrophenyl)adamantane, or a pharmaceutically acceptable salt of any of these compounds.

4. A compound selected from the group consisting of 2-(1-adamantyl)-N-(4-nitrophenyl)acetamide, 3,5-dimethyl-N-(4-nitrophenyl)adamantane-1-carboxamide, 2-(1-adamantyl)-N-(2-methyl-4-nitrophenyl)acetamide, 3-(4-nitrophenyl)adamantan-1-ol, 1-(4-nitrophenyl)adamantane, or a pharmaceutically acceptable salt of any of these compounds.

5. A pharmaceutical composition comprising an effective amount of a compound of claim 4 and a pharmaceutically-acceptable diluent or carrier.

6. A method of treating amantadine-resistant influenza A infections comprising administering a pharmaceutical composition comprising of claim 5.

7. A method of treating amantadine-resistant influenza A infections comprising administering a pharmaceutical composition comprising an effective amount of 4-(2,2,6-trimethyl-3-oxabicyclo[3.3.1]non-6-en-4-yl)phenol; and a pharmaceutically-acceptable diluent or carrier.

* * * * *

SEQUENCE LISTING

```
<160> NUMBER OF SEQ ID NOS: 2

<210> SEQ ID NO 1
<211> LENGTH: 97
<212> TYPE: PRT
<213> ORGANISM: Artificial Sequence
<220> FEATURE:
<223> OTHER INFORMATION: PR8

<400> SEQUENCE: 1

Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Thr Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60
```

```
Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 2
<211> LENGTH: 109
<212> TYPE: PRT
<213> ORGANISM: Artificial Sequence
<220> FEATURE:
<223> OTHER INFORMATION: B/Lee

<400> SEQUENCE: 2

Met Leu Glu Pro Leu Gln Ile Leu Ser Ile Cys Ser Phe Ile Leu Ser
1               5                   10                  15

Ala Leu His Phe Met Ala Trp Thr Ile Gly His Leu Asn Gln Ile Lys
                20                  25                  30

Arg Gly Val Asn Leu Lys Ile Gln Ile Arg Asn Pro Asn Lys Glu Ala
            35                  40                  45

Leu Asn Arg Glu Val Ser Ile Leu Arg His Asn Tyr Gln Lys Glu Ile
        50                  55                  60

Gln Ala Lys Glu Thr Met Lys Lys Ile Leu Ser Asp Asn Met Glu Val
65                  70                  75                  80

Leu Gly Asp His Ile Val Val Glu Gly Leu Ser Thr Asp Glu Ile Ile
                85                  90                  95

Lys Met Gly Glu Thr Val Leu Glu Val Glu Glu Leu Gln
                100                 105
```